United States Patent
Levine et al.

(10) Patent No.: US 10,299,786 B2
(45) Date of Patent: May 28, 2019

(54) SURGICAL SUTURING DEVICE WITH TRANSVERSE ENGAGEMENT

(71) Applicant: Alpha Scientific Corporation, Exton, PA (US)

(72) Inventors: David E. Levine, Devon, PA (US); Neal B. Cohen, Hatboro, PA (US); Daniel S. Levine, Wayne, PA (US); Marshall S. Levine, Wayne, PA (US)

(73) Assignee: Alpha Scientific Corporation, Exton, PA (US)

( * ) Notice: Subject to any disclaimer, the term of this patent is extended or adjusted under 35 U.S.C. 154(b) by 571 days.

(21) Appl. No.: 14/773,626

(22) PCT Filed: Mar. 17, 2014

(86) PCT No.: PCT/US2014/030533
§ 371 (c)(1),
(2) Date: Sep. 8, 2015

(87) PCT Pub. No.: WO2014/145724
PCT Pub. Date: Sep. 18, 2014

(65) Prior Publication Data
US 2016/0038141 A1 Feb. 11, 2016

Related U.S. Application Data

(60) Provisional application No. 61/852,050, filed on Mar. 15, 2013.

(51) Int. Cl.
*A61B 17/04* (2006.01)
*A61B 17/06* (2006.01)
(Continued)

(52) U.S. Cl.
CPC ...... *A61B 17/0485* (2013.01); *A61B 17/0469* (2013.01); *A61B 17/062* (2013.01);
(Continued)

(58) Field of Classification Search
CPC ............ A61B 17/0469; A61B 17/0485; A61B 17/06109; A61B 17/062; A61B 2017/00349
See application file for complete search history.

(56) References Cited

U.S. PATENT DOCUMENTS

| 669,034 A | 2/1901 | Manly |
|---|---|---|
| 755,921 A | 3/1904 | O'Neill |

(Continued)

FOREIGN PATENT DOCUMENTS

| DE | 102009007722 A1 | 8/2010 |
|---|---|---|
| EP | 1598017 A1 | 11/2005 |

(Continued)

OTHER PUBLICATIONS

Office Action dated Feb. 29, 2016 in CA Application No. 2,757,248.
(Continued)

*Primary Examiner* — Julie A Szpira
(74) *Attorney, Agent, or Firm* — Panitch Schwarze Belisario & Nadel LLP

(57) ABSTRACT

A minimally invasive suture insertion device utilizing small gage needles is provided for threading one or more sutures through subcutaneous tissue, both locally and from remote access points, to support, attach, sever, ligate or constrict tissue, vessels, ligaments, nerves or other anatomical features, or for pulling another device into position defined by a suture pathway. A manually operated suture transfer device and method are provided for use in various surgical applications. The suture transfer device operates as an instrument for inserting sutures into and through desired pathways. Tethered cannulas are coupled to the positioned sutures and dock, transversely, with a captured component having a (Continued)

capacity for engaging a single suture or multiple sutures, together or in turn within subcutaneous tissue from local or remote access points.

40 Claims, 72 Drawing Sheets

(51) Int. Cl.
*A61B 17/062* (2006.01)
*A61B 17/00* (2006.01)
*A61B 90/00* (2016.01)

(52) U.S. Cl.
CPC .......... *A61B 17/06109* (2013.01); *A61B 2017/00349* (2013.01); *A61B 2017/00876* (2013.01); *A61B 2017/061* (2013.01); *A61B 2017/06009* (2013.01); *A61B 2017/06042* (2013.01); *A61B 2090/0807* (2016.02)

(56) References Cited

U.S. PATENT DOCUMENTS

| | | | |
|---|---|---|---|
| 1,874,668 A | 8/1932 | Wadewitz |
| 2,665,692 A | 1/1954 | L'esperance |
| 2,860,902 A | 11/1958 | Diels |
| 2,913,270 A | 11/1959 | Sachsenroeder, Sr. |
| 3,550,166 A | 12/1970 | Kotler |
| 3,739,784 A | 6/1973 | Itoh |
| 3,903,892 A | 9/1975 | Komiya |
| 3,910,279 A | 10/1975 | Okada et al. |
| 3,915,419 A | 10/1975 | Brown et al. |
| 4,008,912 A | 2/1977 | Kotov |
| 4,306,561 A | 12/1981 | de Medinaceli |
| 4,312,337 A | 1/1982 | Donohue |
| 4,635,636 A | 1/1987 | Goldstein |
| 4,638,802 A | 1/1987 | Okada |
| 4,655,223 A | 4/1987 | Kim |
| 5,224,488 A | 7/1993 | Neuffer |
| 5,250,054 A | 10/1993 | Li |
| 5,318,578 A | 6/1994 | Hasson |
| 5,376,096 A | 12/1994 | Foster |
| 5,387,227 A | 2/1995 | Grace |
| 5,480,406 A | 1/1996 | Nolan et al. |
| 5,569,271 A | 10/1996 | Hoel |
| 5,624,446 A | 4/1997 | Harryman, II |
| 5,645,548 A | 7/1997 | Augsburger |
| 5,681,331 A | 10/1997 | de la Torre et al. |
| 5,707,379 A | 1/1998 | Fleenor et al. |
| 5,759,188 A | 6/1998 | Yoon |
| 5,766,217 A | 6/1998 | Christy |
| 5,776,150 A | 7/1998 | Nolan et al. |
| 5,782,845 A | 7/1998 | Shewchuk |
| D397,218 S | 8/1998 | Cadaver |
| 5,807,276 A | 9/1998 | Russin |
| 5,810,861 A | 9/1998 | Gaber |
| 5,817,112 A | 10/1998 | Christoudias |
| 6,030,391 A | 2/2000 | Brainard et al. |
| 6,035,967 A | 3/2000 | Maeda |
| 6,036,700 A | 3/2000 | Stefanchik et al. |
| 6,200,327 B1 | 3/2001 | Assal |
| 6,347,816 B1 | 2/2002 | Donaho |
| 6,638,286 B1 | 10/2003 | Burbank et al. |
| 6,746,471 B2 | 6/2004 | Mortier et al. |
| 6,749,615 B2 | 6/2004 | Burdulis et al. |
| 6,770,084 B1 | 8/2004 | Bain et al. |
| 6,835,193 B2 | 12/2004 | Epstein et al. |
| 6,936,024 B1 | 8/2005 | Houser |
| 7,101,378 B2 | 9/2006 | Salameh et al. |
| 7,198,626 B2 | 4/2007 | Lee et al. |
| 7,264,623 B2 | 9/2007 | Harris, Jr. et al. |
| 7,322,939 B2 | 1/2008 | Burbank et al. |
| 7,615,062 B2 | 11/2009 | Deland |
| 7,771,441 B2 | 8/2010 | Cerundolo |
| 7,918,868 B2 | 4/2011 | Marshall et al. |
| 7,955,341 B2 | 6/2011 | Cerundolo |
| 8,353,920 B2 | 1/2013 | Mikkaichi |
| 9,226,748 B2 * | 1/2016 | Levine ............. A61B 17/0485 |
| 9,622,741 B2 * | 4/2017 | Levine ............. A61B 17/0482 |
| 2001/0025171 A1 | 9/2001 | Mortier et al. |
| 2002/0198544 A1 | 12/2002 | Uflacker |
| 2004/0102809 A1 | 5/2004 | Anderson |
| 2004/0133216 A1 | 7/2004 | Wulc et al. |
| 2004/0267270 A1 | 12/2004 | Jacobs et al. |
| 2005/0021055 A1 | 1/2005 | Toubia et al. |
| 2005/0261581 A1 | 11/2005 | Hughes et al. |
| 2006/0004409 A1 | 1/2006 | Nobis et al. |
| 2006/0004410 A1 | 1/2006 | Nobis et al. |
| 2006/0025819 A1 | 2/2006 | Nobis et al. |
| 2006/0069398 A1 | 3/2006 | Suzuki et al. |
| 2006/0217762 A1 | 9/2006 | Maahs et al. |
| 2006/0282100 A1 | 12/2006 | Pasricha et al. |
| 2007/0118174 A1 | 5/2007 | Chu |
| 2007/0179509 A1 | 8/2007 | Nagata et al. |
| 2007/0293876 A1 | 12/2007 | Abe et al. |
| 2008/0082113 A1 | 4/2008 | Bishop et al. |
| 2008/0172085 A1 | 7/2008 | Chiu et al. |
| 2008/0269782 A1 | 10/2008 | Stefanchik et al. |
| 2008/0294185 A1 | 11/2008 | Blomdahl et al. |
| 2009/0062817 A1 | 3/2009 | Suzuki et al. |
| 2009/0082797 A1 | 3/2009 | Fung et al. |
| 2009/0082805 A1 | 3/2009 | Kaiser et al. |
| 2009/0216251 A1 | 8/2009 | Levine et al. |
| 2009/0216268 A1 | 8/2009 | Panter |
| 2010/0137679 A1 | 6/2010 | Lashinski et al. |
| 2010/0198235 A1 | 8/2010 | Pierce et al. |
| 2010/0331612 A1 * | 12/2010 | Lashinski .......... A61B 17/0401 600/37 |
| 2012/0143225 A1 | 6/2012 | Chin et al. |
| 2014/0275750 A1 | 9/2014 | Levine |

FOREIGN PATENT DOCUMENTS

| | | |
|---|---|---|
| EP | 1862125 A2 | 12/2007 |
| JP | S63-40559 A | 2/1988 |
| JP | H06-74146 U | 10/1994 |
| JP | H08-215200 A | 8/1996 |
| JP | H09-248305 A | 9/1997 |
| JP | H10-216161 A | 8/1998 |
| JP | H11-042233 A | 2/1999 |
| JP | 2001-198131 A | 7/2001 |
| JP | 2002-028164 A | 1/2002 |
| JP | 2004-513702 A | 5/2004 |
| JP | 2004-526483 A | 9/2004 |
| JP | 3628597 B2 | 3/2005 |
| JP | 2007-151615 A | 6/2007 |
| JP | 2007-167500 A | 7/2007 |
| JP | 2007524425 A | 8/2007 |
| JP | 2007-296319 A | 11/2007 |
| JP | 2010534510 A | 11/2010 |
| JP | 2012522572 A | 9/2012 |
| KR | 20070093256 A | 9/2007 |
| WO | 9406357 A1 | 3/1994 |
| WO | 9531149 A1 | 11/1995 |
| WO | 9602197 A1 | 2/1996 |
| WO | 9835616 A1 | 8/1998 |
| WO | 0193656 A2 | 12/2001 |
| WO | 2002039905 A1 | 5/2002 |
| WO | 03077771 A1 | 9/2003 |
| WO | 2005096956 A1 | 10/2005 |
| WO | 2006047563 A2 | 5/2006 |
| WO | 2007073931 A1 | 7/2007 |
| WO | 2008042992 A1 | 4/2008 |
| WO | 2008070691 A2 | 6/2008 |
| WO | 2009045248 A1 | 4/2009 |
| WO | 2012034131 A2 | 3/2012 |
| WO | 2013119592 A1 | 8/2013 |

OTHER PUBLICATIONS

Office Action dated Mar. 8, 2016 in MX Application No. MX/a/2010/001019 (translation only).

(56) References Cited

OTHER PUBLICATIONS

Office Action dated May 2, 2016 in U.S. Appl. No. 12/452,743 by Levine.
EP Extended Search Report in EP Application No. 10759139.8 dated Jul. 15, 2013, 8 pages.
Office Action dated Nov. 13, 2012 in IL Application No. 203421.
Int'l Search Report and Written Opinion dated Nov. 9, 2010 in Int'l Application No. PCT/US2010/000891.
Int'l Preliminary Report on Patentability dated Oct. 13, 2011 in Int'l Application No. PCT/US2010/000891.
Int'l Search Report and Written Opinion dated Mar. 3, 2009 in Int'l Application No. PCT/US2008/009012.
Int'l Preliminary Report on Patentability dated Feb. 4, 2010 in Int'l Application No. PCT/US2008/009012.
Office Action dated Jan. 14, 2014 in JP Application No. 2012-503414.
Office Action dated Jan. 22, 2013 in JP Application No. 2010-518225.
Partial translation of an Office Action dated Mar. 11, 2014 in MX Application No. MX/a/2010/001019.
Office Action dated Jul. 31, 2014 in AU Application No. 2010232964.
Office Action dated Jul. 31, 2014 in AU Application No. 2013204680.
Office Action dated Aug. 15, 2014 in AU Application No. 2013204057.
Office Action dated Sep. 9, 2014 in U.S. Appl. No. 12/384,326 by Levine.
Int'l Search Report and Written Opinion dated Aug. 28, 2014 in Int'l Application No. PCT/US2014/030533.
Office Action dated Jul. 10, 2014 in CA Application No. 2,694,650.
Office Action dated Oct. 16, 2014 in U.S. Appl. No. 12/452,743 by Levine.
Office Action dated Oct. 1, 2014 in IL Application No. 215256.
English translation of an Office Action dated Oct. 14, 2014 in MX Application No. MX/a/2010/001019.
Office Action dated Oct. 29, 2014 in KR Application No. 10-2010-7003741.
Office Action dated Dec. 18, 2012 in AU Application No. 2008307757.
Office Action dated May 10, 2013 in AU Application No. 2008307757.
Office Action dated Jul. 5, 2012 in U.S. Appl. No. 12/384,326.
Office Action dated Sep. 3, 2013 in U.S. Appl. No. 12/384,326 by Levine.
Office Action dated Feb. 27, 2013 in U.S. Appl. No. 12/452,743 by Levine.
Office Action dated Jul. 30, 2013 in U.S. Appl. No. 12/452,743 by Levine.
Office Action dated Jan. 27, 2015 in JP Application No. 2014-002445.
Int'l Preliminary Report on Patentability dated Feb. 6, 2015 in Int'l Application No. PCT/US2014/030533.
Office Action dated May 29, 2015 in U.S. Appl. No. 12/452,743 by Levine.
Search Report dated Mar. 27, 2015 in EP Applicaiton No. 08836569.7.
Office Action dated May 4, 2015 in IL Application No. 226164.
Office Action dated May 21, 2015 in CA Application No. 2,694,650.
English translation of an Office Action dated in MX Application No. MX/a/2010/001019.
Office Action dated Jun. 3, 2015 in U.S. Appl. No. 12/384,326 by Levine.
Office Action dated Sep. 29, 2015 in JP Application No. 2014-002445.
Office Action dated Nov. 10, 2015 in JP Application No. 2014-250161.
Baumgarten and Wright, "Sliding Knots—Overhand Throw and Duncan Loop", Arthroscopic Knot Tying—An Instruction Manual, Lippincott, Williams & Wilkins, Philadelphia (2005), pp. 32 and 33.
"Knot Tying Illustrations—Easy Slider" and "Knot Tying Illustrations—The Fancy Slider"—Web Publication reviewed Oct. 13, 2010 and "www.utube.com/watch?v=ZJzf1Le00ck" and "www.phoenixsterling.com/IMAGES/Knot%20Tying%20Illustrations.pdf".
McMillan and Caspari, "Arthroscopic Knot-Tying Techniques", An Atlas of Shoulder Arthroscopy, Imhoff, Ticker and Fu, Editors, Martin Dunitz, London (2003), pp. 87 to 95.
Int'l Search Report and Written Opinion dated Oct. 30, 2014 in Int'l Application No. PCT/US2014/024816.
Int'l Preliminary Report on Patentability dated Sep. 24, 2015 in Int'l Application No. PCT/US2014/024816.
Office Action dated Mar. 27, 2018 in JP Application No. 2016-503415.
Extended Search Report dated Feb. 16, 2017 in EP Application No. 14764111.2.

\* cited by examiner

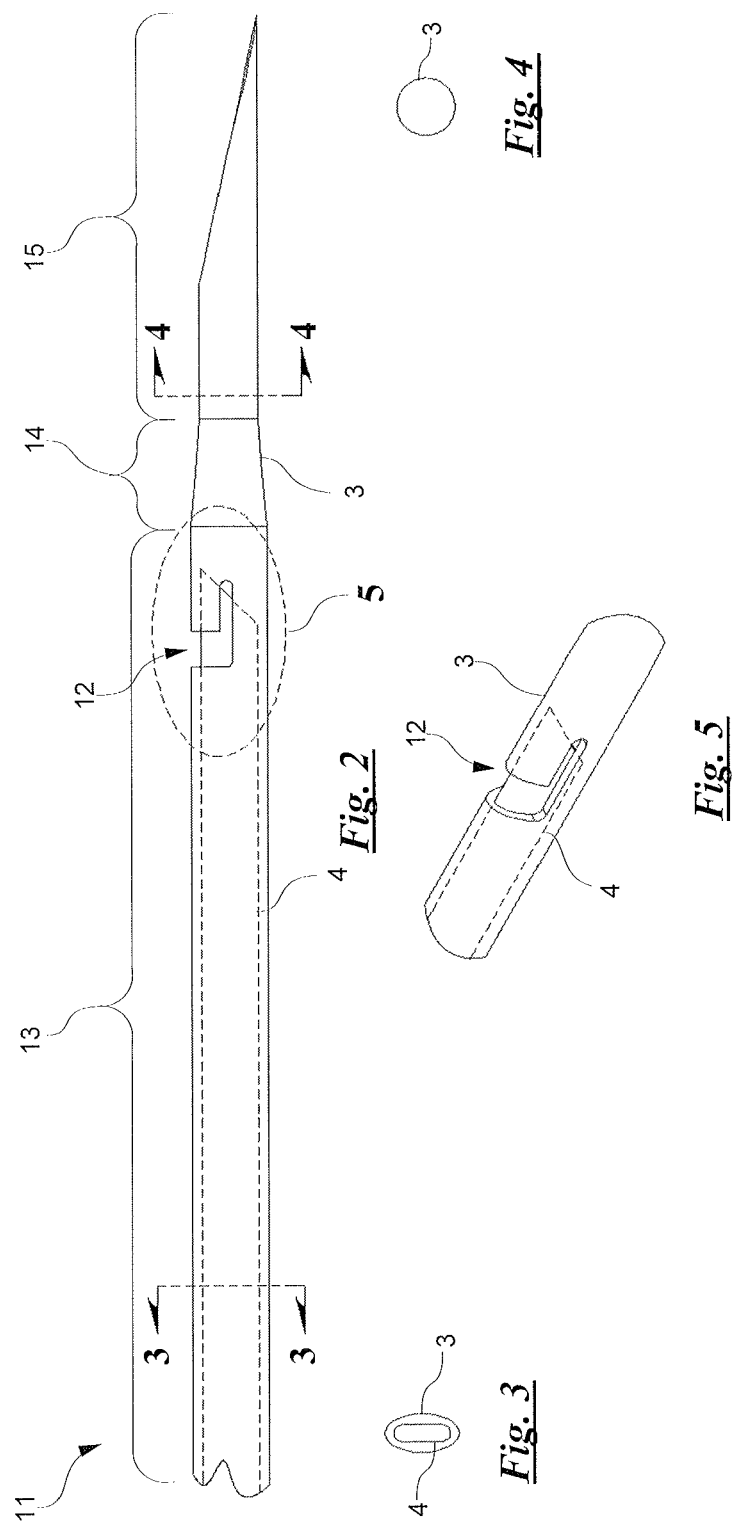

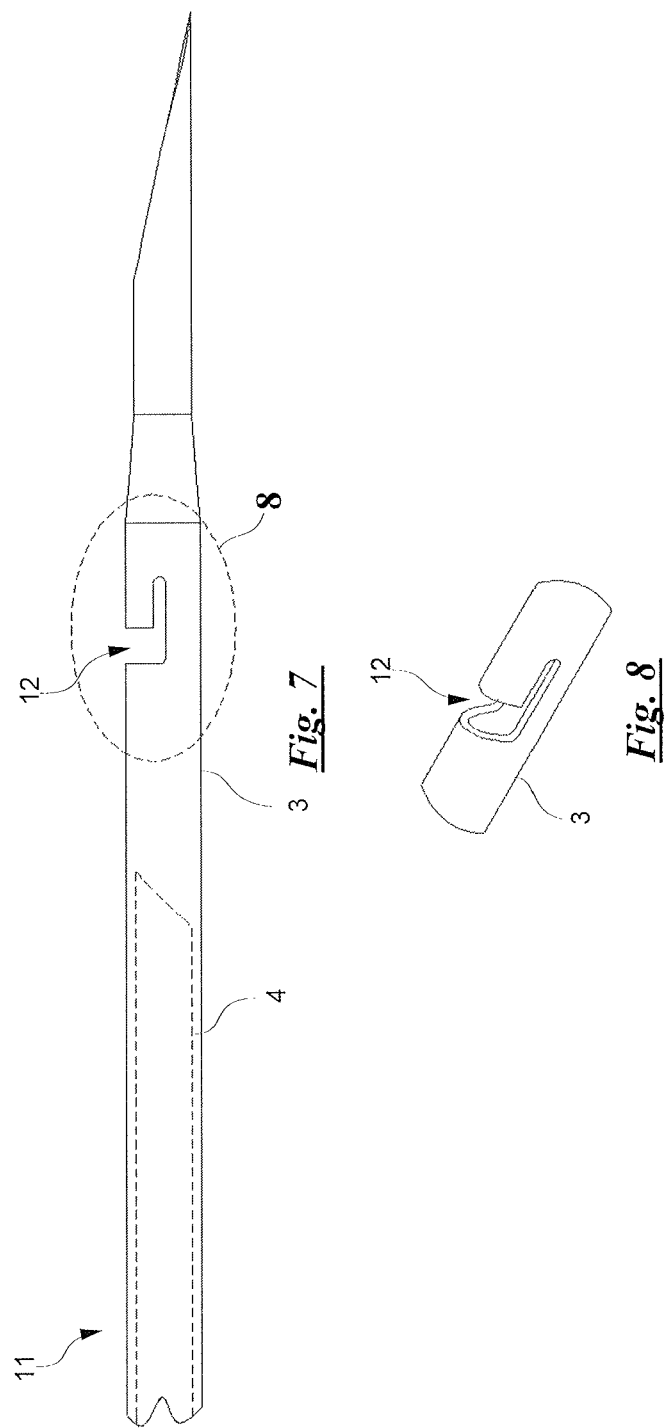

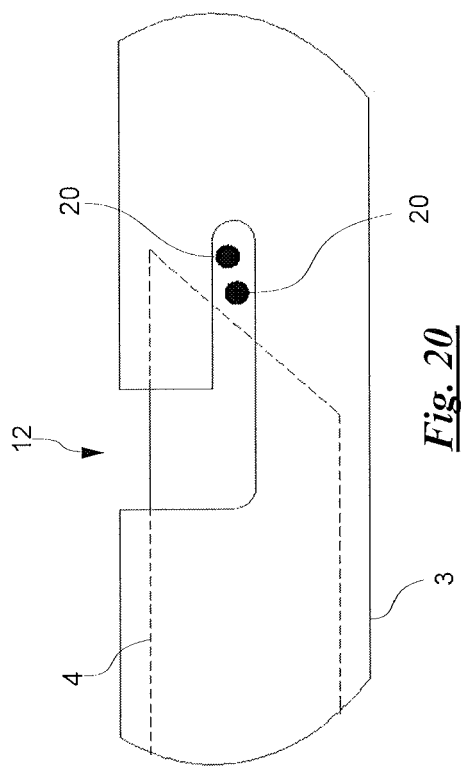

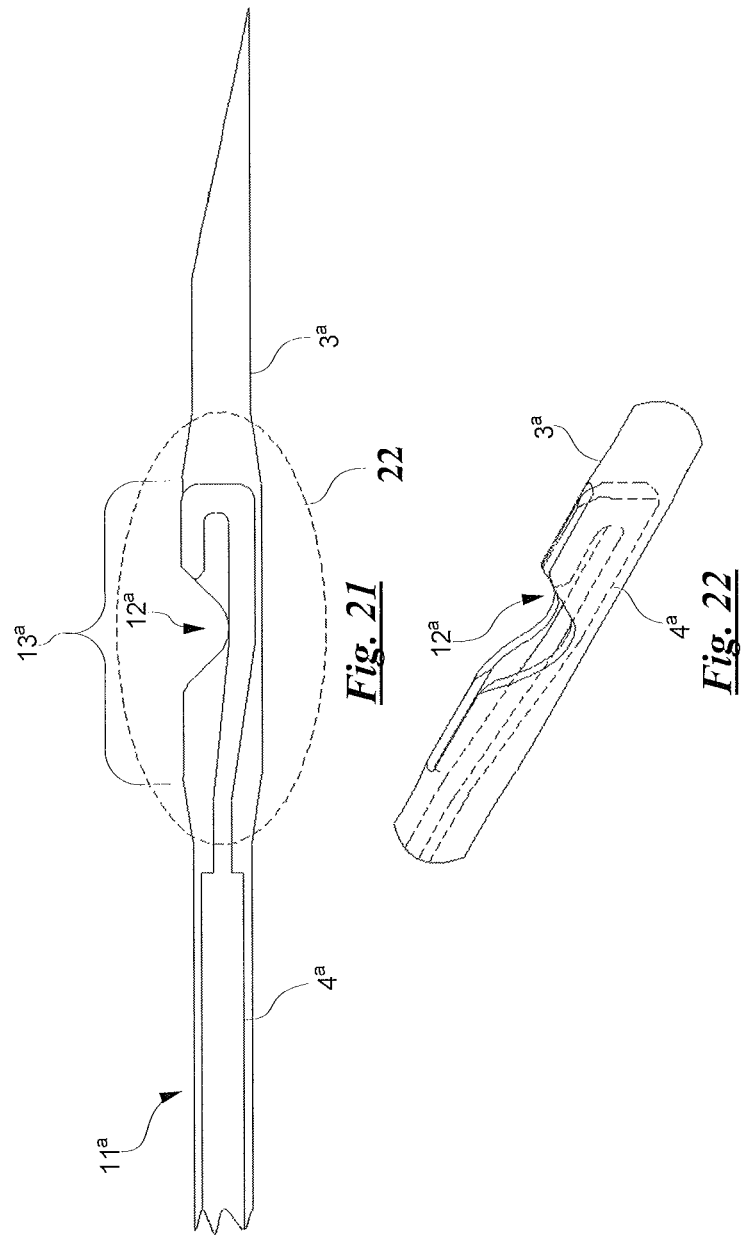

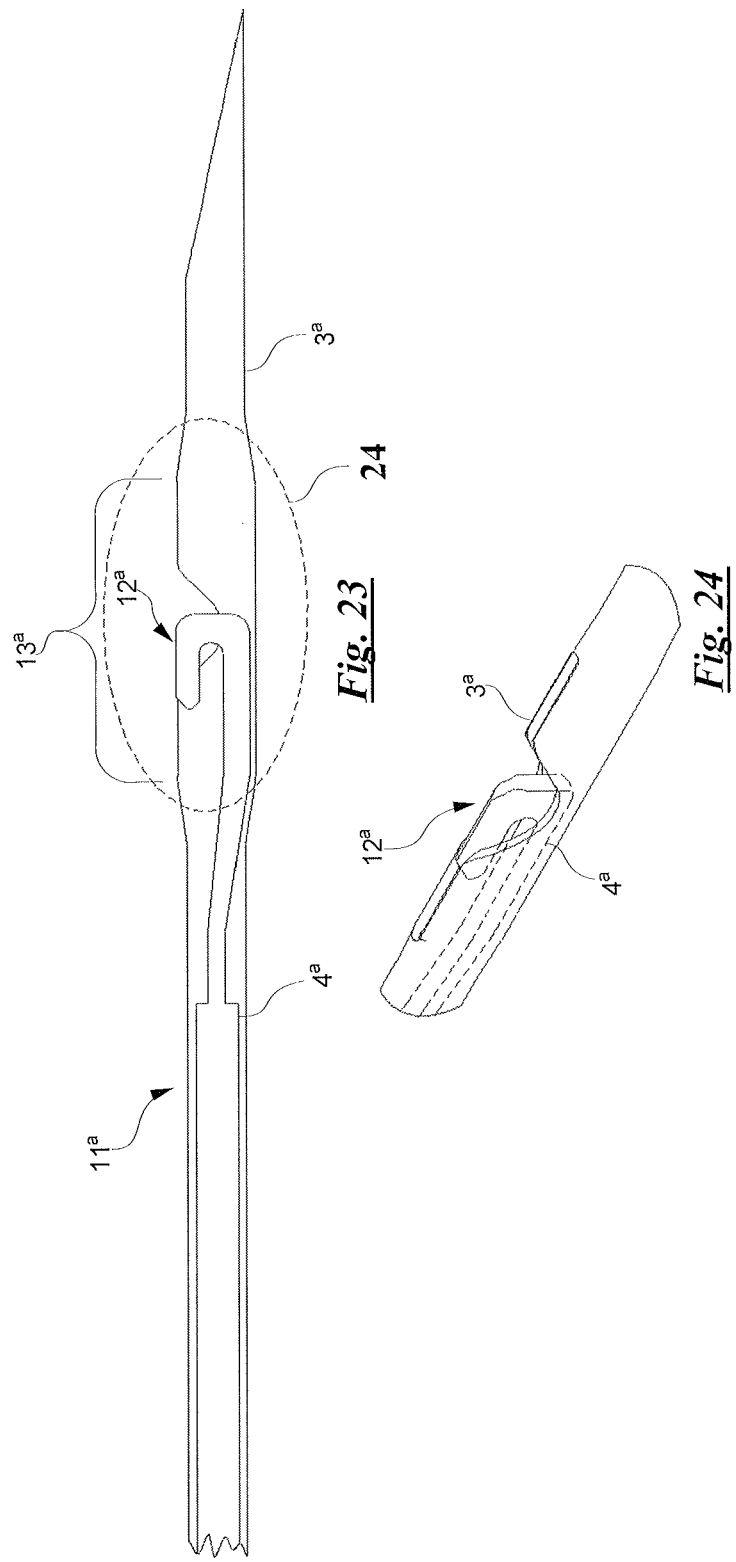

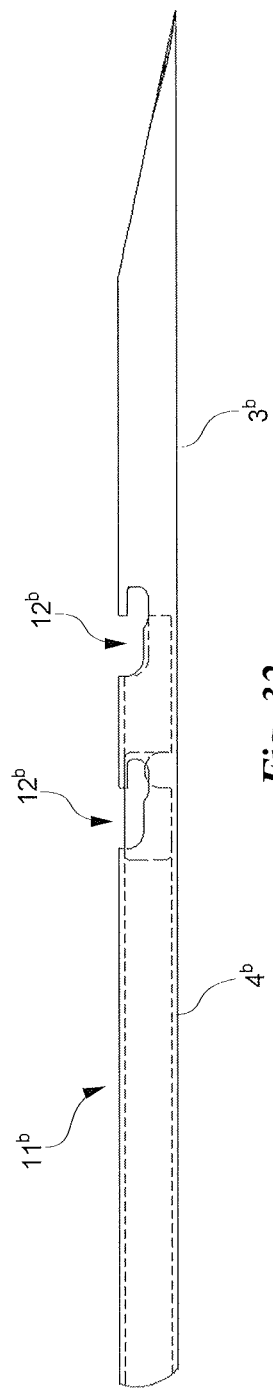

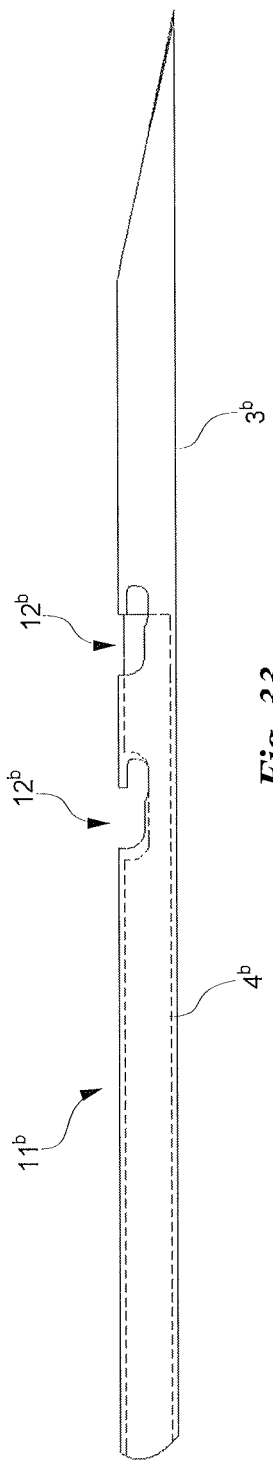

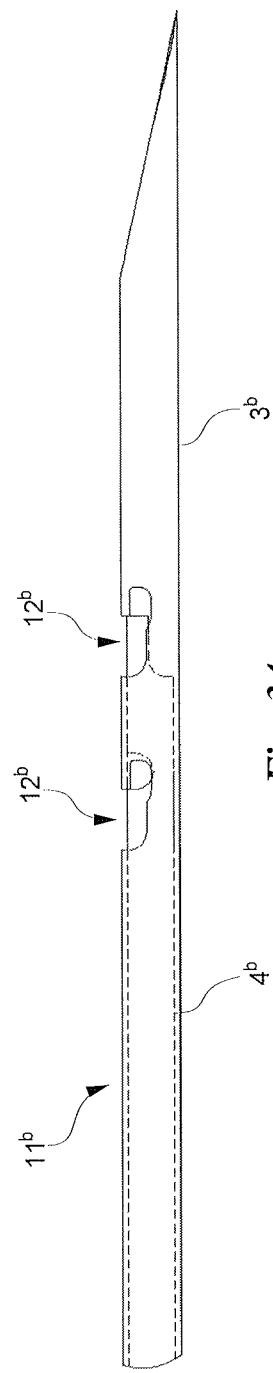

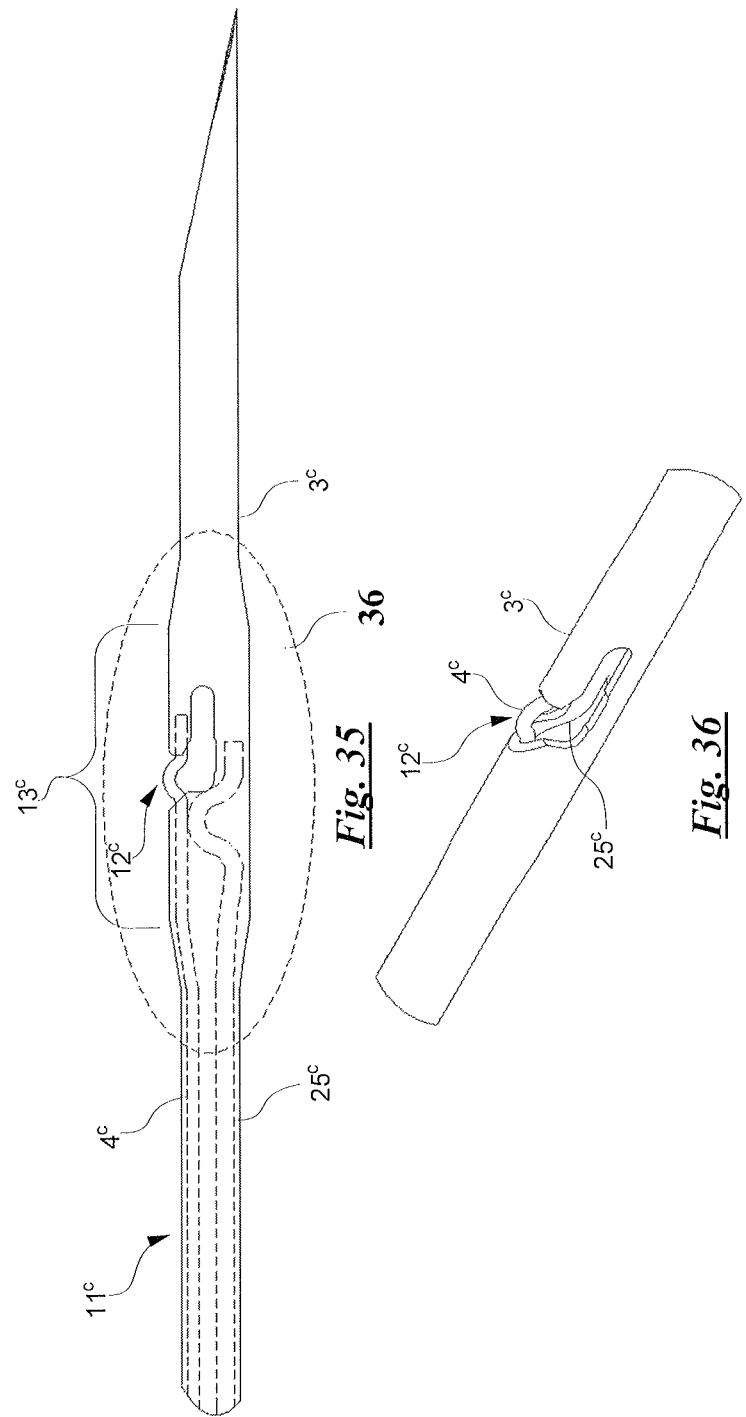

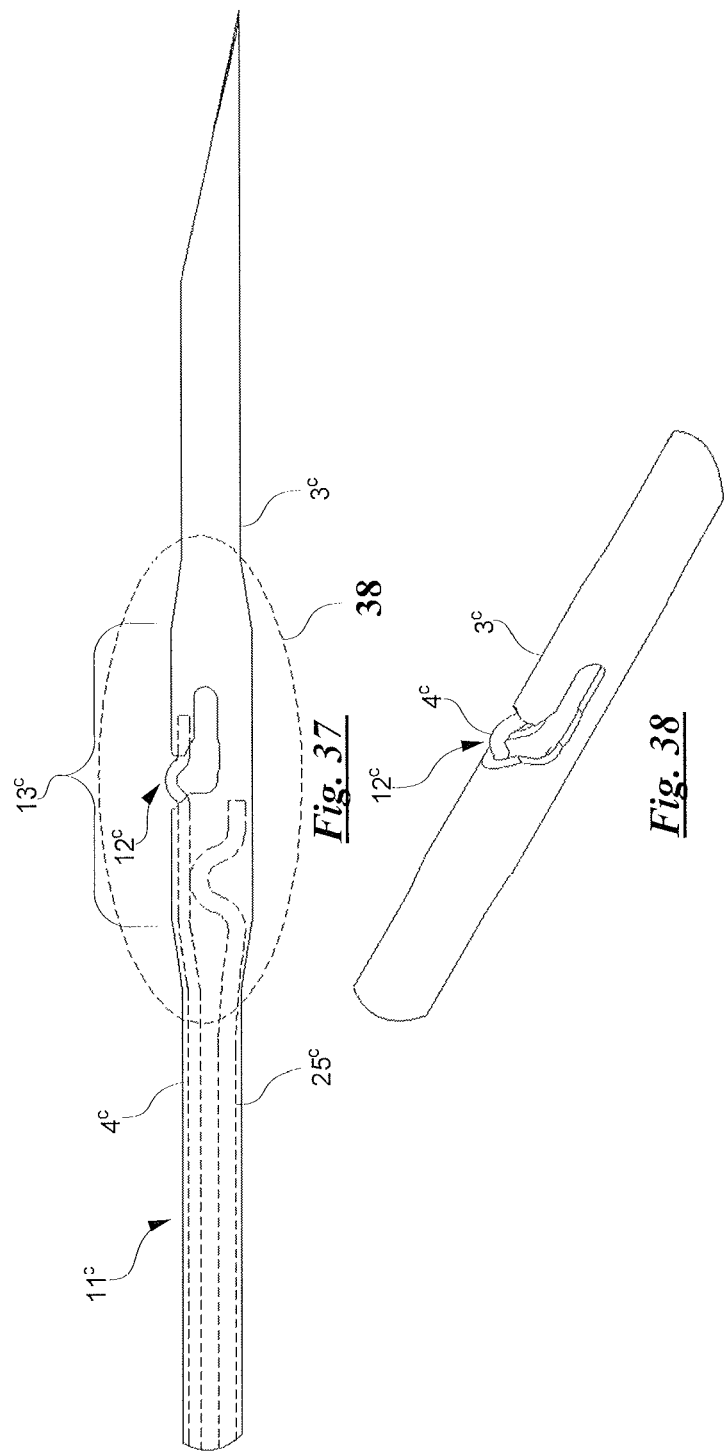

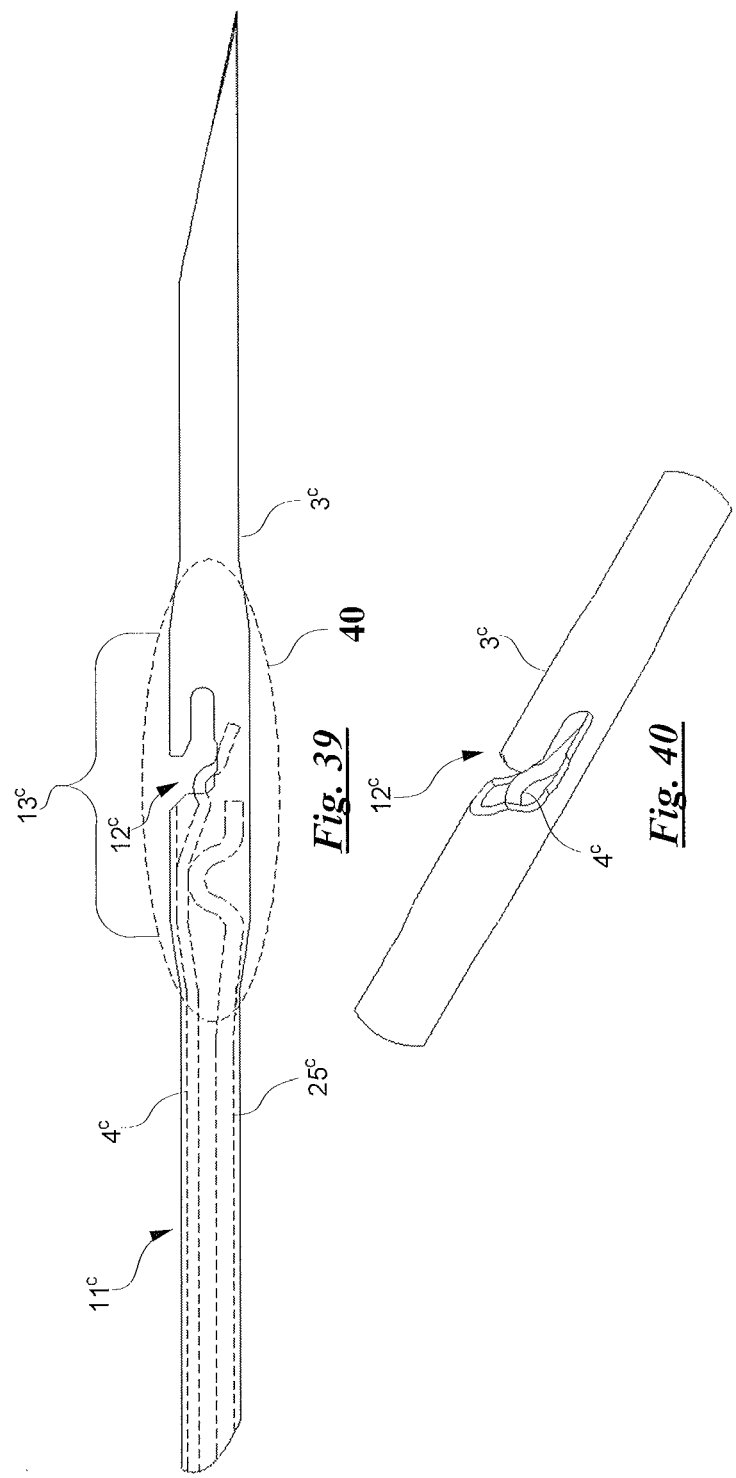

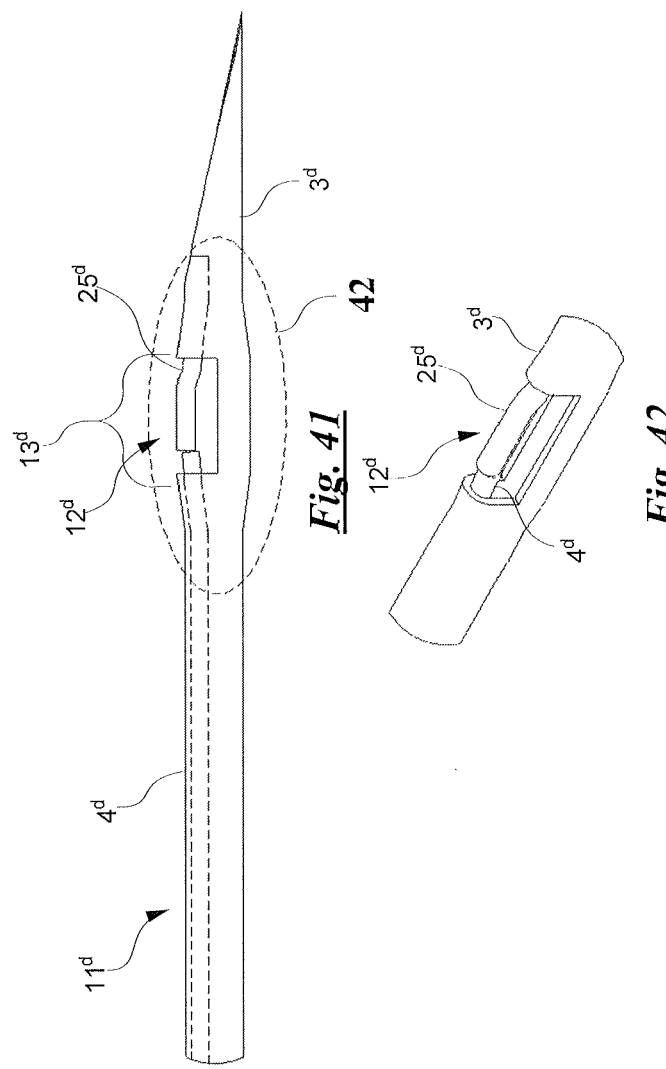

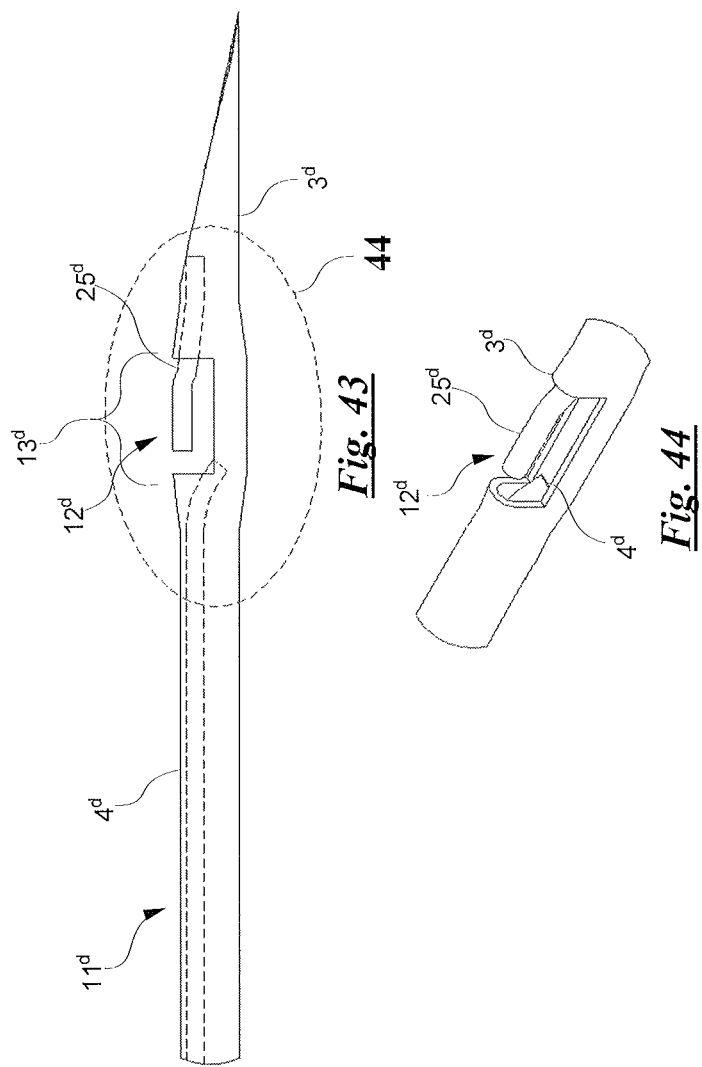

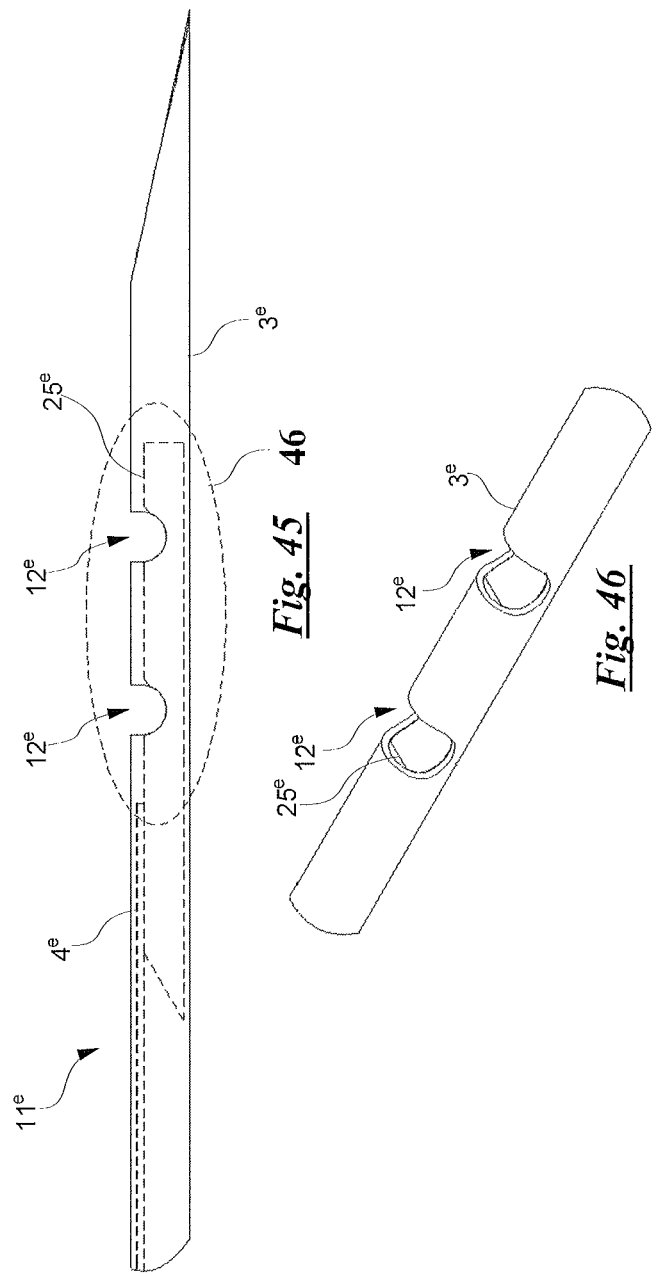

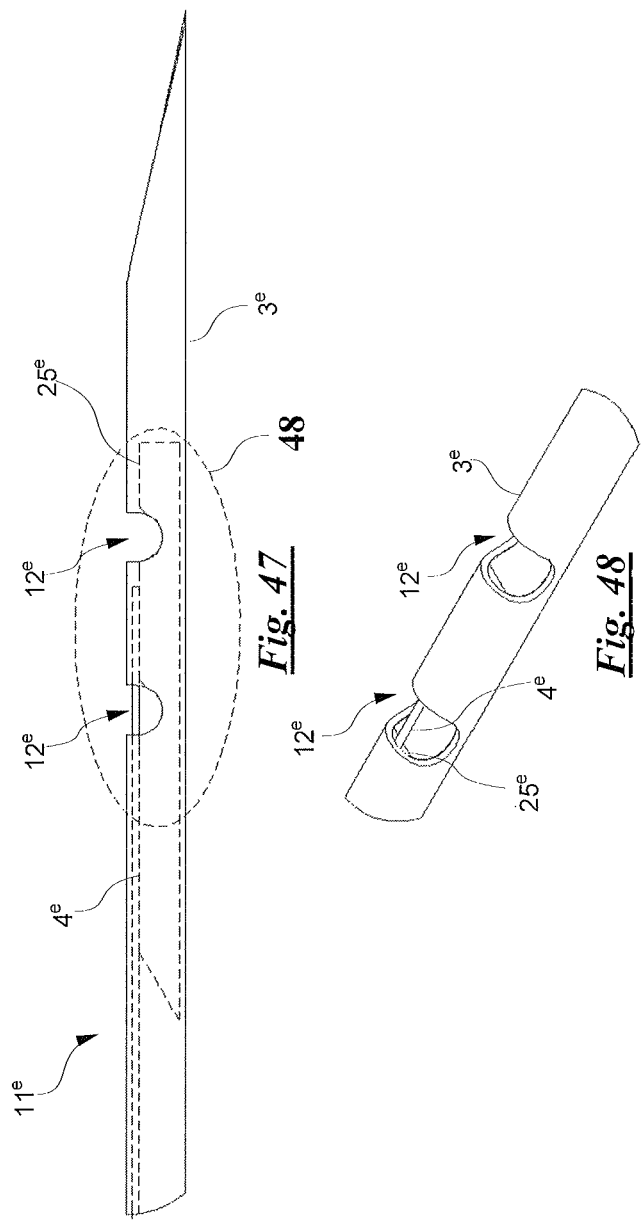

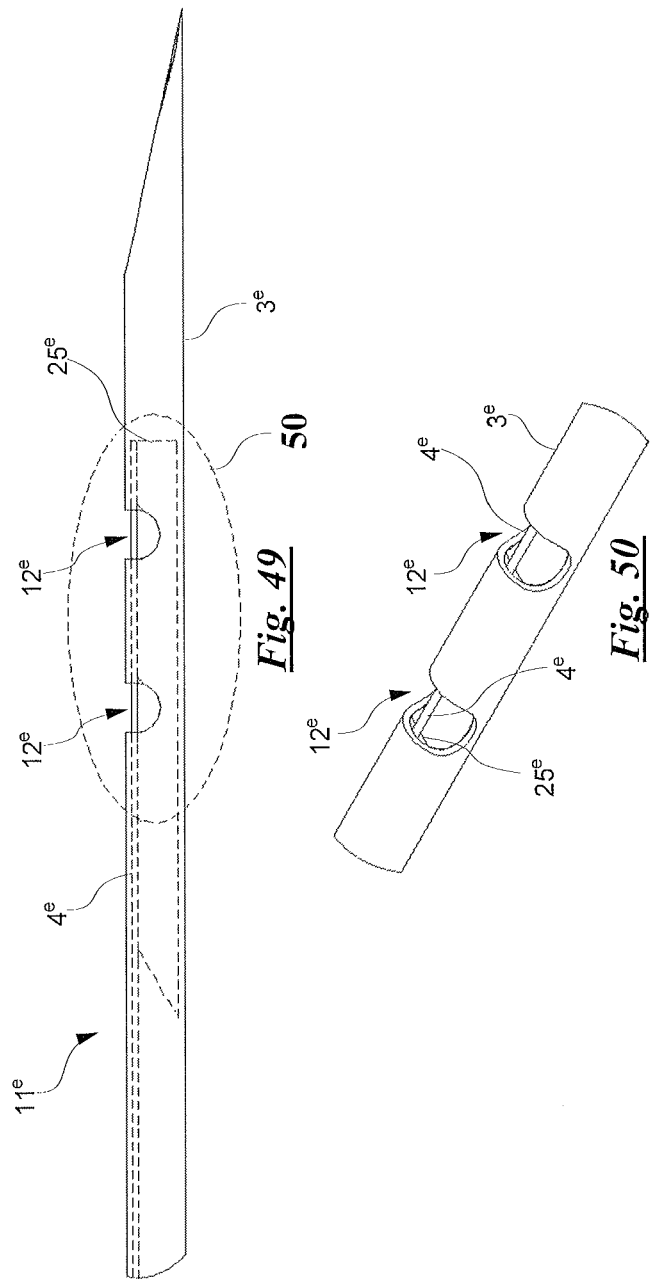

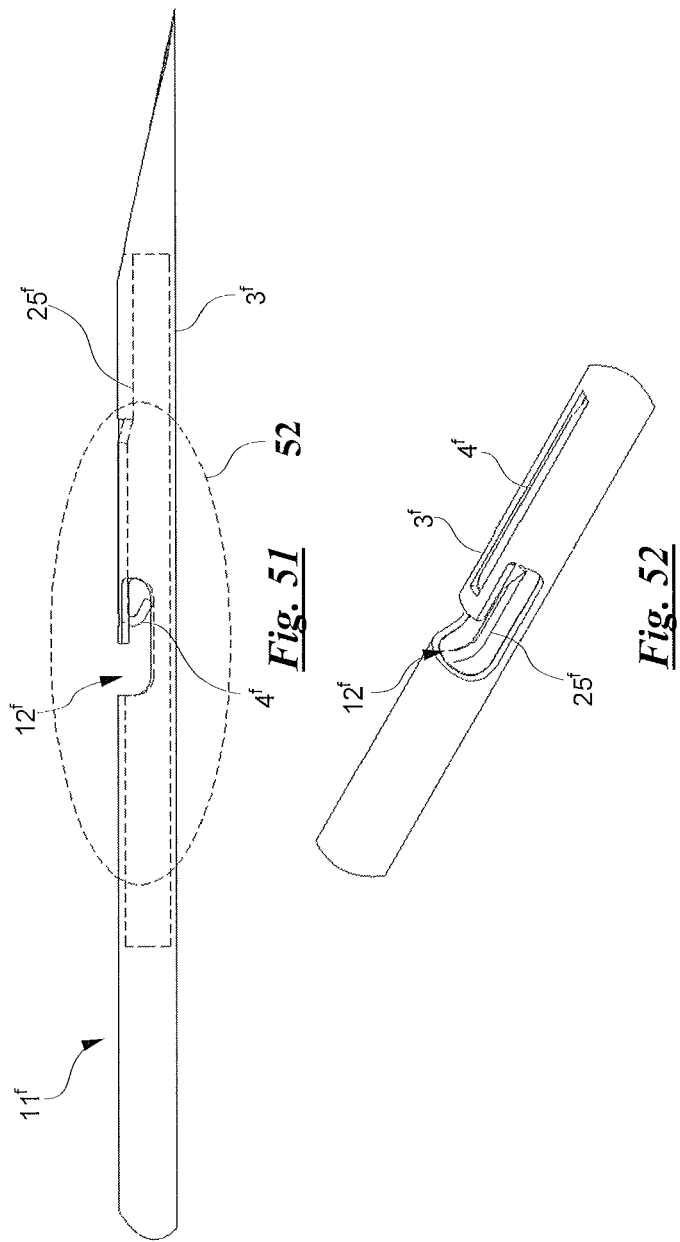

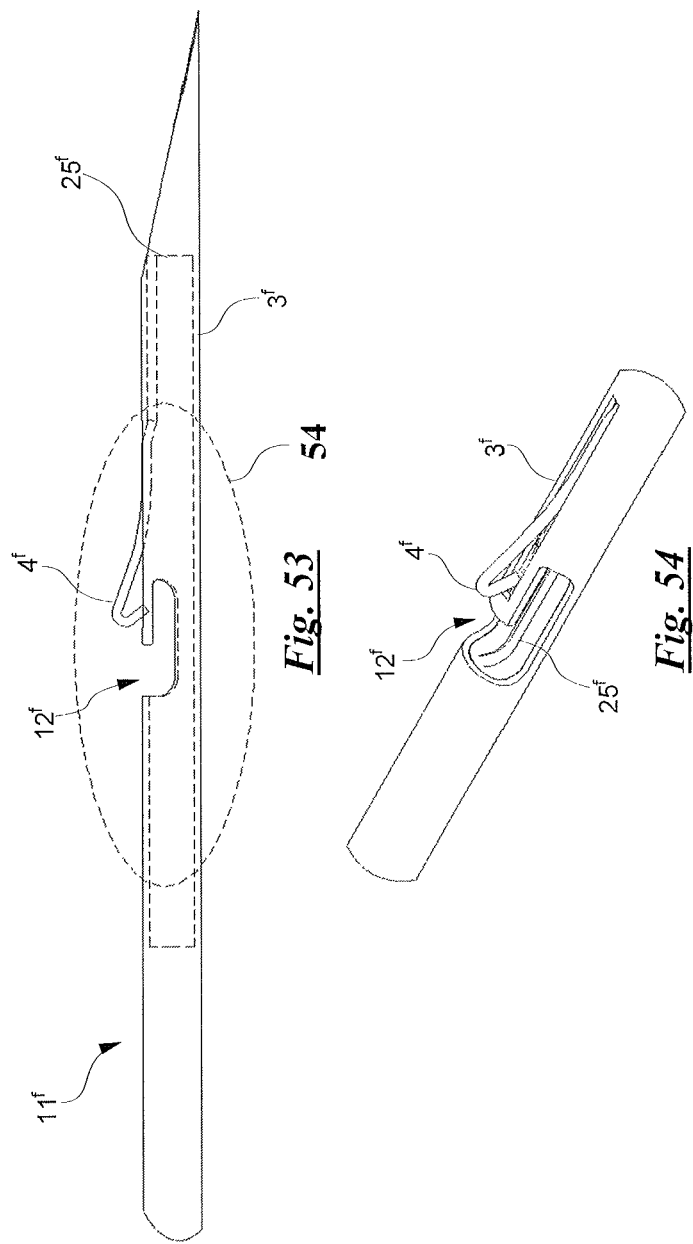

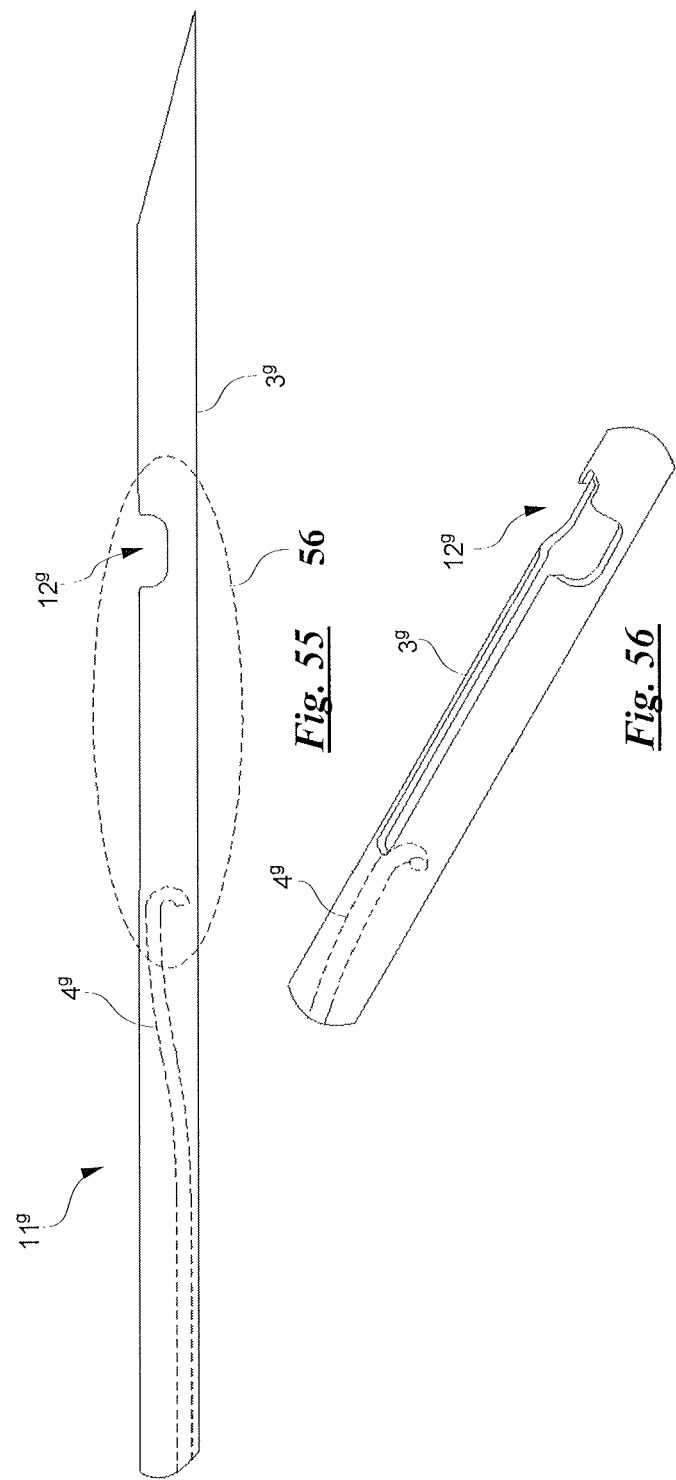

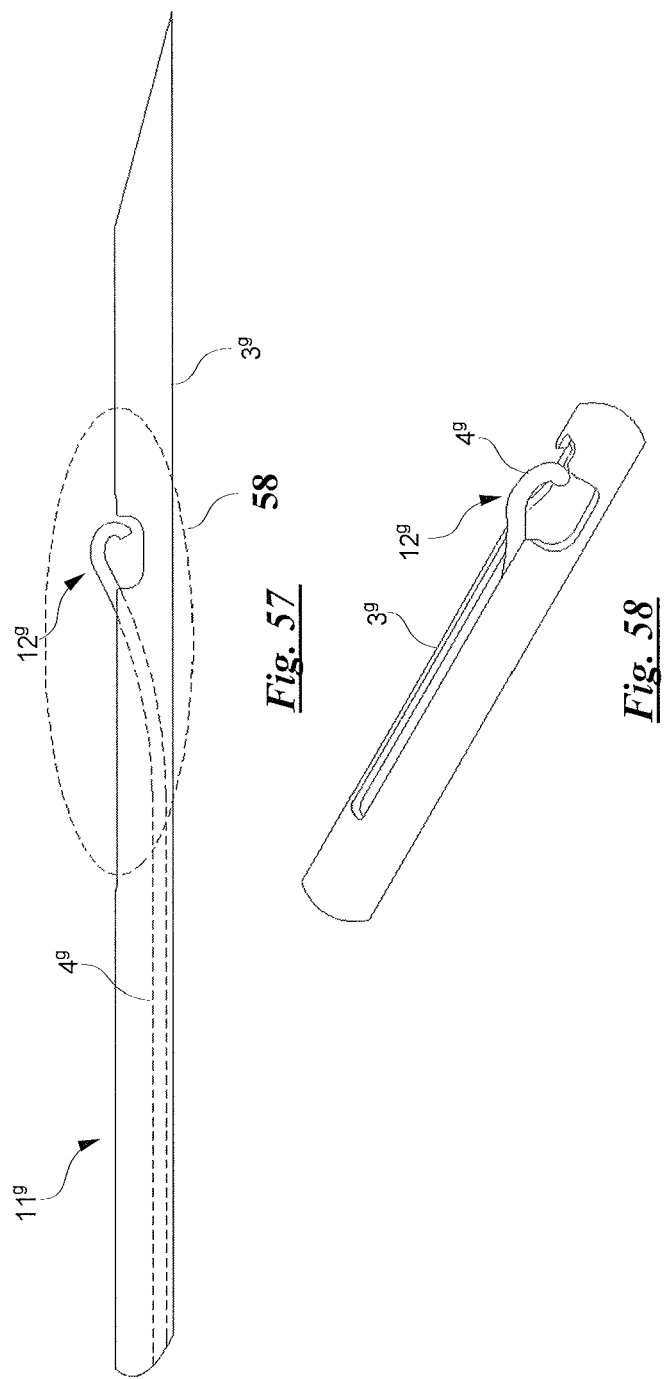

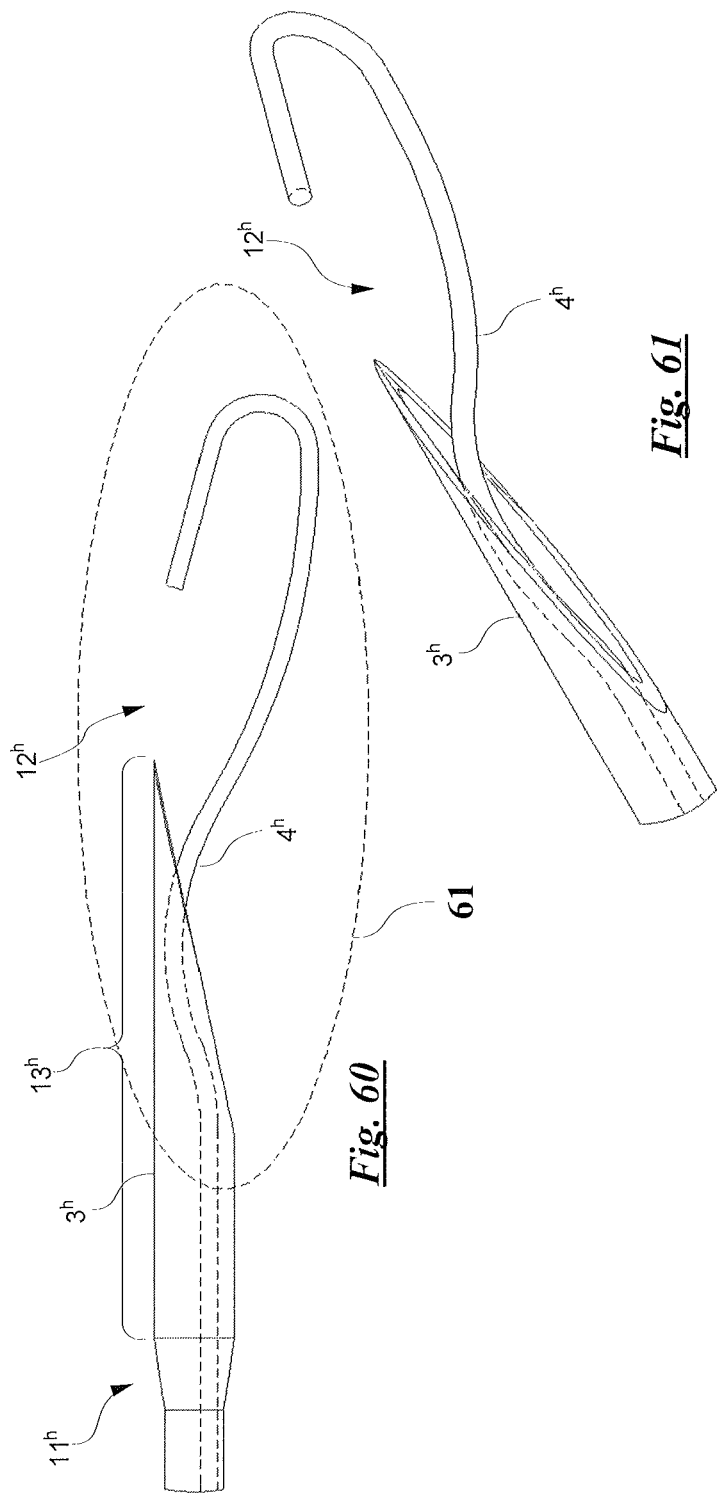

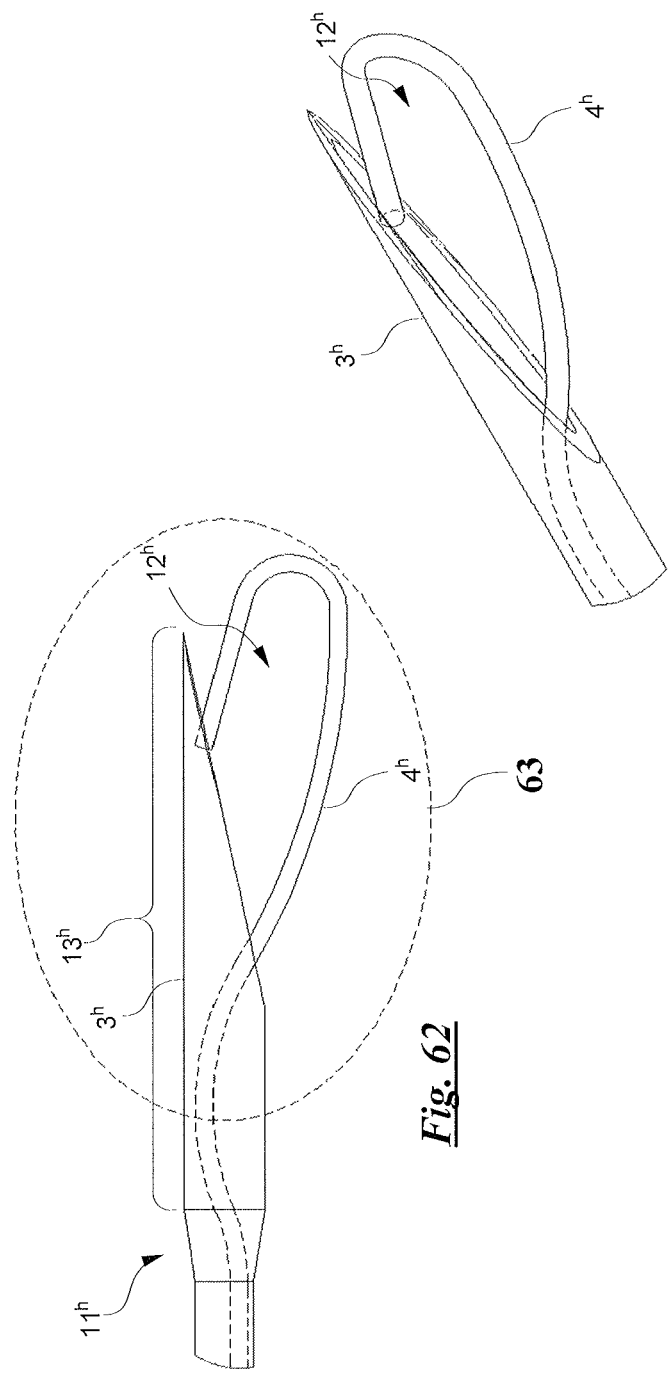

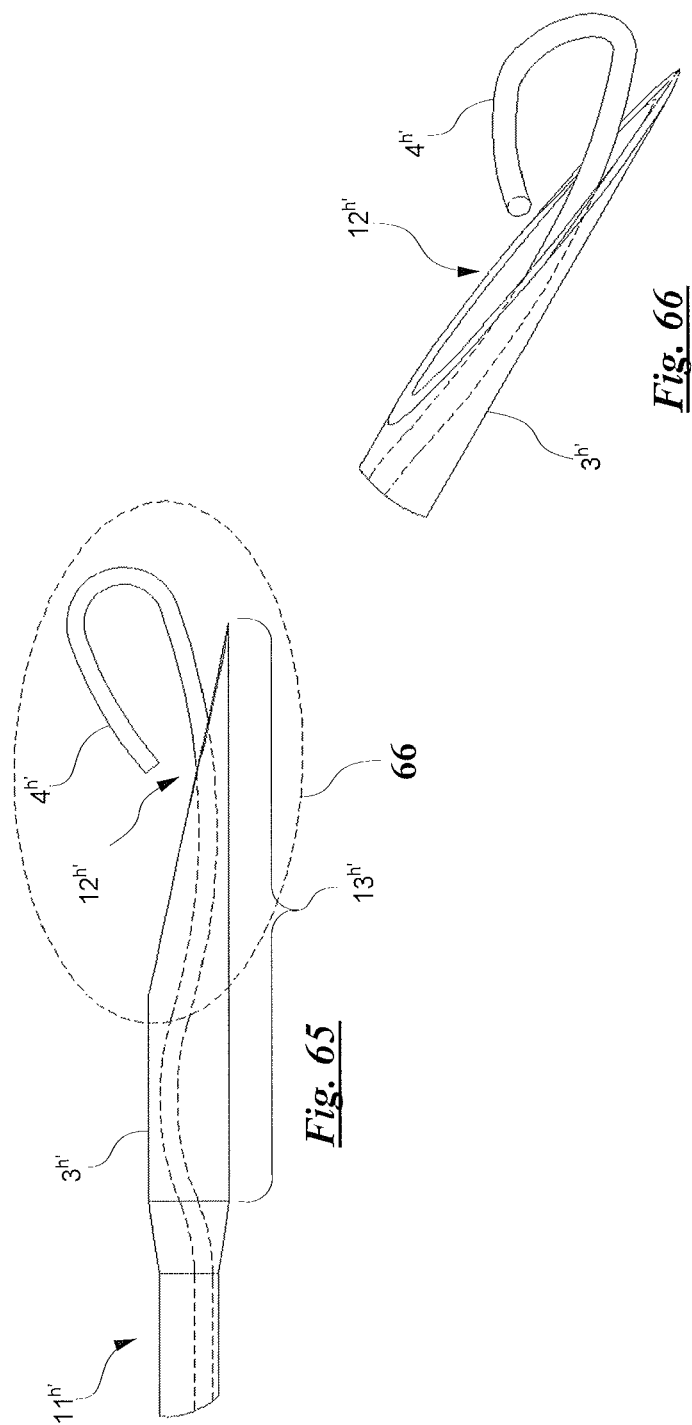

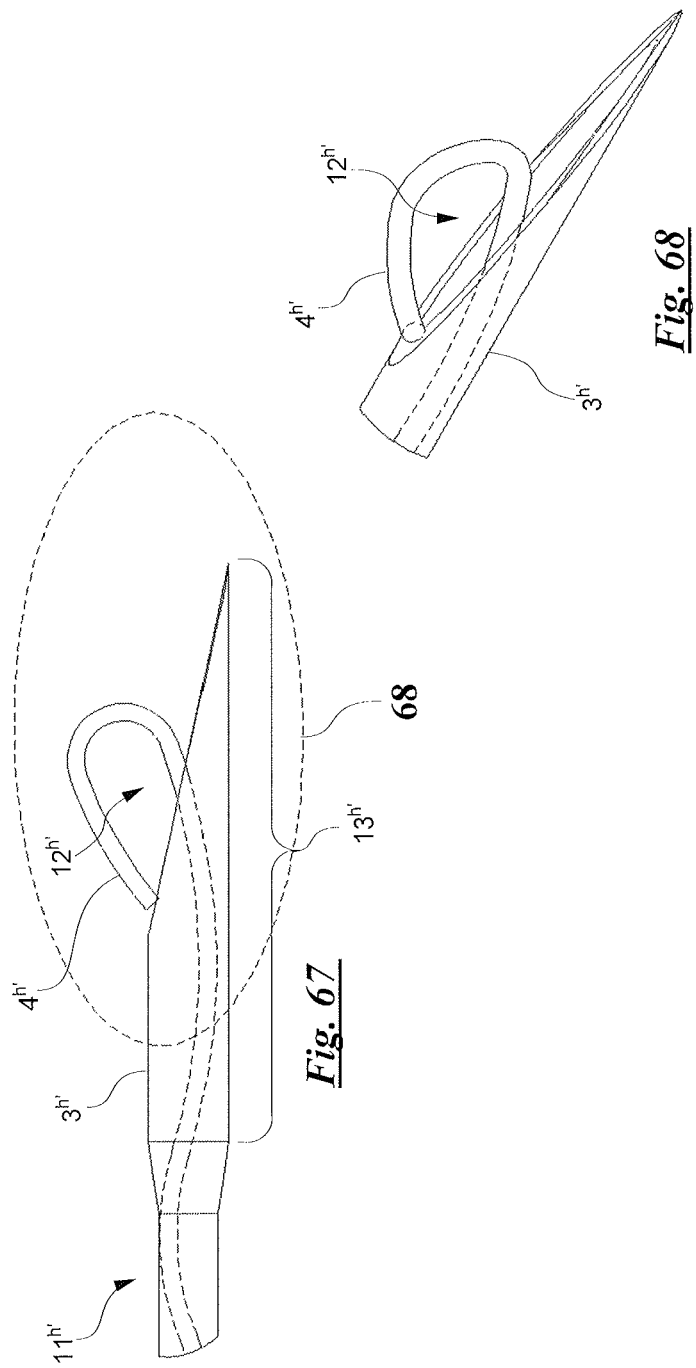

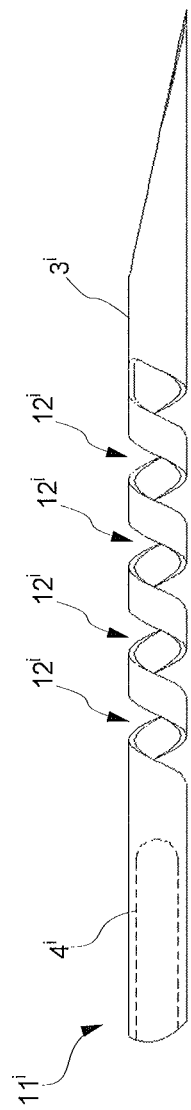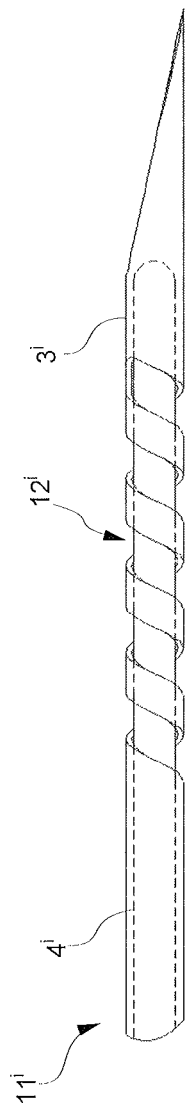

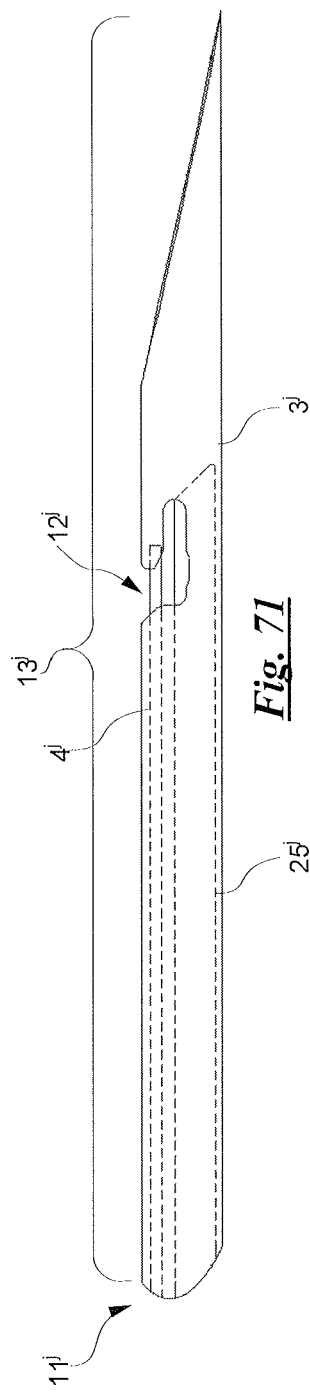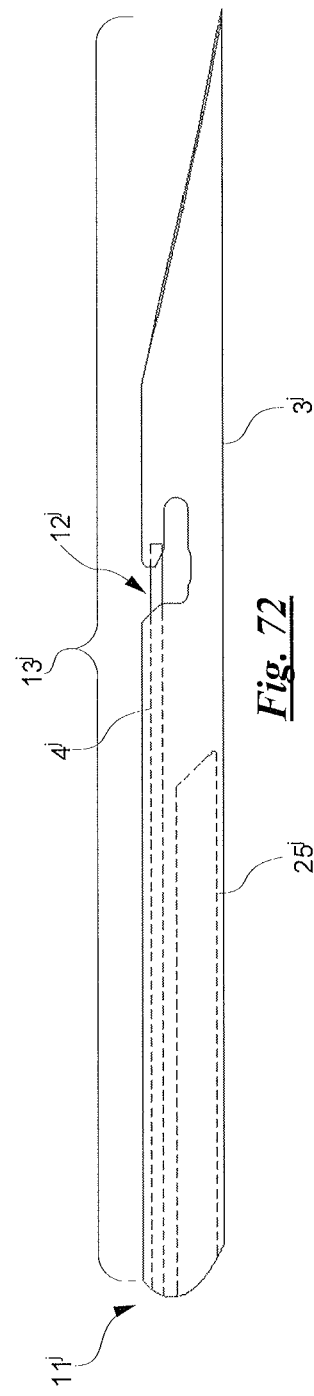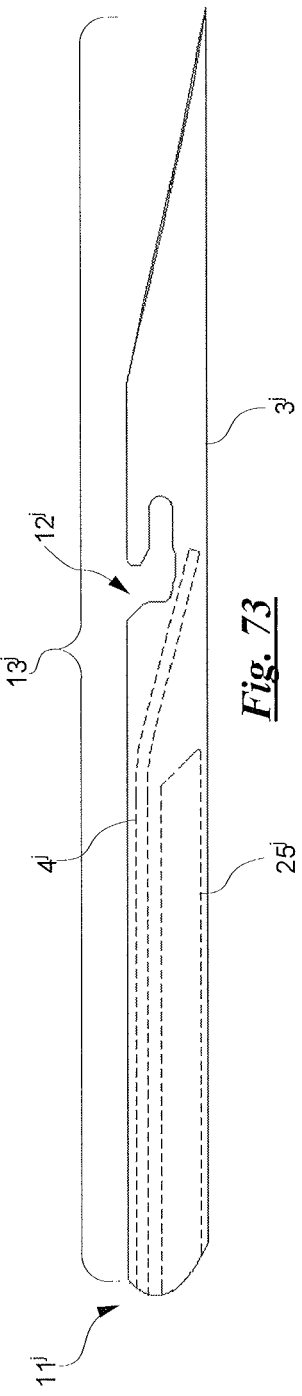

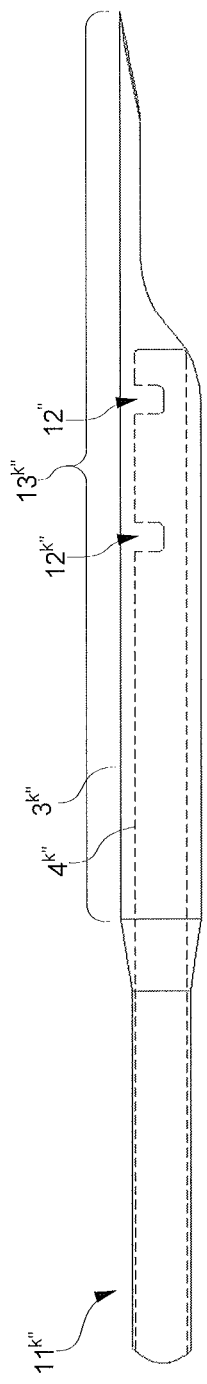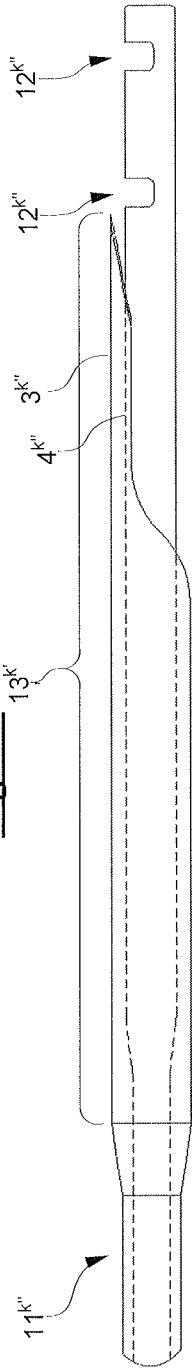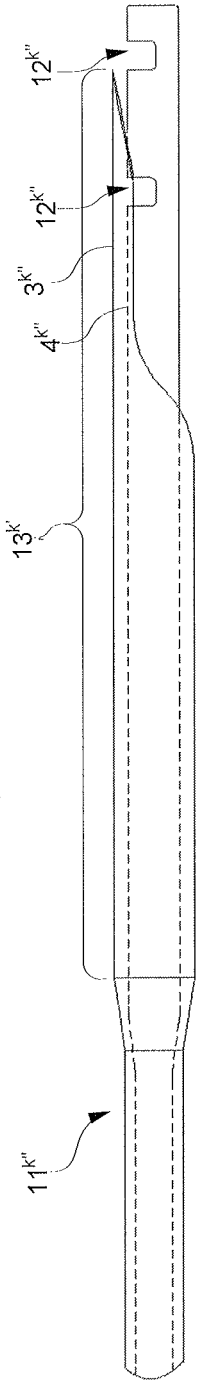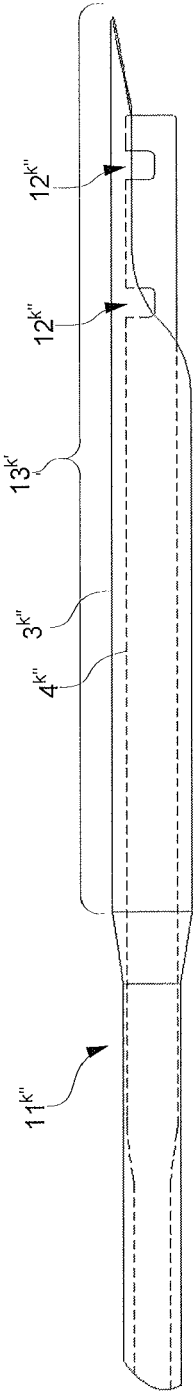

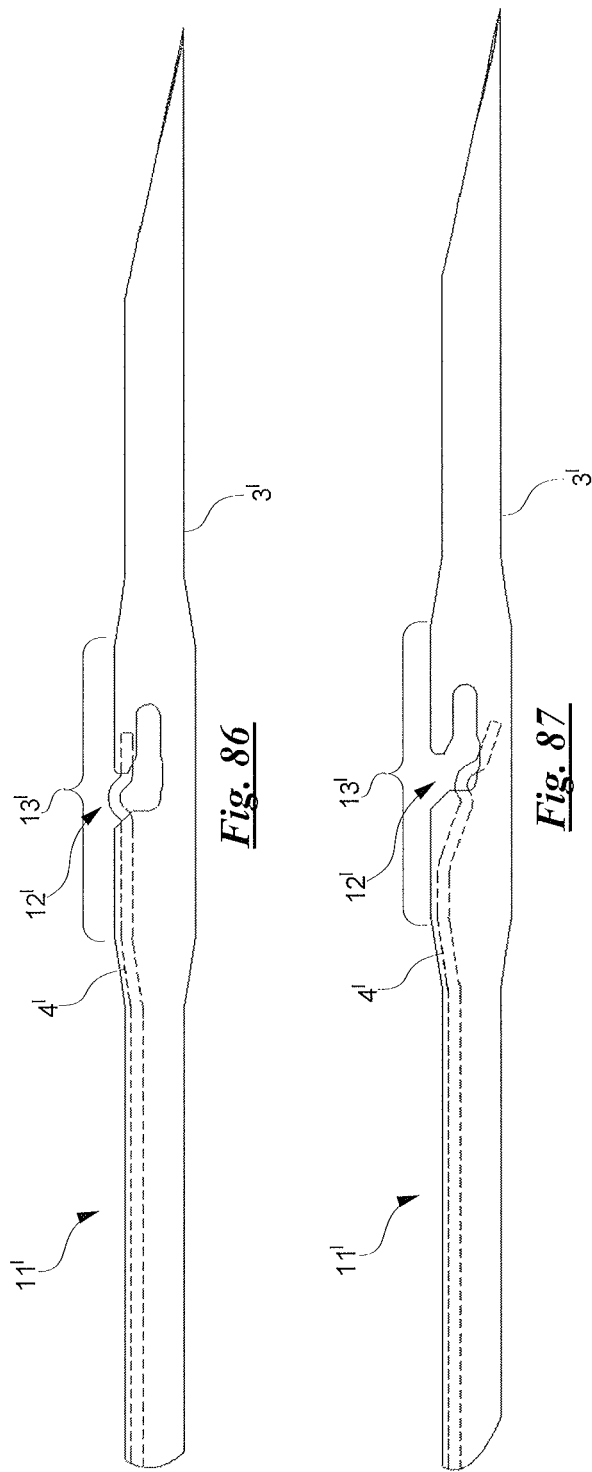

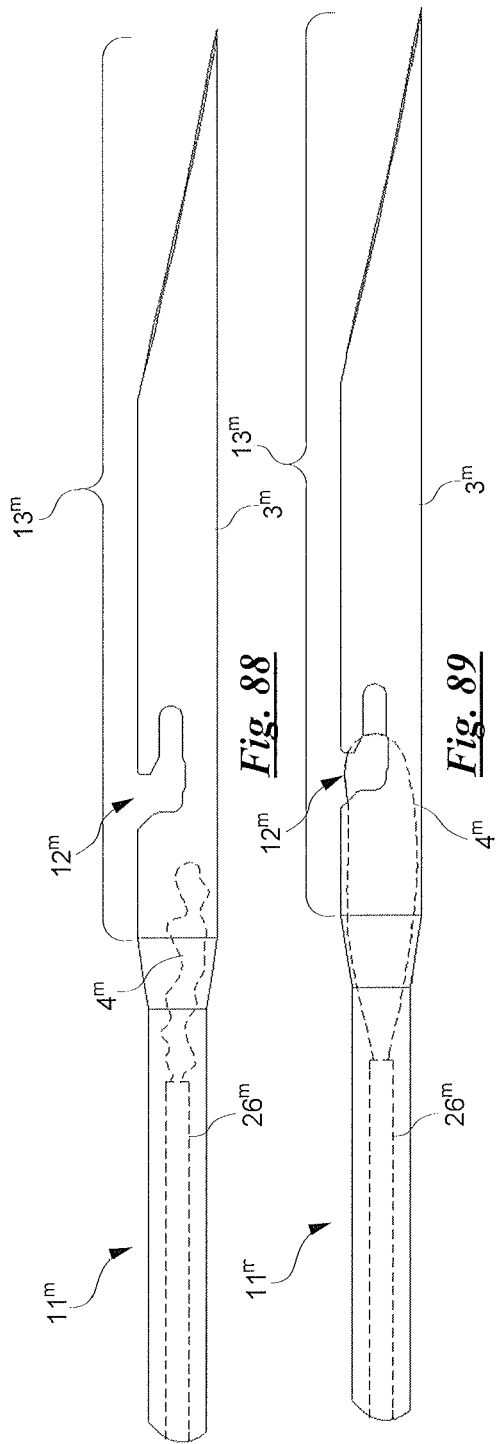

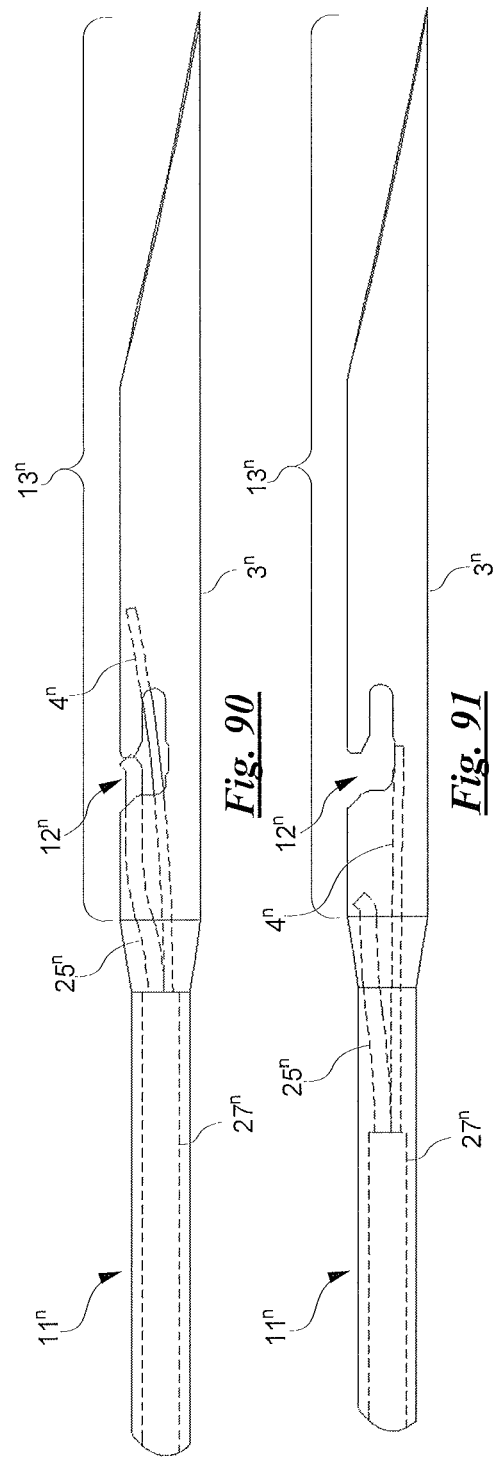

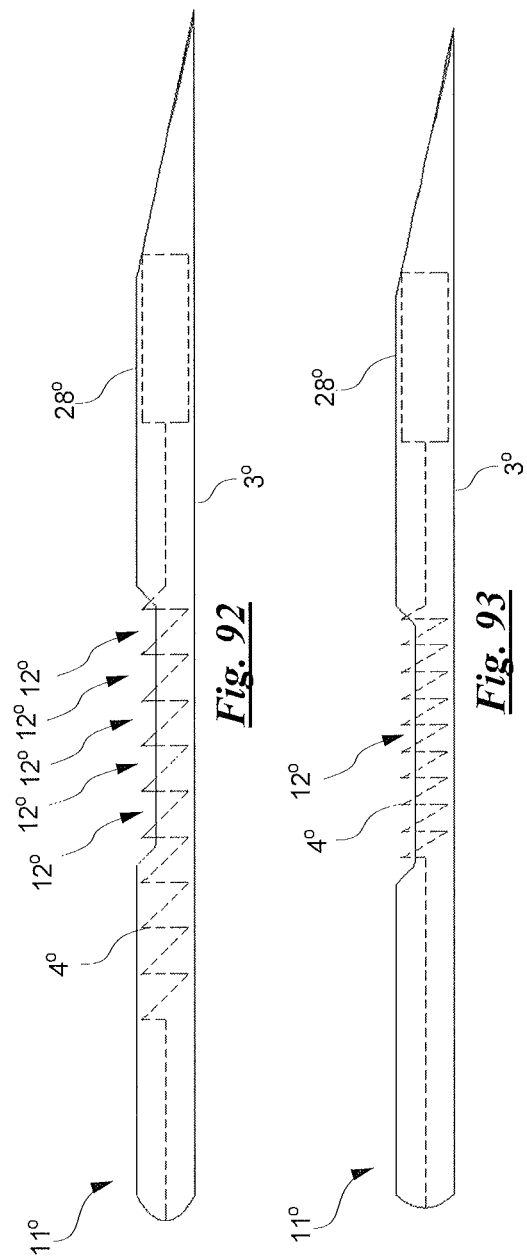

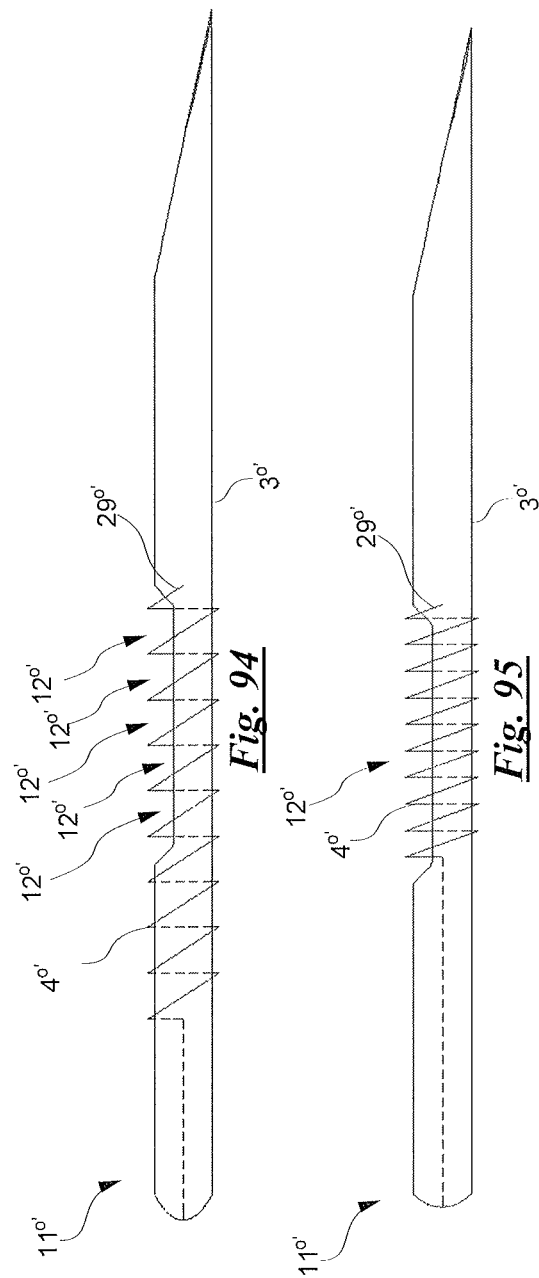

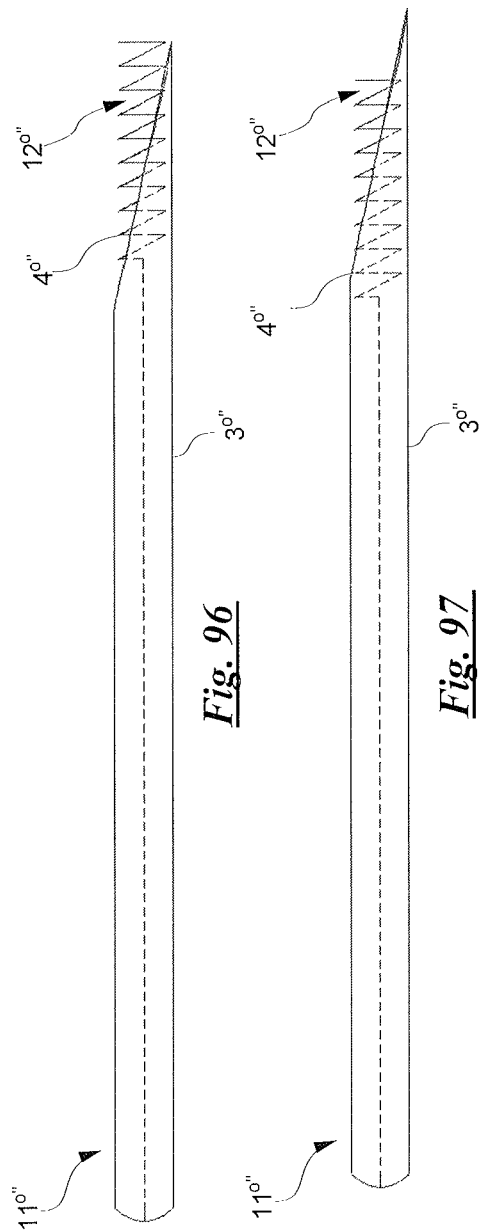

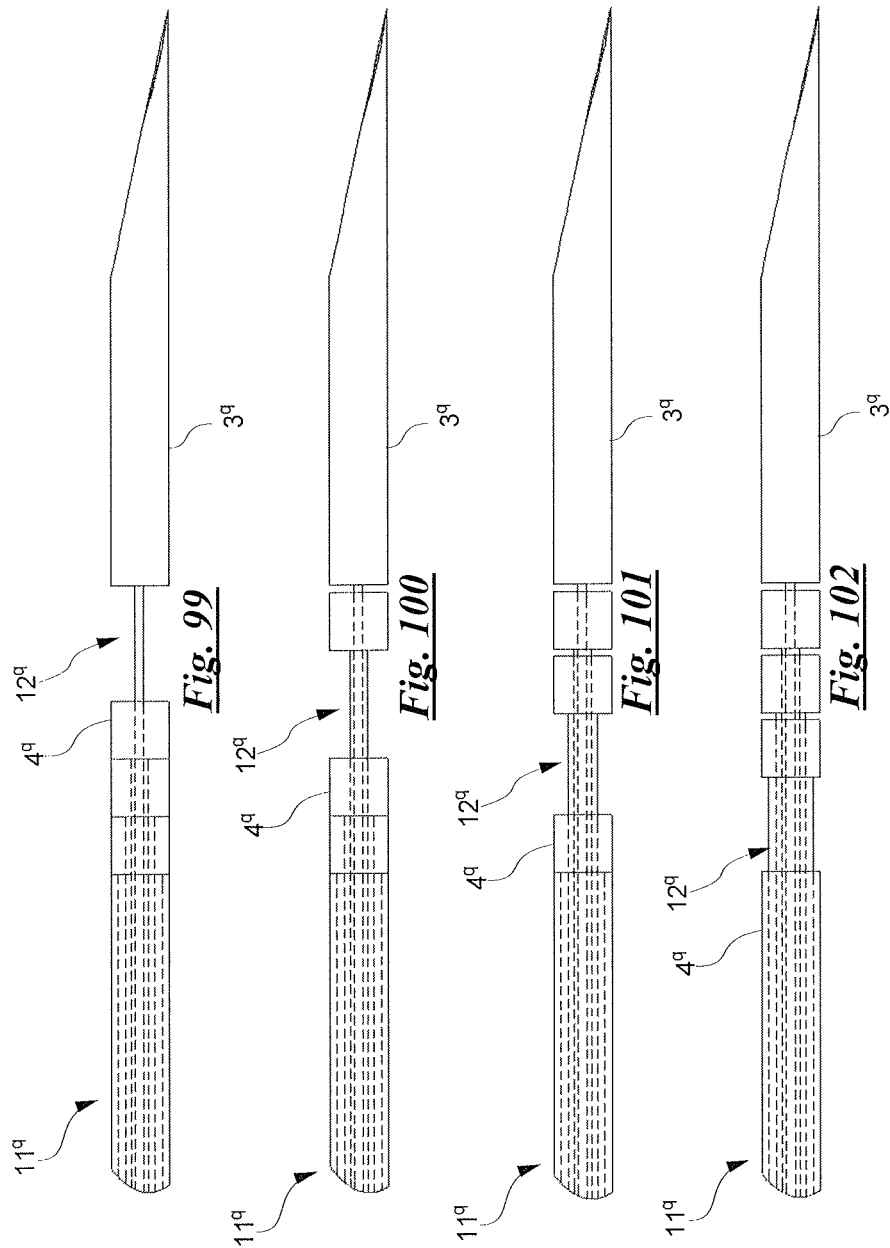

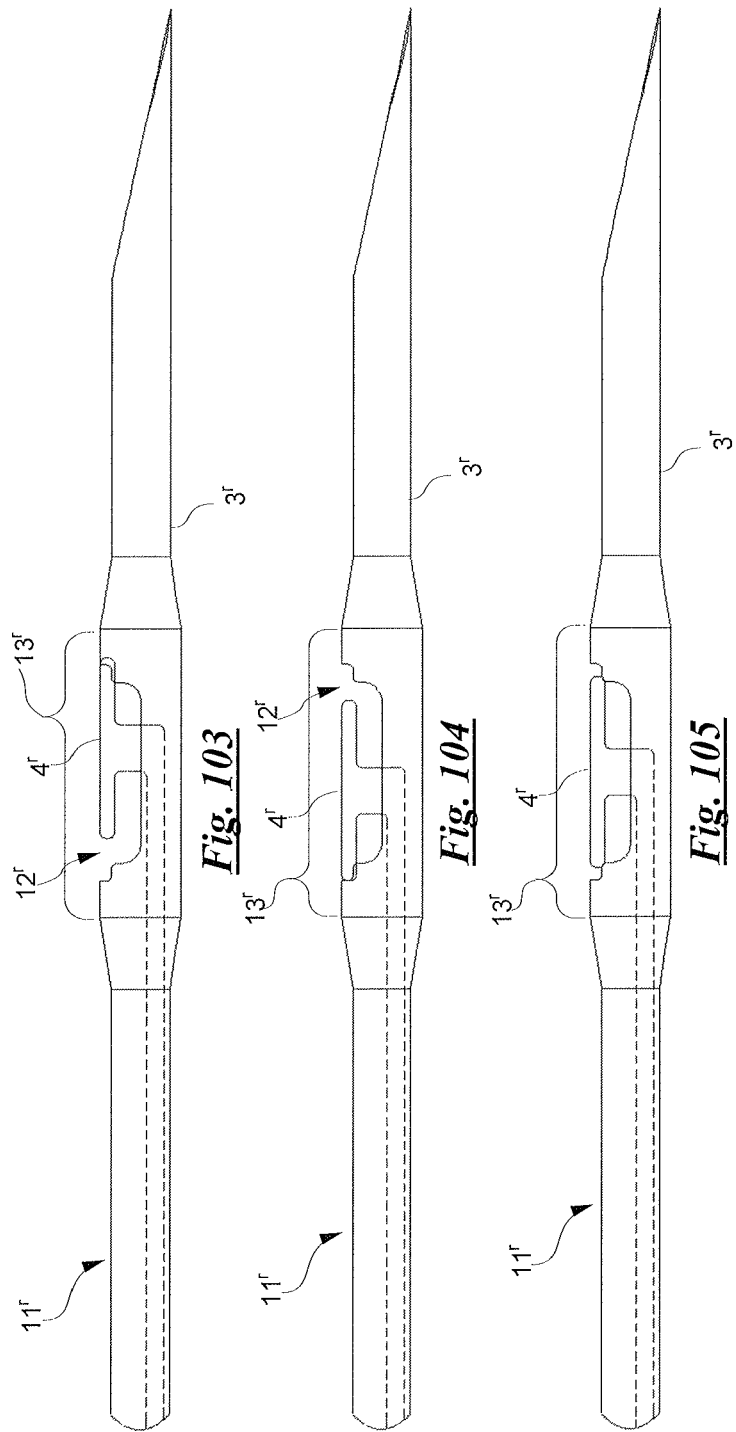

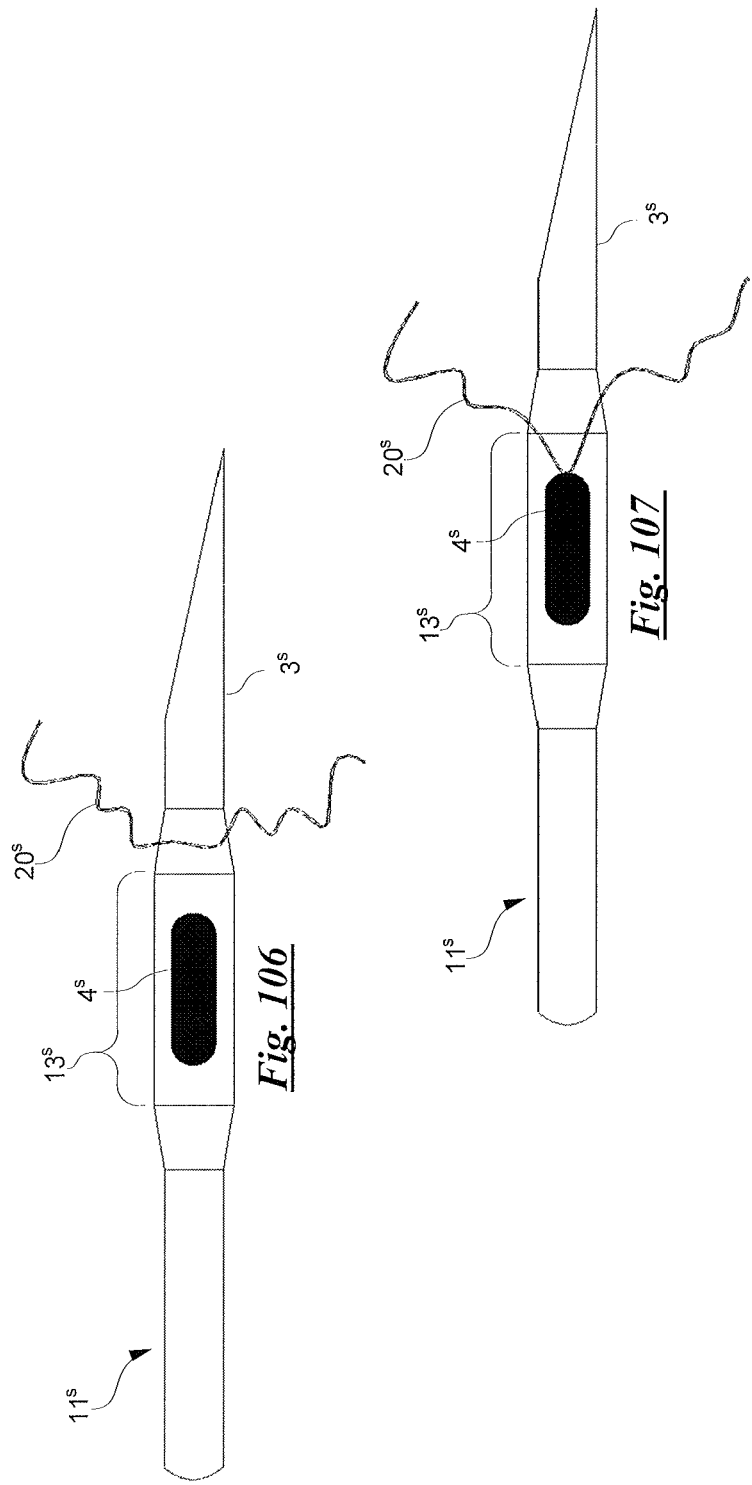

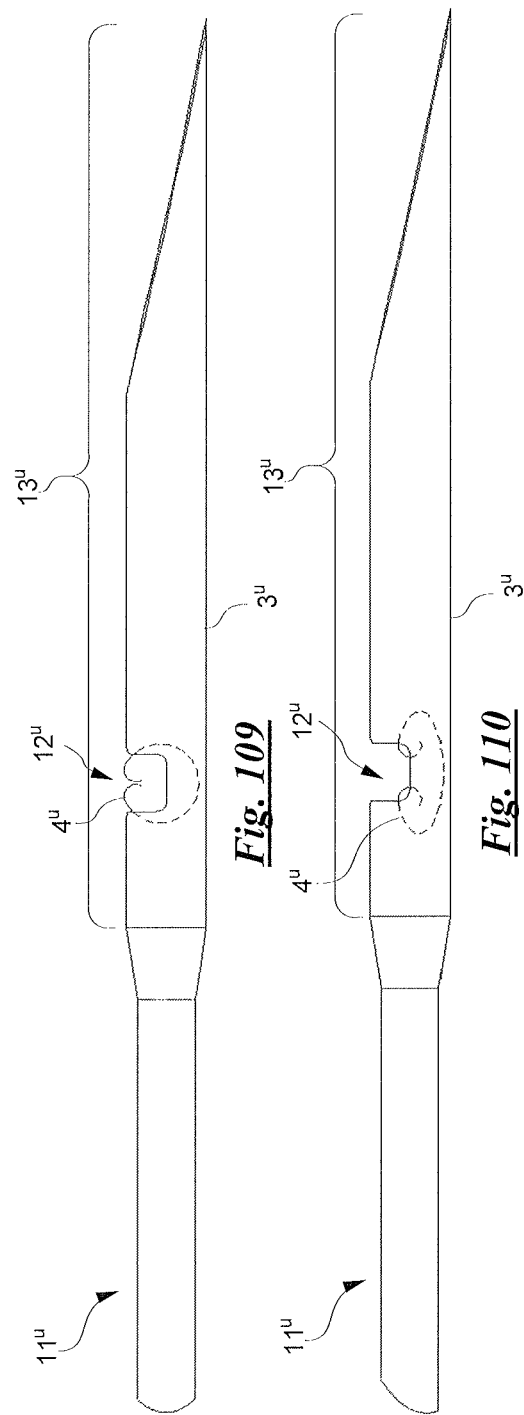

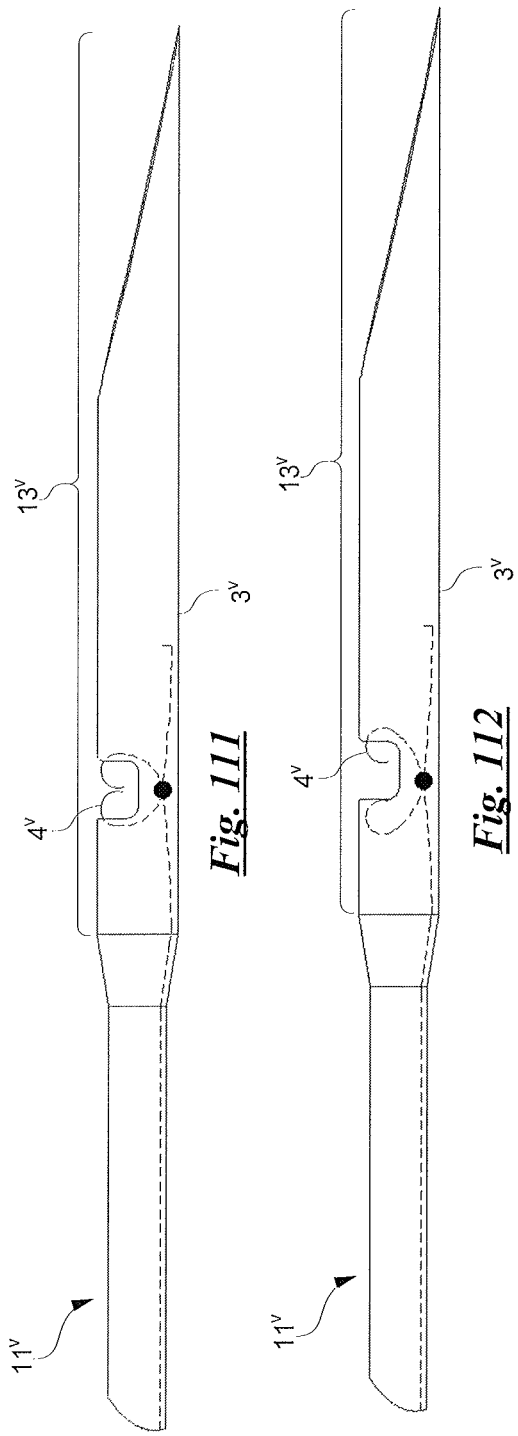

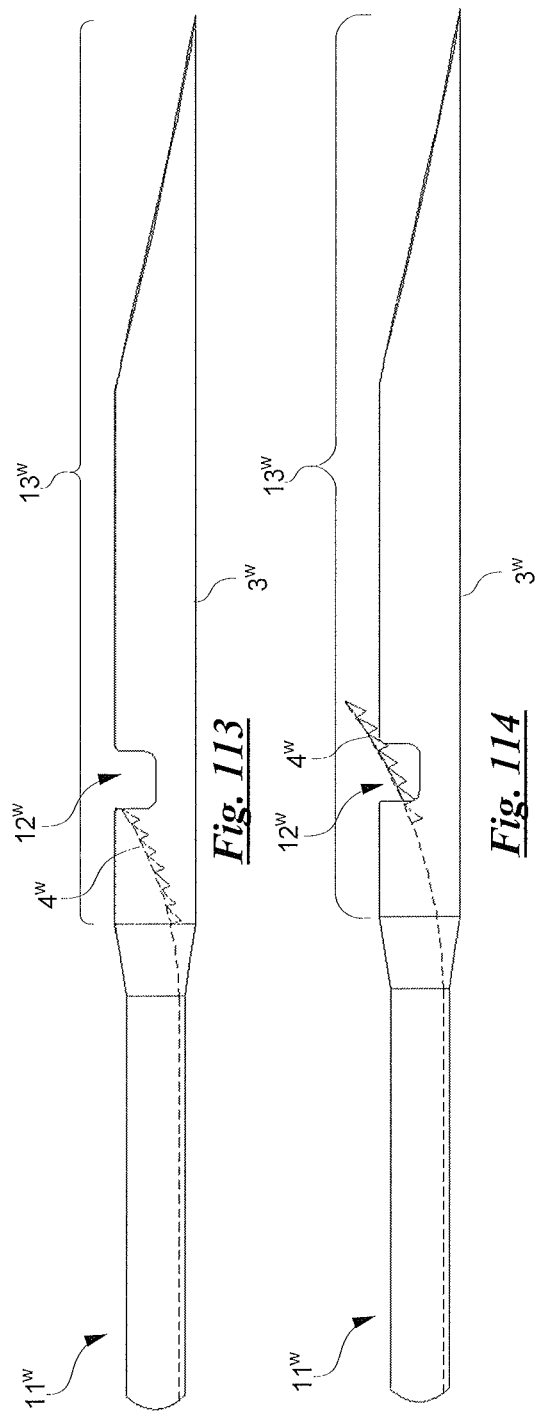

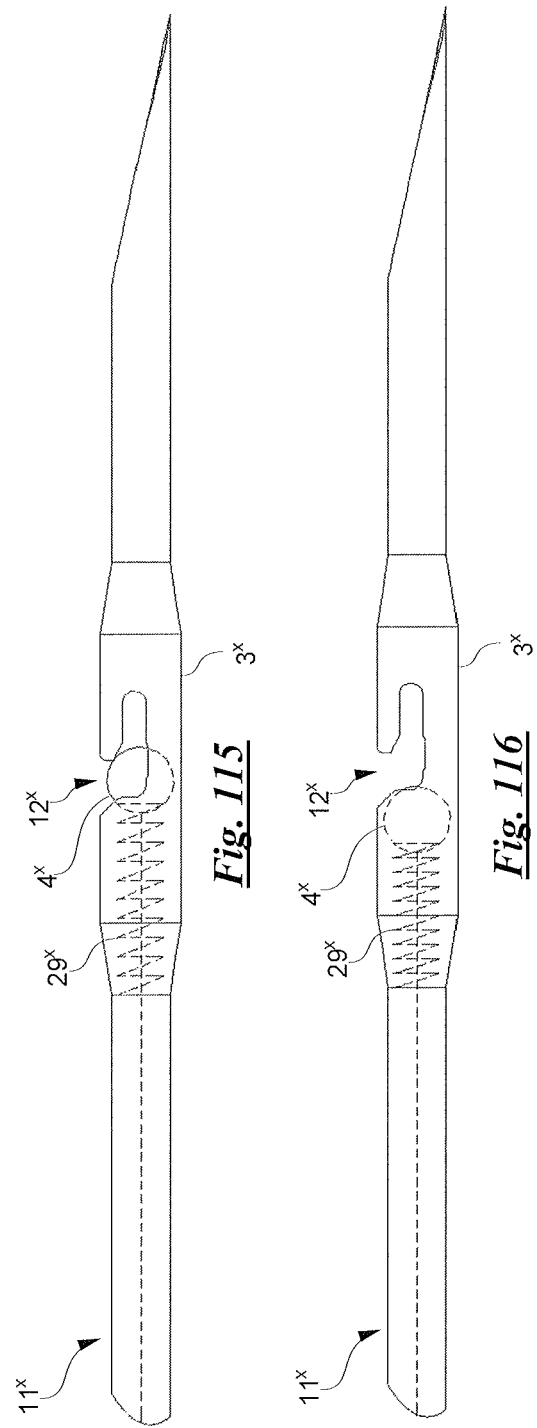

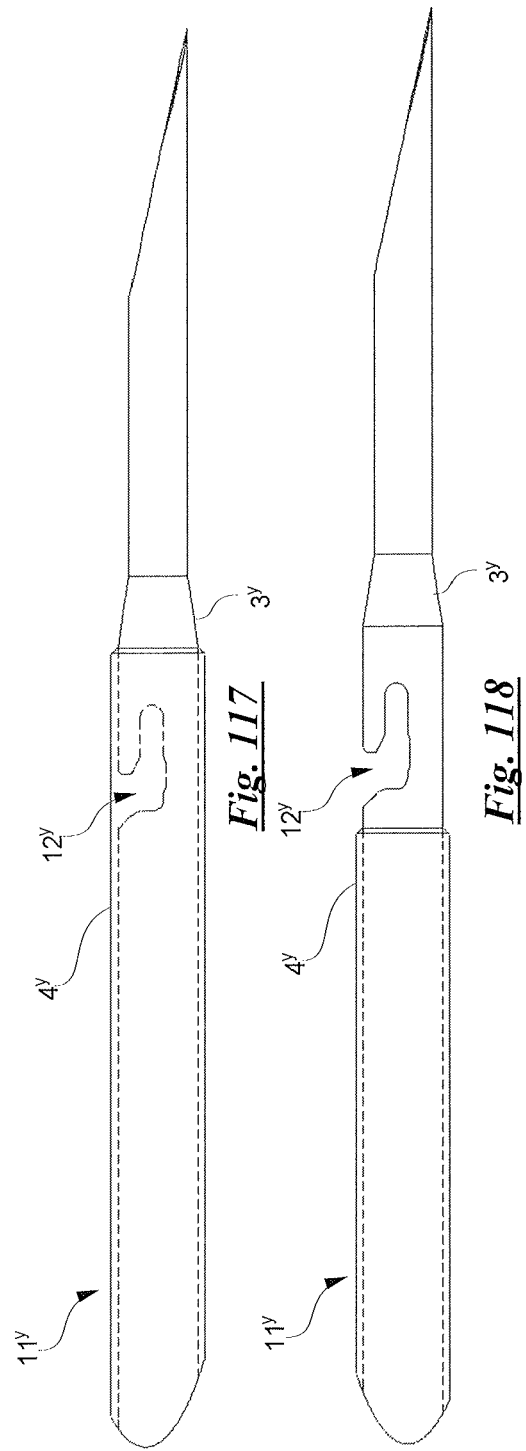

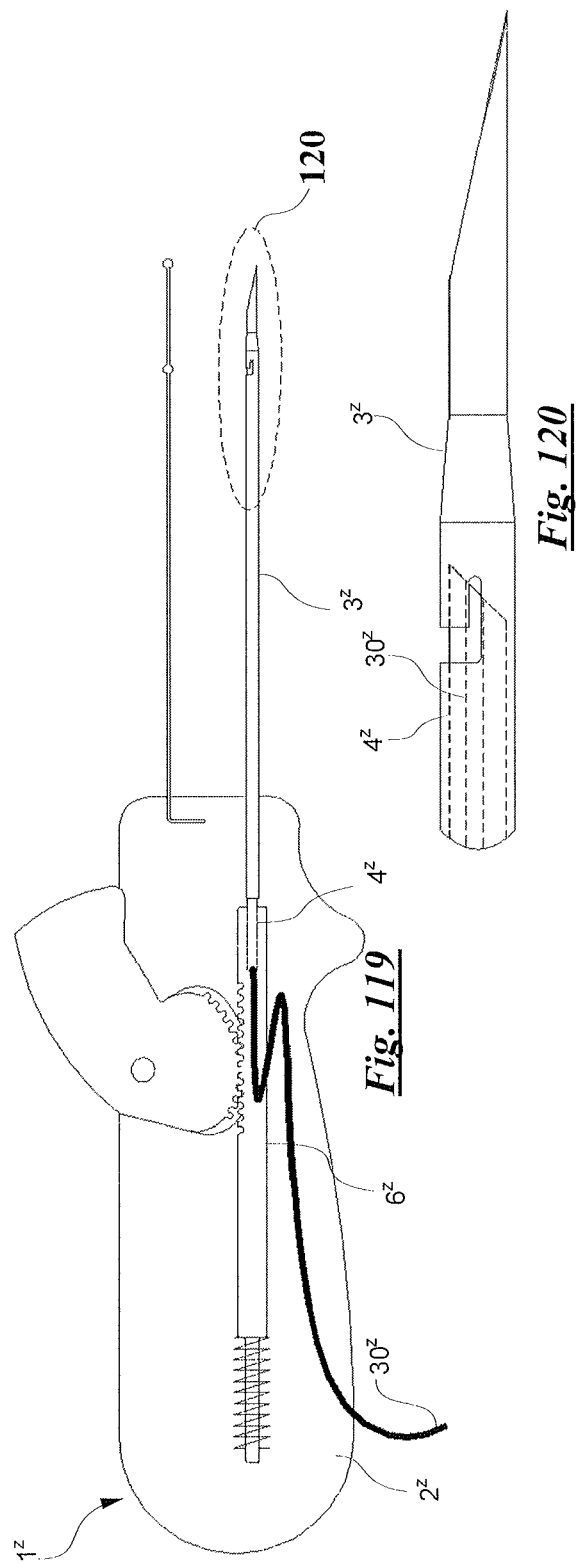

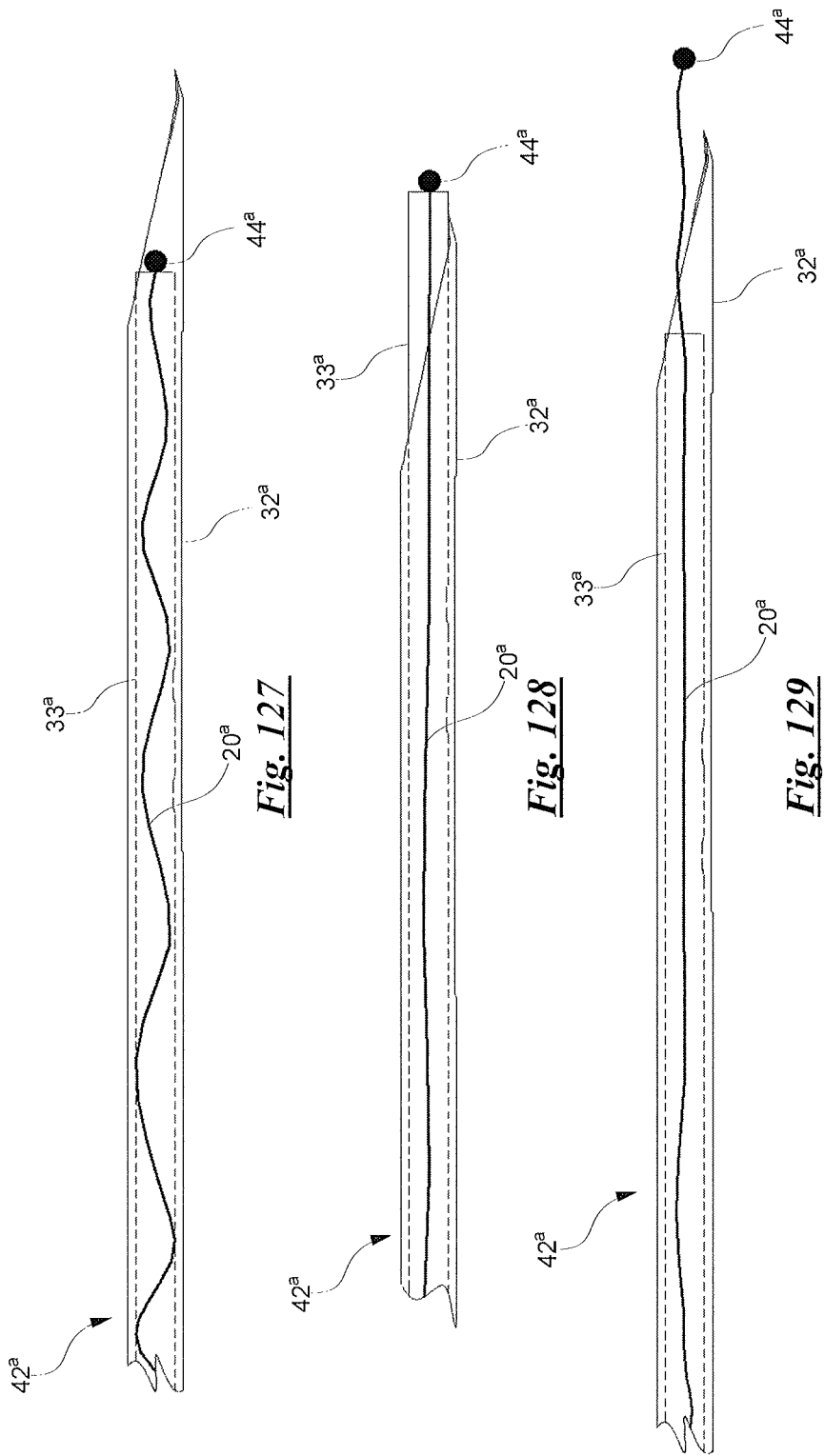

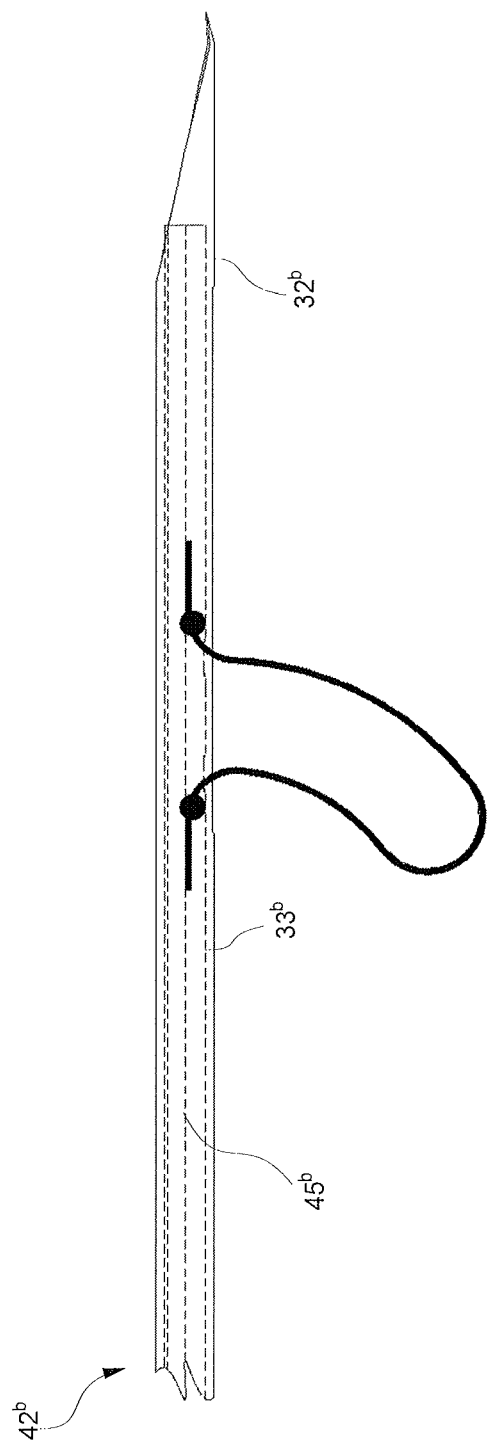

SURGICAL SUTURING DEVICE WITH TRANSVERSE ENGAGEMENT

CROSS-REFERENCE TO RELATED APPLICATIONS

This application is a section 371 of International Application No. PCT/US2014/030533, filed Mar. 17, 2014, which was published in the English language on Sep. 18, 2014 under International Publication No. WO 2014/145724, which claims the benefit of U.S. Provisional Application No. 61/852,050, filed Mar. 15, 2013, the disclosures of which are incorporated herein by reference.

BACKGROUND OF THE INVENTION

The present invention relates to an apparatus capable of enabling a practitioner to thread a suture in subcutaneous tissue from a remote access point, to surgical methods facilitated by such an apparatus, and to associated tools useful with the apparatus for performing such surgical methods.

Various surgical methods require the placement of a suture deep inside subcutaneous tissue for the purpose of supporting, severing, ligating, or constricting tissue, vessels, ligaments, nerves or other anatomy or for pulling another device into position defined by the suture pathway. Typically, this necessitates making an incision through the skin and subcutaneous tissue in order to gain sufficient access for deploying the suture directly to the desired location, for example, in an open surgical procedure or for feeding a suture passing instrument with an endoscopic or laparoscopic instrument to a distal location from the initial point of access.

An example of one such procedure, in the field of plastic surgery, is the mid-face lift. As part of this procedure, an incision is made in an inconspicuous location to conceal the incision and to make scarring less obvious. The facial tissue is then separated to achieve sufficient access and mobility of the tissue to permit one or more sutures to be deployed to reattach and/or reposition the tissue into a more aesthetically desirable result. In addition, it is often desirable to anchor ends of the sutures to a rigid structure, for purposes of support. In practice, however, the selection of an anchoring structure which is suitable for fixation, which is accessible, and which can provide an inconspicuous incision, often complicates the procedure and results in a significant distance between the supported tissue and the fixation structure. The can result in a procedure which requires extensive surgery, which can be expensive, which can create significant trauma to the tissue, and which can take a significant amount of time to heal (e.g., a matter of weeks), and may also create sub-optimal aesthetic results.

Various procedures have been attempted to reduce the resulting trauma to a patient, the corresponding expense of the procedure, and the time required for recovery. For example, one attempted procedure has been to use needles to implant a device having barbed profiles capable of engaging subcutaneous tissue at a location remote from the point of access. In practice, however, such barbs have been found to be prone to release after a relatively short period of time, often on the order of a few months. Release of the barbs then allows the engaged tissue to sag.

Other attempted procedures have made use of endoscopes to reduce the size of the accessing incision. However, endoscope-guided suturing devices are bulky mechanisms, and tend to require considerable separation of the tissue layers and the severing of connective fibers in order to pass the instrument from the incision at the anchor location to the intended base of the suture supporting loop, and to surgically release the naturally occurring connective fibers so that the lift will be effective. Moreover, in the case of an endoscopic-guided mid-face lift, significant care and skill are required to avoid rupturing critical branches of the facial nerve as the device traverses a path from the temporal fascia to the intended location. Furthermore, endoscopic suturing devices are limited in the amount of tissue that can be engaged distally to distribute the lifting force, which can make the sutures prone to pull through the tissue (so-called "cheese-wire effect") over time. Additionally, the endoscopic mid-face lift begins in the temporal fascia in the hairline in order to hide the insertion incision scar and to provide a suitable structure to anchor the sutures. However, this alters the naturally occurring anchor location of the mid-face tissue to a location which is substantially superior and which can result in a lift vector which is long and constrained by other anatomy, which can affect the aesthetics of the lift.

It has therefore remained desirable to provide a minimally invasive technique for redirecting a suture along a desired pathway or to transfer a suture from one internal pathway to another through the use of external manipulation and tactile feel, as well as to achieve an optimum suture deployment vector for a desired procedure, while providing a practitioner with considerable flexibility in the choice of vector and suture configurations and the ability to capture multiple sutures.

SUMMARY OF THE INVENTION

In accordance with the present invention, an apparatus and associated tools are provided for enabling a practitioner to thread a suture in subcutaneous tissue from a remote access point, to facilitate any of a variety of surgical methods. In addition to enabling advantageous placement of the suture, the device utilizes small gage needles to penetrate the skin. As a result, there is no incision, or a concern for scarring, which enables the location of an anchoring point to be selected to optimize the procedure to be performed.

For convenience of description, the discussion which follows will primarily refer to use of the present invention to perform a mid-face lift. Nevertheless, it is to be understood that improvements in accordance with the present invention can be used to perform other procedures, including other mid-face lift procedures, and other lift procedures, as well as other surgical procedures which can benefit from the non-invasive percutaneous deployment and manipulation of a suture in a pathway.

As an example, and for the illustrative case of a mid-face lift, this enables the suture to be placed through the skin and into the periosteum of the zygomatic arch, which then serves as the anchoring structure for the mid-face lift. In addition to providing a strong anchoring location for the lift, the zygomatic arch is a naturally occurring anatomical fixation point for the tissue that comprises the mid-face.

Additionally, the present invention enables an improved aesthetic result to be achieved by allowing the development of a more aesthetic lift vector and a shorter lift length.

This is to be distinguished from other procedures, such as the modified "S-Lift", which provides access to the mid-face from an incision around the ear, and the previously described endoscopic lift, which can both disrupt and sever the connective tissue which connects the mid-face to the zygomatic arch, and which can result in a more dramatic aesthetic change with significant repositioning of tissue which may be considered undesirable and less natural.

In addition to aesthetic advantages, and by providing a naturally occurring aesthetic vector which is shorter, the present invention can achieve a vector which, for the example of a mid-face lift, can advantageously be contained within a safe region known as the golden triangle, and which avoids having to insert surgical instruments past sensitive anatomy such as the temporal branch of the facial nerve which, if severed, can result in paralysis of the face.

Additionally, the present invention enables the suture to be threaded inside the tissue without disrupting the surrounding tissue, in an advantageous configuration that is controlled by the surgeon, and which minimizes trauma and enables the surgeon to avoid the need to sever naturally occurring ligature connecting the mid-face to the zygomatic arch, Further, and for the illustrative example of a mid-face lift, the present invention enables the surgeon to deploy a suture in a triangular loop support structure with the apex of the triangle at the anchor location and a relatively wide base, typically on the order of 1 cm, in the soft tissue to better distribute the lifting force.

The advantages obtained using the improvements of the present invention for the noninvasive percutaneous deployment of a suture pathway in the illustrative example of the mid-face lift are also applicable to various other procedures.

As another illustrative example, improvements in accordance with the present invention can be used to create a subcutaneous suture loop around a tendon or a ligament without necessitating an incision. In the case of carpal tunnel surgery, a tendon is typically severed in an open procedure dissecting down to the tendon and the tendon is then severed with a scalpel. Instead, a suture loop, for example, in a U-shaped configuration) can be deployed around the tendon using the improvements of the present invention. Guidance of the structures around critical anatomy, such as nerves, can be achieved with ultrasonic guidance. Then, the suture loop can be manipulated back and forth to cut through the tissue. A separate needle can be deployed, if desired, to limit passage of the suture loop through engaged tissue in cases where a complete severing of the tissue is not to take place. As a further alternative, the procedure can be performed with saline, for example, for hydro-dissection, or with the addition of an anesthetic. Similar techniques can be used for the suturing used to repair an Achilles Tendon, or for repairing Varicose veins, or to close off an organ or vessel by tying it shut.

Improved instruments and methods for deploying and manipulating sutures in subcutaneous tissue are described in International Application No. PCT/US2008/009012, filed Jul. 25, 2008, which describes an external guide for aligning a suture with subcutaneous eyelets, and an expandable aperture for engaging a strand which is hidden from view; and in U.S. patent application Ser. No. 12/384,326, filed Apr. 2, 2009 (also International Application No. PCT/US2010/000891, filed Mar. 25, 2010), which describe an external guide for aligning a suture with internal eyelets which can be tethered, as well as removable, the subject matter of each of which is incorporated by reference as if fully set forth herein.

In practice, however, the geometry of these guide structures must be taken into account by a practitioner when deploying such devices. This has the potential for reducing the practitioner's flexibility, which can in turn require suboptimal positioning of the suture loop in order to accommodate variations in a patient's anatomy, which can limit the locations in the body where such devices can be used. There is also the potential for bending forces to affect guided needle systems, which can cause deflection of the needle to increase exponentially with the length of the needle. This can in turn limit the ability of the guiding needle to couple with its target as the distances increase, unless the needle profiles are increased in size to increase stiffness and/or the needle lengths are kept short and/or the size of the targeted elements is increased. However, this can limit the minimum bore diameter of the needles.

In addition, such structures also involve the coupling of elements, such as eyelets, to the guides, which can result in additional components and procedural steps for the practitioner. In accordance with the present invention, subcutaneous coupling with a distally deployed cannula, or other cooperating element, permits even the more complex suture pathway to be configured in the subcutaneous tissue into a desired a loop configuration or some other prescribed pathway without requiring an external alignment structure. Moreover, bending forces on subcutaneous tools are better accommodated by allowing for re-directed adjustment of the components to achieve the desired coupling, which can be confirmed by tactile feel, electronic sensing, as well as ultrasonic or other guidance systems toward subcutaneous needles for subcutaneous mating with target elements. This significantly increases the percutaneous flexibility of the practitioner to manipulate suture pathway into optimally desired configurations, making the use of improvements in accordance with the present invention appropriate for a wider variety of procedures and anatomical targets.

BRIEF DESCRIPTION OF THE DRAWINGS

FIG. 2 is an enlarged view of region 2 of FIG. 1 showing the engagement mechanism.

FIGS. 3 and 4 are cross-sections of the penetrating member shown in FIG. 1.

FIG. 5 is an isometric view of region 5 in FIG. 1 in the region of the engagement feature.

FIG. 7 is an enlarged plan view of the distal end of the engagement mechanism in region 7 of FIG. 6.

FIG. 8 is an expanded isometric view of region 8 in FIG. 7 showing the engagement feature.

FIG. 20 is a plan view two strands captured in the engagement feature.

FIG. 21 is a plan view of an alternative embodiment engagement mechanism with a hook and a "V" shaped engagement feature.

FIG. 22 is an isometric view of region 22 of FIG. 21.

FIG. 23 is a plan view of the alternative embodiment shown in FIG. 21 with the hook in a retracted position for capturing a tethered cannula or strand.

FIG. 24 is an isometric view of region 24 of FIG. 23.

FIGS. 32, 33 and 34 are progressive plan views of the engagement mechanism with the rotating capture mechanism progressively rotated to show the stages of capture in the engagement features.

FIG. 35 is a plan view of an alternative embodiment of the engagement mechanism including a capture mechanism with a flexible latch and a guard in a forward position restricting the latch from flexing.

FIG. 36 is an isometric view of region 36 of FIG. 35.

FIG. 37 is a plan view the engagement mechanism shown in FIG. 35 with the guard retracted to allow the latch to flex.

FIG. 38 is an isometric view of region 38 of FIG. 37.

FIG. 39 is a plan view of the engagement mechanism shown in FIG. 37 with the latch flexed inwardly by an external force.

FIG. 40 is an isometric view of region 40 of FIG. 39.

FIG. 41 is a plan view of another alternative embodiment of an engagement mechanism with a latch.

FIG. 42 is an isometric view of region 42 of FIG. 41.

FIG. 43 is a plan view of the engagement mechanism shown in FIG. 41 with the latch flexed inwardly by an external force.

FIG. 44 is an isometric view of region 44 of FIG. 43.

FIG. 45 is a plan view of an alternative embodiment engagement mechanism where the capture mechanism translates across a guard/support and provides capture for multiple engagement features.

FIG. 46 is an isometric view of region 46 of FIG. 45.

FIG. 47 is a plan view of the progressive advancement of the capture mechanism for the engagement mechanism shown in FIG. 45 showing capture in the proximal engagement feature.

FIG. 48 is an isometric view of region 48 of FIG. 47.

FIG. 49 is a plan view of the continued progressive advancement of the capture mechanism for the engagement mechanism of FIG. 45 showing capture in the distal engagement feature.

FIG. 50 is an isometric view of region 50 of FIG. 49.

FIG. 51 is a plan view of an alternative embodiment of an engagement mechanism which incorporates a capture mechanism with a flexible latch that flexes outward when a force not shown is applied to the latch along the horizontal slot of the engagement feature.

FIG. 52 is an isometric view of region 52 of FIG. 52.

FIG. 53 is a plan view of the engagement mechanism of FIG. 51 where the capture mechanism is flexed outwardly by a force which is applied through the horizontal slot of the engagement feature.

FIG. 54 is an isometric view of region 54 of FIG. 53.

FIG. 55 is a plan view of an alternative embodiment of an engagement mechanism which includes a capture mechanism which is capable of flexing over and capturing a tethered cannula in transverse alignment at the engagement feature.

FIG. 56 is an isometric view of region 56 of FIG. 55.

FIG. 57 is a plan view of the engagement mechanism of FIG. 55 where the capture mechanism is shown in an advanced position where it has snapped over and captured a tethered cannula in the engagement feature.

FIG. 58 is an isometric view of region 58 of FIG. 57.

FIG. 60 is a plan view of the engagement mechanism of FIG. 59 with the capture mechanism extended beyond the distal tip of the penetrating member.

FIG. 61 is an isometric view of region 61 of FIG. 60.

FIG. 62 is a plan view of the engagement mechanism of FIG. 59 partially retracted into the tip of the penetrating member.

FIG. 63 is an isometric view of region 63 of FIG. 62.

FIG. 65 is a plan view of the engagement mechanism of FIG. 64 shown with the capture mechanism extended.

FIG. 66 is an isometric view of region 66 of FIG. 65.

FIG. 67 is a plan view of the engagement mechanism of FIG. 65 with the capture mechanism partially retracted.

FIG. 68 is an isometric view of region 68 of FIG. 67.

FIG. 69 is a plan view of an alternative engagement mechanism where the penetrating mechanism includes a helical section.

FIG. 70 is a plan view of the engagement mechanism of FIG. 69 with the capture mechanism shown as a rod inserted through the helical section.

FIGS. 71, 72 and 73 are progressive plan views of an alternative embodiment similar in function to the embodiment shown in FIG. 35 of an engagement mechanism including a capture mechanism with a flexible latch and a movable guard/support.

FIGS. 82, 83, 84 and 85 are progressive plan views of an alternative embodiment of an engagement mechanism which show a penetrating member with a modified tip.

FIG. 86 is a plan view of an alternative embodiment of an engagement mechanism similar to the embodiment shown in FIG. 35 but without the guard/support.

FIG. 87 is a plan view of the engagement mechanism of FIG. 86 with the capture mechanism bent inwardly by a force.

FIG. 88 is a plan view of an alternative embodiment of an engagement mechanism with a capture mechanism that is inflatable.

FIG. 89 is a plan view of the engagement mechanism of FIG. 88 where the capture mechanism is inflated.

FIG. 90 is a plan view of an alternative embodiment of an engagement mechanism where the guard directly blocks off the engagement region in the closed state and the guard and capture mechanism are both movable.

FIG. 91 is a plan view of the engagement mechanism of FIG. 90 with the guard and capture mechanism retracted and the capture mechanism flexed inwardly by a force.

FIG. 92 is a plan view of an alternative embodiment of an engagement mechanism where the capture mechanism includes a coil which is housed within the penetrating member.

FIG. 93 is a plan view of the engagement mechanism of FIG. 92 where the coiled section of the capture mechanism is compressed in a position to capture tethered cannulas or strands between the coils.

FIG. 94 is a plan view of an alternative embodiment of an engagement mechanism where the capture mechanism includes a coil which is wrapped around the outside of the penetrating member.

FIG. 95 is a plan view of the engagement mechanism of FIG. 94 where the coiled section of the capture mechanism is compressed in a position to capture tethered cannulas or strands between the coils.

FIG. 96 is a plan view of an alternative embodiment of an engagement mechanism in which the capture mechanism includes a coil which can protrude from the end of the penetrating member.

FIG. 97 is a plan view of the engagement mechanism of FIG. 96 showing the coils of the capture mechanism partially retracted into the penetrating member.

FIGS. 99, 100, 101 and 102 are progressive plan views of an alternative embodiment of the engagement mechanism which include telescoping capture mechanisms.

FIGS. 103, 104 and 105 are progressive plan views of an alternative embodiment of the engagement mechanism which show a capture mechanism with a front and rear hook section and the progressive stages of capture.

FIGS. 106 and 107 are plan views of an alternative embodiment of an engagement mechanism with a capture mechanism which includes a magnet and interaction with a strand which includes magnetic particles.

FIGS. 109 and 110 are progressive plan views of an alternative embodiment of the engagement mechanism which includes a capture mechanism which can open and close around a tethered cannula or strand which exerts an inwardly directed force on the capture mechanism.

FIGS. 111 and 112 are progressive plan views of an alternative embodiment of the engagement mechanism which includes a capture mechanism with jaws that can be opened and closed around a tethered cannula or strand.

FIGS. 113 and 114 are progressive plan views of an alternative embodiment of the engagement mechanism which includes a flexible capture mechanism with barbs which when extended can pass over a tethered cannula and when retracted engage and capture a strand or a tethered cannula.

FIGS. 115 and 116 are progressive plan views of an alternative embodiment of the engagement mechanism with a capture mechanism with a spring loaded ball.

FIGS. 117 and 118 are progressive plan views of an alternative embodiment of the engagement mechanism with a capture mechanism including a sheath which slides to open or close off the engagement feature.

FIGS. 119 and 120 are plan views of an alternative embodiment of the engagement tool which include a fluid pathway for dispensing fluid through the penetrating member.

FIGS. 127, 128 and 129 are progressive plan views of an alternative embodiment of the front end of the routing tool which includes a strand which enables the routing tool to couple directly with an engagement tool without coupling with an external strand.

FIG. 131 is an expanded plan view of region 131 of FIG. 120 showing the fluid pathway through the front end of the routing tool.

DETAILED DESCRIPTION OF PREFERRED EMBODIMENTS

Figure 1:
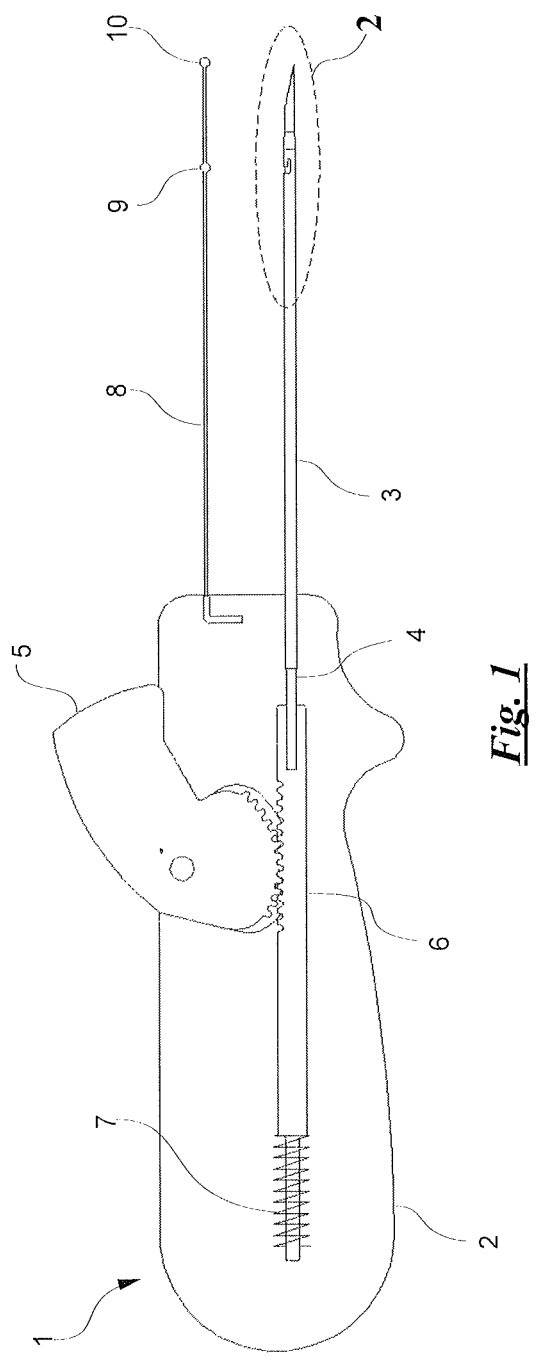
FIG. 1 is a plan view of the preferred embodiment of the engagement tool.

FIG. 1 shows an embodiment of an apparatus produced in accordance with the present invention which is presently considered as being preferred. The engagement tool 1 includes a body 2 with a penetrating member 3 which is affixed to the body. In the preferred embodiment, the penetrating member 3 is made from a cannula which allows a capture mechanism 4 to translate within the penetrating member 3. In other embodiments, the penetrating member 3 can be of other constructions, including solid materials, and the capture mechanism can be affixed to the penetrating member or coupled to the outside of the penetrating member. The penetrating member 3 is shown with a pointed tip at the distal end of the penetrating member 3, which is preferred to facilitate entry into tissue such as skin. The tip of the penetrating member can also be of other configurations, including blunt or rounded shapes, if appropriate for an application where the device can readily pass through tissue without having a sharp point, such as where there is a prior incision or puncture. An introducer needle can be used to facilitate the insertion of a penetrating member having a blunt or rounded tip, if desired.

Figure 6:
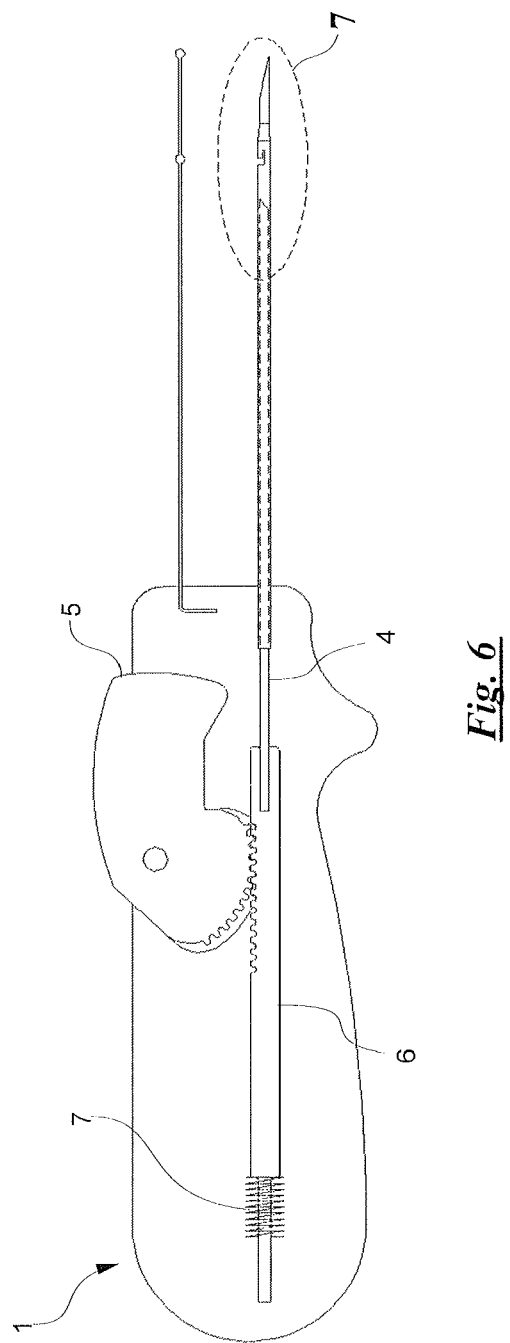
FIG. 6 is a plan view of the engagement tool with actuator depressed and the capture mechanism retracted.

In the preferred embodiment of FIG. 1, an actuator 5 interacts with a carriage 6, which is preferably coupled to the proximal end of the capture mechanism 4. In this preferred embodiment, when the actuator is depressed, the actuator 5 rotates about a pivot and the gears of the actuator interact with the linear gears of the carriage, causing the capture mechanism 4 to reciprocate within the penetrating member 3. FIG. 6 shows the engagement tool 1 with the actuator 5 depressed and rotated forward, placing the carriage 6 and the attached capture mechanism 4 in a retracted position and compressing a return spring 7 for returning the capture mechanism to its original state when the actuator mechanism is released. Any of a variety of actuator mechanisms can be used as alternatives. For example, the penetrating member can translate and the capture mechanism can be fixed, or the actuator can be directly coupled to the penetrating member or the capture mechanism, where no carriage is used, and where there is no spring return. It is also possible to manually couple a capture mechanism to the penetrating member without an actuator.

Referring again to the preferred embodiment in FIG. 1, the engagement tool 1 also includes an indicator 8. In applications where the penetrating member 3 is inserted into tissue, the penetrating member is typically hidden from view. The indicator 8, as shown, remains above the tissue and provides a visual indication of the location of features of the penetrating member. For example, an engagement locator 9 can be used to locate suture engaging features of the penetrating member, and a tip locator 10 can be used to locate the tip of the penetrating member. The indicator 8 is preferably made from a flexible material, for example, nitinol wire, which is sufficiently stiff to provide the desired visual indication, but with the added feature that the indicator can be bent out of the way of occluded tissue which may occur as the user introduces the device into the skin or manipulates the device toward the target location. In the preferred embodiment, the locators 9 and 10 are applied adhesive materials. Other flexible and non-flexible materials can also be used, as well as well as other forms of visual locators, such as beads or sleeves. A plurality of engagement locators 9 can be used to identify multiple engagement locations, if desired.

FIG. 2 is an enlarged view of the engagement region 2 identified in FIG. 1, showing the distal end 11 of the penetrating member 3. In the preferred embodiment, the penetrating member 3 includes an engagement feature 12 which is shown as an "L" shaped relief in the penetrating member. While FIG. 2 shows only one engagement feature 12, it is possible to have more than one engagement feature, if desired. FIG. 5 is an isometric view of the region 5 shown in FIG. 1.

In the preferred embodiment the capture mechanism 4, which is shown in its forward-most position, includes an angled front tip. In this location, the engagement feature 12 is closed, preventing it from receiving an object, such as a cannula or suture. While it is also possible to leave the engagement feature partially open so that it can receive a small diameter object, such as a suture or cannula, unless the engagement feature is smoothly contoured it will act as a catch point when penetrating or retracting through tissue, particularly when used to penetrate skin. By blocking the opening with the capture mechanism, tissue is prevented from getting caught on or in the engagement feature. A further advantage of the illustrated embodiment is that while the capture mechanism 4 is in the state shown in FIG. 2, a transition remains along the penetrating member at the engagement feature which provides the user with a tactile indication that an object, such as a cannula or suture, which is held in a generally transverse orientation to the penetrating member in FIG. 2, traverses across the top of the penetrating member and comes in contact with the engagement feature 12, as will later be shown FIG. 15. To be noted is that the term "transverse" is not intended to mean that the described features must meet at a right angle to each other, and that other angles can also be established for this.

FIG. 7 shows the distal end of the engagement mechanism 11 with the capture mechanism 4 in a retracted position. FIG. 8 is an enlarged isometric view of the distal end of the engagement mechanism 11 shown in FIG. 7. In this retracted state, the engagement feature is open to receive a desired object.

The penetrating member 3 is preferably made from a cannula with a pointed tip. Referring to FIG. 3, the cannula is preferably flattened into an oval geometry in the region 13, The main advantage of an oval geometry is structural strength, so that for a given depth of relief required to capture a desired object, there will still be sufficient strength in the penetrating member. While it is also possible to use a larger cannula for the penetrating member, to retain the structural integrity, it is typically desirable to minimize the size of the penetrating member to reduce unnecessary trauma to the tissue. FIGS. 3 and 4 show preferred cross sections for the bracketed regions 13 and 15. Bracketed region 14 is a transition region from the oval region 13 to the circular region 15.

Figure 9:
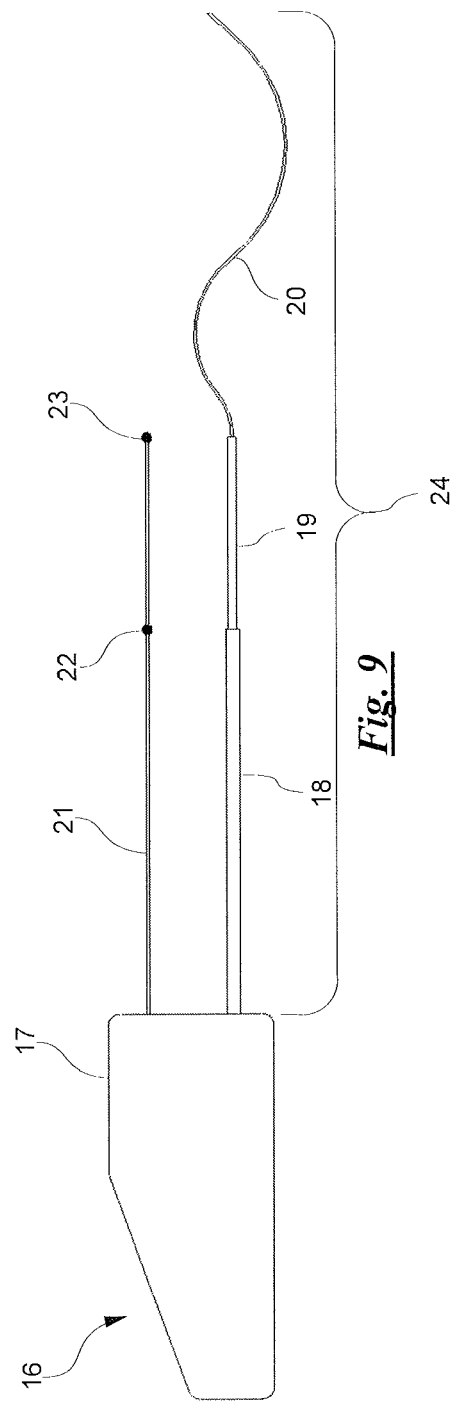
FIG. 9 is a plan view of a tethered cannula tool.

FIG. 9 shows a preferred embodiment of a tethered cannula tool 16. The tethered cannula tool 16 includes an alternative embodiment body 17 which holds an outer cannula 18 and narrow cannula 19 sized to interact with the engagement feature 12 of the engagement tool 1. The cannulas 18 and 19 are further coupled with a strand 20, which is preferably a suture but which can also be a flexible wire. The cannula 19 is preferably slidingly received within the cannula 18, and the strand 20 is preferably slidingly received within the cannula 19.

FIG. 9 also shows an indicator 21 having cannula locators 22 and 23 which serve to identify the region where the narrow cannula 19 is exposed. The indicator 21 is preferably made with a flexible material, such as nitinol wire, for the same reasons as were previously discussed for the indicator 8 of the engagement tool 1 described in FIG. 1, and the locators 22 and 23 are preferably made with drops of adhesive, as previously described. Again, the indicator 21 may be made of a flexible or stiff material, and various markings or identifiers can be used to identify regions of the cannulas 18 and 19.

If the strand 20 is held in tension, the engagement tool 1 can interact with the strand without needing any of the other elements shown in FIG. 9. As an alternative, a single cannula (either 18 or 19) can be used with the strand 20 to interact with the engagement tool 1. However, in practice, a tethered cannula which includes each of the elements 18, 19 and 20 is particularly advantageous when used in combination with the preferred embodiment of the engagement tool in FIG. 1 as will be described below.

Figure 10:
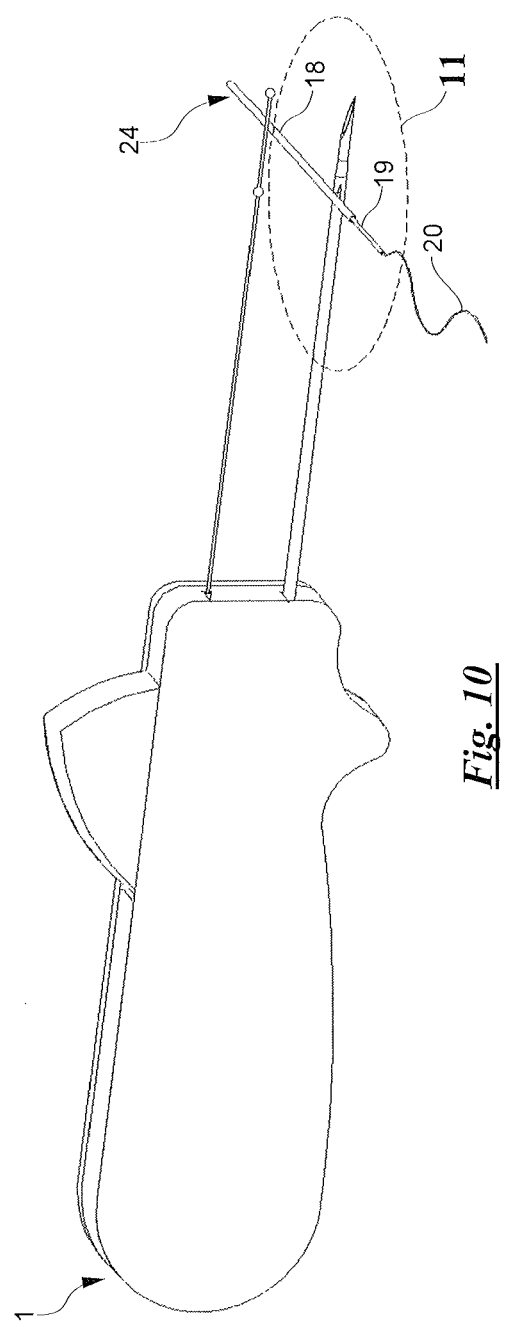
FIG. 10 is an isometric view of the engagement tool in transverse alignment with a tethered cannula.
Figure 11:
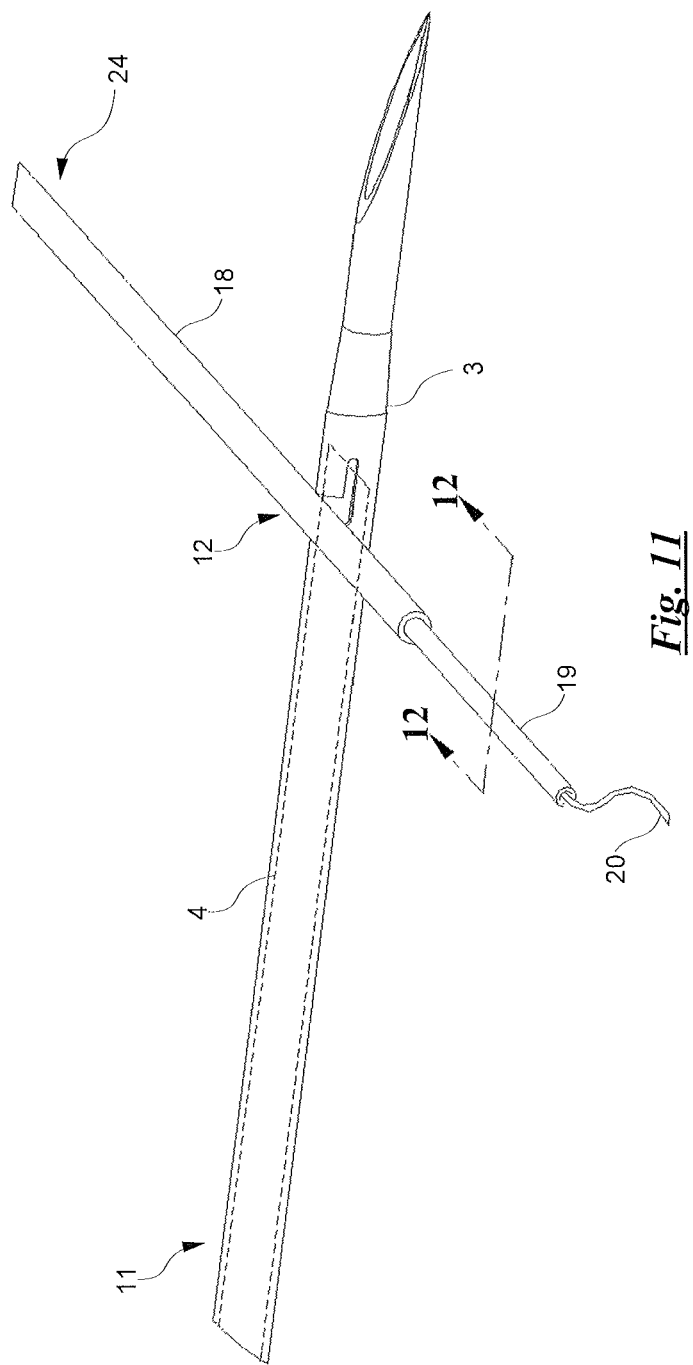
FIG. 11 is an enlarged isometric view of region 11 of FIG. 10 showing transverse alignment of engagement tool with tethered cannula at the engagement feature.
Figure 12:
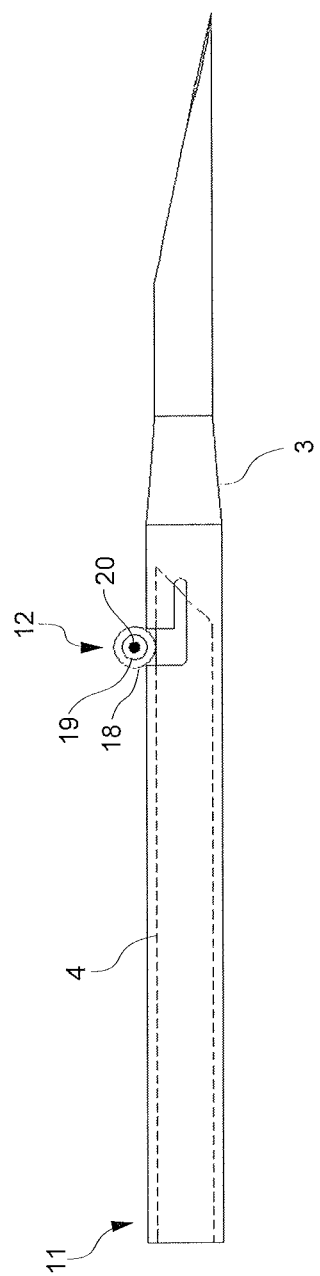
FIG. 12 is a plan view of enlarged region 11 of FIG. 10 showing transverse alignment of engagement tool with tethered cannula at the engagement feature.

FIG. 10 shows a tethered cannula associated with the tool 16, including the outer cannula 18, narrow cannula 19 and tether 20, in transverse alignment with the engagement tool 1. FIGS. 11 and 12 are enlarged views of the region 11 of FIG. 10.

FIGS. 10 to 12 show the outer cannula 18 positioned at the opening of the engagement feature 12 of the penetrating member 3. The diameter of, and material forming the outer cannula are selected to give the tethered cannula sufficient strength, stiffness and geometry to facilitate engagement with the engagement tool.

In use, it is advantageous to be able to manipulate the protruding member 3 of the engagement tool and the tethered cannula of the tool 16 into alignment. For the case where the tethered cannula is deployed first, the engagement tool is inserted into the tissue toward the tethered cannula. As the tip of the penetrating member of the engagement tool approaches the tethered cannula, the tissue can be manipulated by adjusting the attitude of the tethered cannula and the penetrating member until the tip of the penetrating member contacts the tethered cannula. The force of this manipulation exerts a bending force on the tethered cannula and, if the cannula is too weak, it becomes difficult to position the tissue so that the tethered cannula can contact the tip of the penetrating member and then progress along the upper surface of the protruding member, in the orientation shown, until coming into contact with the engagement region 12. As an alternative, it is also possible for the end of the outer cannula 18 opposite the tether to be inserted into the tissue toward a previously deployed penetrating member of the engagement tool, if preferred for a given procedure. To facilitate this, the tip of the outer cannula 18 opposite the tether can be pointed.

In the preferred embodiment, the geometry of the engagement region 12 provides the user with tactile feedback that the tethered cannula is positioned for engagement. The indicator 8 and engagement locator 9 of the engagement tool also provide the user with a visual indication as to where the engagement will occur, as would the indicator 21 of the tethered cannula tool 16 shown in FIG. 9, if used.

While it is advantageous to have tactile feel and visual indicators, it is also possible to have other forms of indicators or alignment such as electrical signals that sense the contact of the different segments of the tethered cannula with other segments of the penetrating member of the engagement tool. Thin insulators, such as polymide tubing, can be used to isolate different elements of the tethered cannula and the penetrating member of the engagement tool so that when, for example, the outer cannula 18 contacts the penetrating member 3, a signal is produced, and when the outer cannula 18 is in contact with the penetrating member 3 at the engagement feature, another signal is produced. Further signals can similarly be developed when the narrow cannula is in contact with the penetrating member or with the capture mechanism. Ultrasound or other sensing devices can also be used to detect features of the penetrating member 3, if desired for a particular application.

Referring to FIG. 12, the width of the upper opening of the engagement feature 12 is sufficiently large for the narrow cannula 19 to enter the engagement feature when the capture mechanism 4 is retracted. While the width of the opening could also be designed to accommodate the outer cannula 18, it is advantageous to minimize the width of the opening to maintain as much structural integrity of the penetrating member as possible, so that it can be kept small in size.

Figure 13:
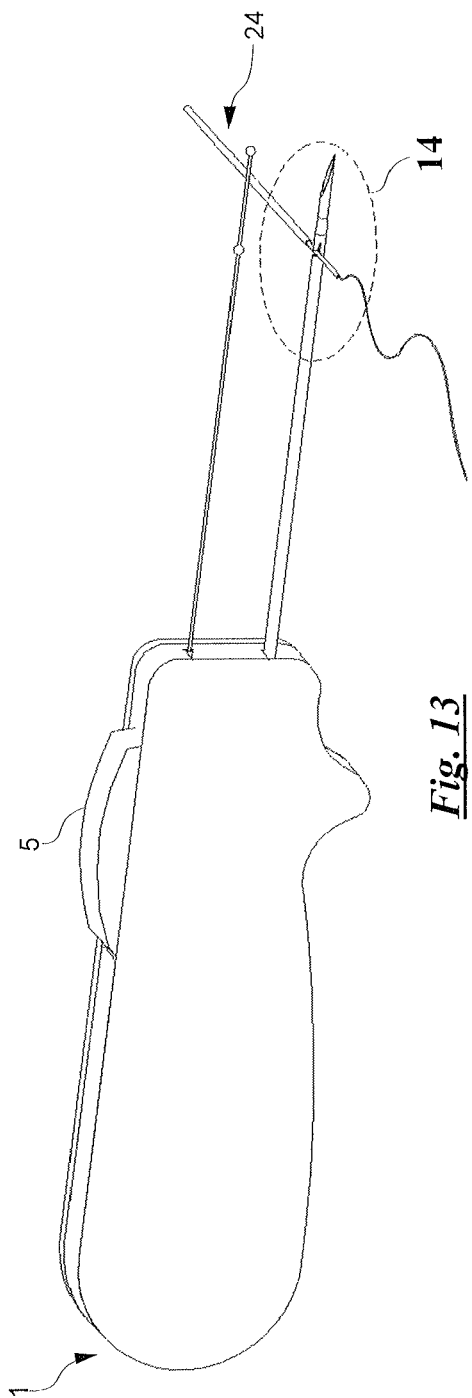
FIG. 13 is an isometric view of the narrow cannula of a tethered cannula in the vertical slot of the engagement feature of the engagement tool with the actuator depressed.
Figure 14:
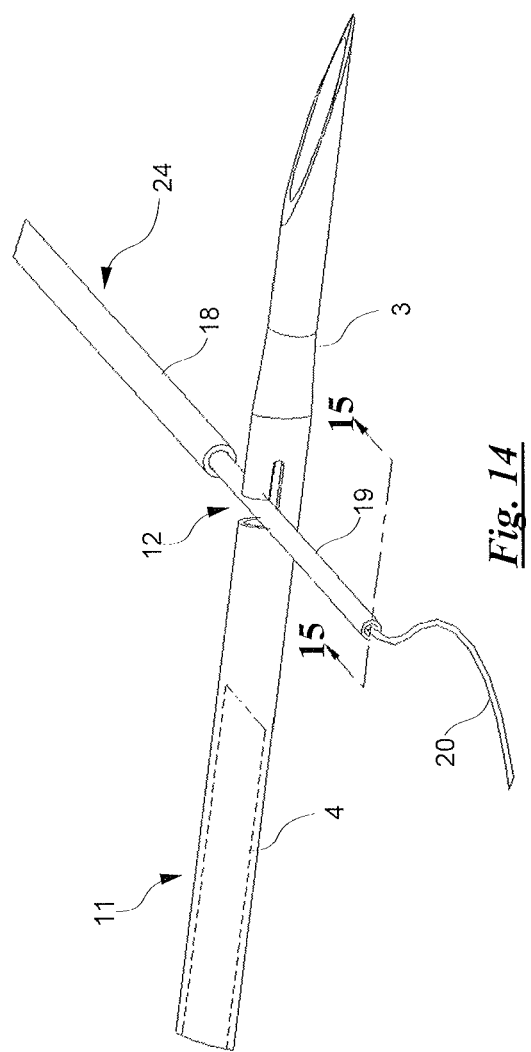
FIG. 14 is an enlarged isometric view of region 14 of FIG. 13 showing the narrow cannula of the tethered cannula in the vertical slot of the engagement feature.
Figure 15:
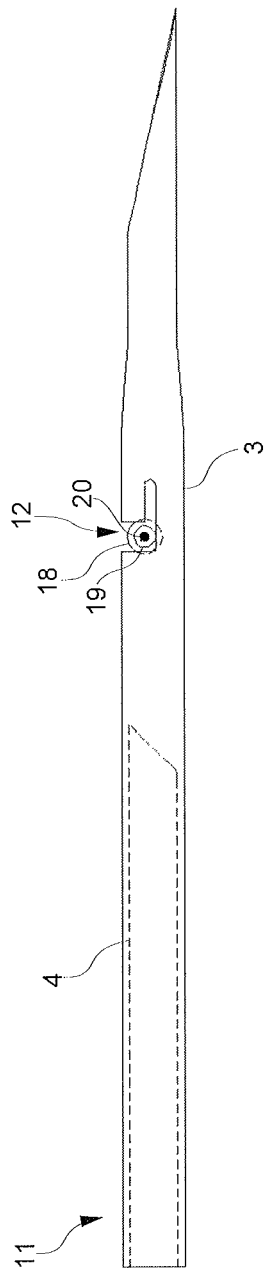
FIG. 15 is a plan view of FIG. 14.

Referring next to FIG. 13 and the enlarged view of zone 14 shown in FIGS. 14 and 15, the engagement tool is shown with the actuator 5 depressed and the capture mechanism 4 retracted. In a preferred sequence, the outer cannula 18 is held in contact with the penetrating member 3 at the engagement feature 12. When the capture mechanism 4 is retracted, the tethered cannula 18 is withdrawn in the orientation shown until the narrow cannula 19 can enter the vertical slot in the engagement feature 12. Again, while a vertical slot could be made to have a sufficient size to accommodate the outer cannula 18, sizing the slot to only accommodate a narrow cannula 19 allows the strength and the size of the penetrating member to be improved, as previously discussed.

Figure 16:
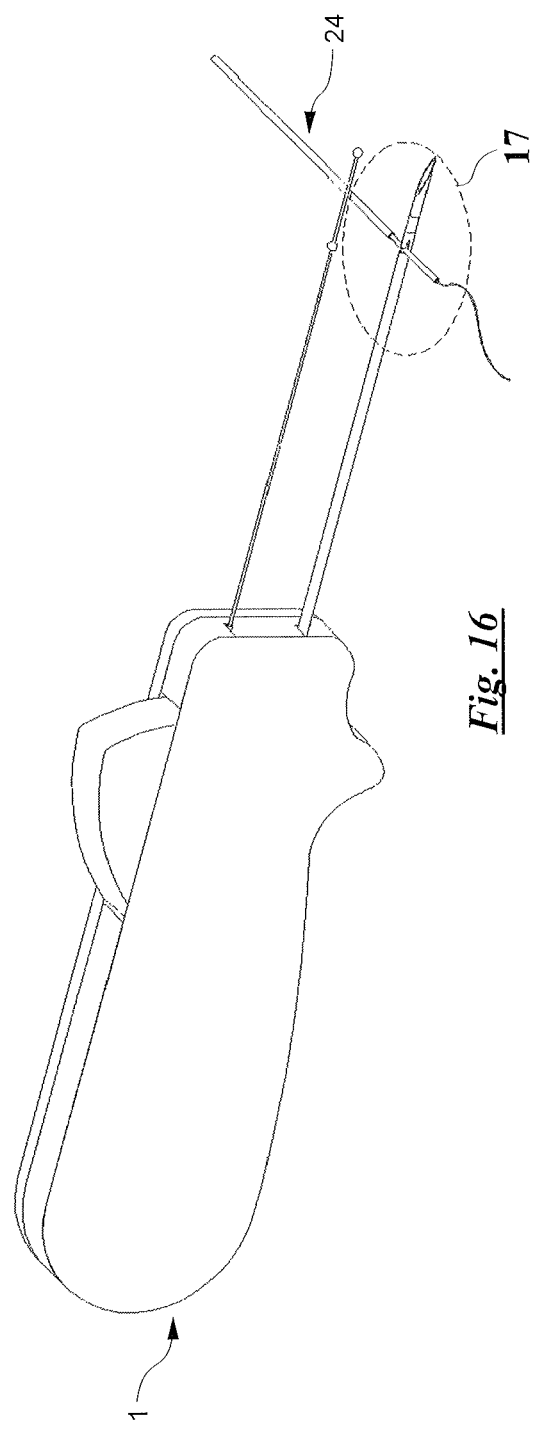
FIG. 16 is an isometric view of the engagement tool with the actuator released and the narrow cannula captured in the engagement feature.
Figure 17:
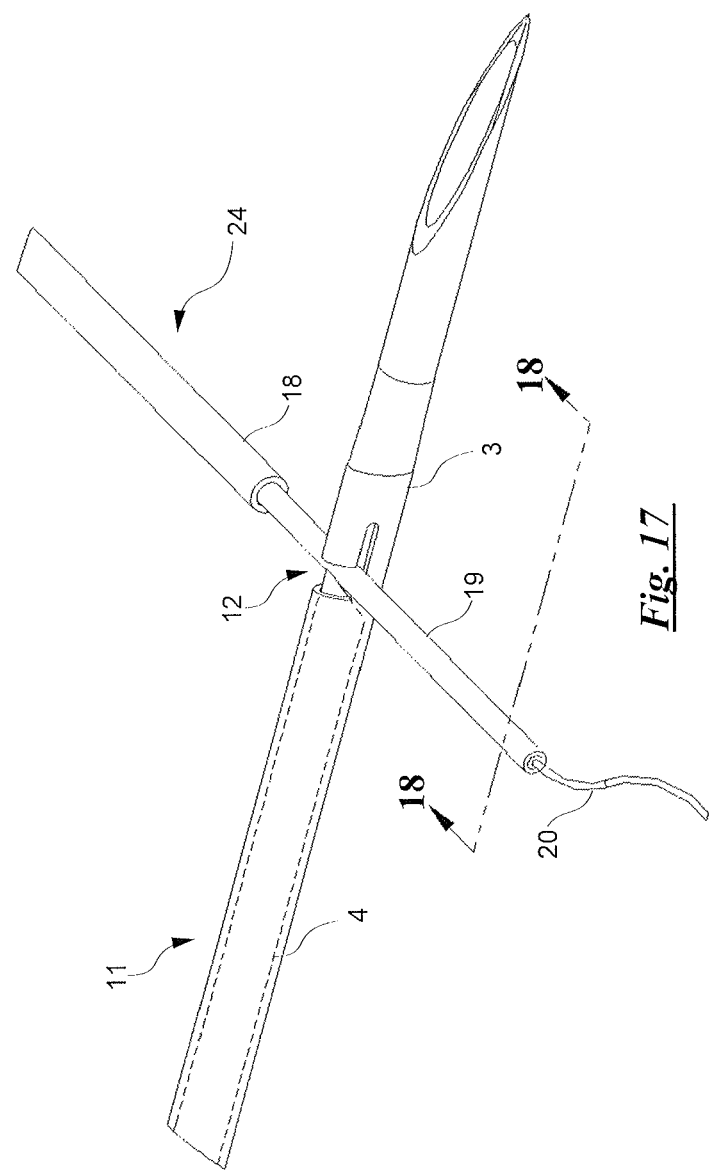
FIG. 17 is an isometric view of the enlarged region 17 of FIG. 16 showing the capture mechanism retaining the narrow cannula in the engagement feature.
Figure 18:
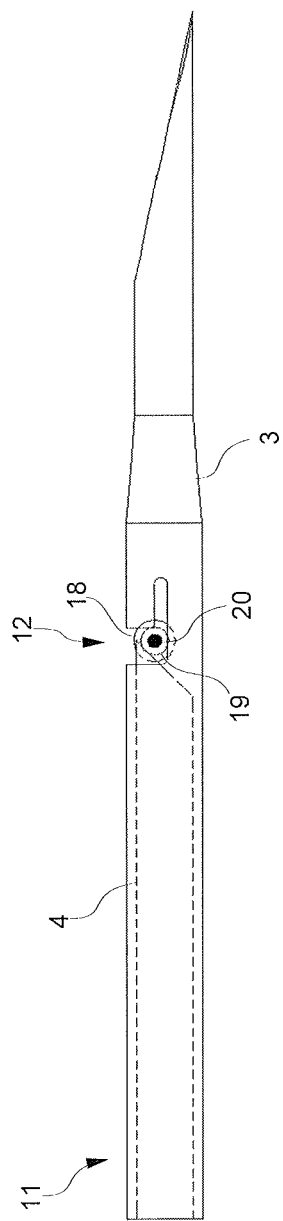
FIG. 18 is a plan view of FIG. 17.
Figure 19:
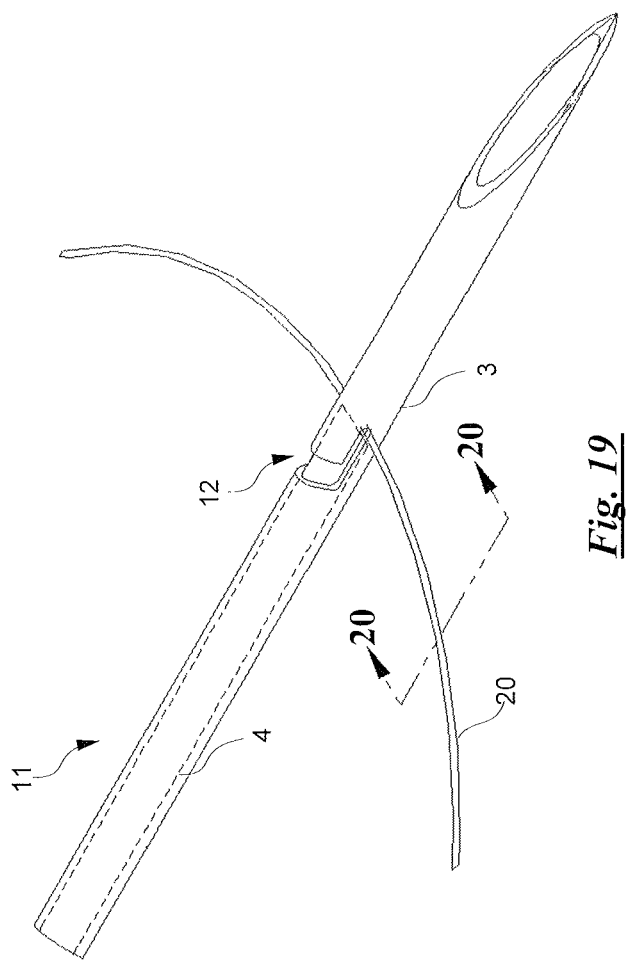
FIG. 19 is an isometric view of a strand captured in the engagement feature.

At this point the actuator 5 is released, as shown in FIG. 16, and the capture mechanism advances to capture the narrow cannula 19 as shown in the enlarged views of the region 17 shown in FIGS. 17 and 18. The angled tip of the capture mechanism 4 then captures the narrow cannula 19 in the engagement feature 12 so it cannot be vertically removed from the engagement feature. In the preferred embodiment, the horizontal slot of the "L" shaped engagement feature is too small to receive the narrow cannula 19. However, as the narrow cannula 19 is axially withdrawn, the strand 20 can enter the engagement feature and is driven by the capture mechanism along the small horizontal slot of the "L", into the forward position shown FIG. 19. The stroke of the capture mechanism 4 is preferably limited so that a gap is left at the distal end of the horizontal slot of the "L" shaped engagement feature to allow several sutures to freely slide through this region without being impinged upon by the capture mechanism. FIG. 20 shows a plan view showing two strands 20 at the distal end of the horizontal slot of the engagement feature, with the capture mechanism 4 in its extended position. It is also possible to have the capture mechanism extend further, to engage the strand, if desired.

An additional advantage of this configuration is that subsequently tethered cannulas can be engaged and captured without risking of losing the first strand from the first tether. This is because the first tether is always blocked from escaping the engagement feature by either the capture mechanism, a second outer cannula or a second narrow cannula.

FIG. 21 shows an alternative embodiment of the engagement mechanism. In this arrangement, the penetrating member 4a includes an engagement feature 12a which is "V" shaped. The capture mechanism 4a is a hook-like device which, in the state shown and when retracted, can capture the tethered cannula positioned in transverse alignment with the engagement feature 12a. The "V" shaped engagement feature of the penetrating member is less likely to catch tissue as it passes through, so there is less need to block the engagement feature during penetration or withdrawal, as is contemplated with the preferred embodiment. As with the preferred embodiment, the penetrating member 3a is again preferably made from a cannula where the section 13a is flattened into an oval cross section in order to maximize the available geometry of the engagement feature 12a.

FIG. 22 shows the region 22 of FIG. 21. Upper portion of the penetrating member are slotted to provide a relief for the hook of the capture mechanism 4a. This allows the dimensions of the hook to be optimized, within the confines of the penetrating member 3a.

FIGS. 23 and 24 show the hook retracted, in a position for capturing a tethered cannula located in the engagement region prior to retraction. It is to be noted that, as an alternative, the hook of the capture mechanism 4a can be oriented to face in the opposite direction as is shown in FIGS. 23 and 24, if desired, to instead face toward the distal tip and begin on the proximal side of the engagement feature. In such as an arrangement, the capture mechanism would extend toward the distal tip to engage a tethered cannula in a similar fashion as was described for the preferred embodiment. In addition, the capture mechanism 4a could be designed with two hooks, one hook facing distally toward the tip and another hook facing proximally away from the tip, so the tethered cannulas could be captured by either retracting or extending the hooks.

As with the preferred embodiment, it is preferred that section 13a of the penetrating member 3a is flattened into an oval in the area of the engagement zone, instead of being round. As in the preferred embodiment, flattening a cannula in this region allows the engagement region to be of a larger dimension. As a further alternative, the entire cannula can be flattened, as well.

Figure 26:
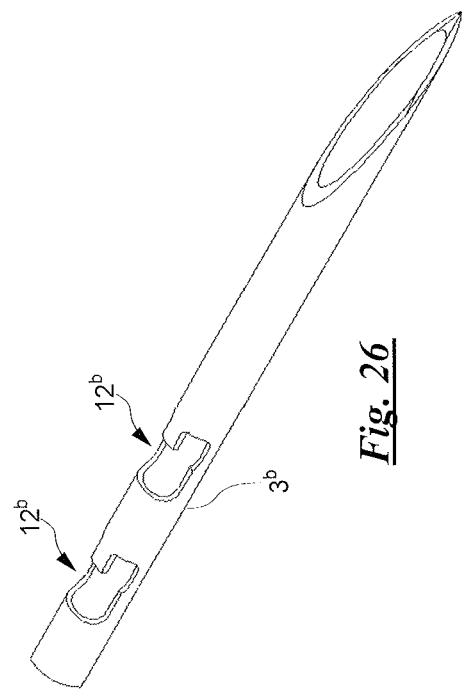
FIG. 26 is an isometric view of the penetrating member of FIG. 25.
Figure 25:
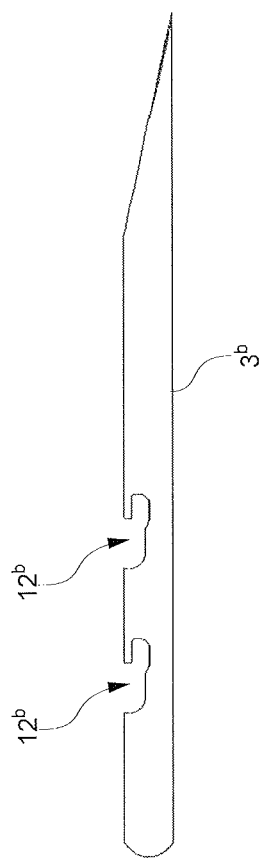
FIG. 25 is a plan view of the penetrating member of an alternative embodiment of an engagement mechanism which couples with a rotating capture mechanism.

FIGS. 25 and 26 show an alternative embodiment illustrating a penetrating member 3b having two engagement features 12b. Such a configuration can be used to interact with a rotating capture mechanism, for example. To be noted is that while the two engagement features 12b are shown with the same overall configuration, it is also possible for the engagement features 12b to have different configurations, if useful for a particular application.

Figure 31:
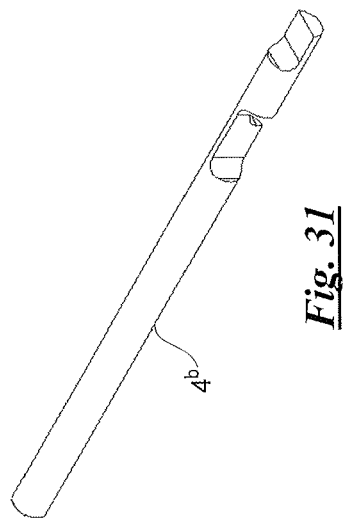
FIG. 31 is an isometric view of the rotating capture mechanism shown in FIGS. 27, 28, 29 and 30.

FIGS. 27 to 30 show an alternative embodiment capture mechanisms 4b which is rotated by 90 degrees in each progressive figure, corresponding to the rotational capture mechanism 4b shown in FIG. 31.

Figures 27, 28, 29, 30:
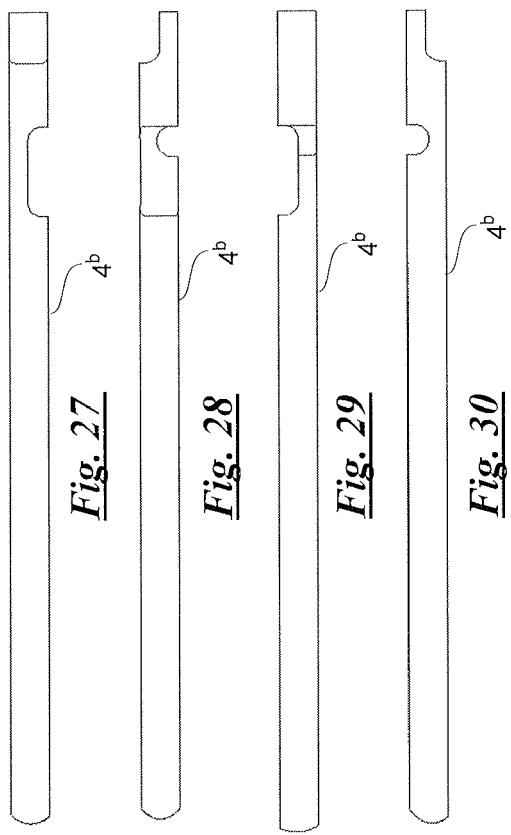
FIGS. 27, 28, 29 and 30 are plan views of a rotating capture mechanism which couples with the penetrating member shown in FIG. 25, with each view progressively rotated by 90 degrees.

FIG. 32 shows the capture mechanism 4b inserted into the penetrating member 3b, with the capture mechanism oriented as shown in FIG. 28. By progressively rotating the capture mechanism, in this case by 90 degrees, the two engagement features 12b can be selectively closed off from receiving a tethered cannula, or open to receive a cannula, and then closed off again to capture a tethered cannula or a strand in the forward section of either of the engagement features.

In FIG. 32, the forward-most engagement feature 12b, closest to the distal tip of 3b, is shown in the open configuration, ready to receive a tethered cannula within the forward notch of the engagement feature, which is available to receive a narrow cannula.

In FIG. 33, the capture mechanism 4b is rotated by 90 degrees, as shown in FIG. 29. In this orientation, a narrow cannula or strand (not shown) are captured in the forward notch of the engagement feature if present in the notch before rotation. In this orientation, the rear-most engagement feature 12b, which is farther from the distal tip, is open to receive a second tethered cannula.

In FIG. 34, the capture mechanism 4b is rotated by another 90 degrees, as is shown in FIG. 30. In this orientation, the forward notches of both of the engagement features 12b have openings where a narrow cannula or strand can be captured by the capture mechanism 4b.

FIGS. 35 and 36 show an alternative embodiment capture mechanism 4c having a flexible latch. The latch is preferably made from a flexible wire, in the configuration shown. However, other constructions can also be developed, if appropriate for a particular application. The curvature of the latch in the vicinity of the engagement feature 12c provides a smooth transition on the outer surface of the penetrating member 3c, to prevent tissue from being snagged by the engagement feature. The guard 25c is shown in a forward position, which prevents the latch from opening by making it difficult to flex. FIGS. 37 and 38 show the capture mechanism 4c with the guard 25c retracted, which then allows the capture mechanism 4c to flex, for opening the engagement feature 12c. FIGS. 39 and 40 show the capture mechanism 4c bent down to open the engagement feature 12c for receiving a tethered cannula or a strand. If desired, the capture mechanism 4c can be configured with a preferential bend so that when the guard 25c is retracted the capture mechanism 4c bends inwardly as shown, or the flexible capture mechanism 4c can be configured to bend outwardly, to continue to block the engagement feature with the guard 25c until it is bent inwardly by a force applied to it from a tethered cannula or a strand.

FIGS. 41 and 42 show a further alternative embodiment of a capture mechanism 4d and a guard 25d. In this embodiment, the guard 25d is fixed and preferably cooperates with the capture mechanism 4d when placed in alignment with the guard 25d. While the capture mechanism 4d is shown as a flexible wire, other constructions can also be implemented. Alignment of the capture mechanism 4d with the guard 25d can be achieved by reciprocating the capture mechanism 4d, by rotating the capture mechanism 4d or by configuring the capture mechanism 4d to bend out of the way responsive to a force applied to the capture mechanism 4d. For example, FIGS. 43 and 44 show the capture mechanism 4d being bent inwardly, as would occur responsive to a force applied to it, for example, from a tethered cannula or a strand, which could then enter the engagement feature 12d. As a further alternative, the capture mechanism 4d can be retracted to provide an opening for the engagement feature, instead of using a capture mechanism 4d which is flexible.

FIGS. 45 and 46 show an alternative embodiment capture mechanism 4e and guard 25e. The guard 25e is fixed and provides a surface for receiving the capture mechanism 4e. The capture mechanism 4e is shown as a small diameter wire, but can also be made from other thin-shaped materials supportable between the upper surface of the guard 25e and the penetrating member 3e. In the configuration shown, the capture mechanism 4e is retractable, and both engagement features 12e are available to receive a tethered cannula or a strand.

FIGS. 47 and 48 show the capture mechanism 4e of FIGS. 45 and 46 advanced so that the rear or proximal engagement feature 12e is closed. A tethered cannula or a strand located in the rear engagement feature 12e before such advancement would then be captured between the capture mechanism 4e and the rear engagement feature 12e. FIGS. 49 and 50 show the capture mechanism 4e advanced further, so that a tethered cannula or a strand present in the forward (or distal) engagement feature 12e would similarly be captured as previously described.

FIGS. 51 and 52 show an alternative embodiment engagement mechanism 11f and capture mechanism 4f. The capture mechanism 11f is formed as a flexible hook, and is preferably made from a wire, although other constructions are also possible. The penetrating member 3f includes a slot through which the capture mechanism 4f can pass, by flexing outwardly responsive to a force applied by a tethered cannula or strand entering the engagement feature 12f. FIGS. 53 and 54 show the capture mechanism 4f flexing outwardly through the slot. Once the tethered cannula or strand is moved to the forward notch of the engagement feature 12f, the capture mechanism 4f returns to the position shown in FIG. 51 to capture the tethered cannula or strand. In such embodiments, it is advantageous for the capture mechanism 4f to normally flex inwardly. The guard 25f in this embodiment is shown to provide a surface for the capture mechanism 4f to abut against when inwardly positioned, as shown in FIG. 52.

FIGS. 55 and 56 show an alternative embodiment engagement mechanism 11g and capture mechanism 4g. The capture mechanism 4g includes a flexible hook which is preferably bent so the hook will elevate through a slot formed in the penetrating member 3g. A guard could also be used to force the capture mechanism 4g outwardly, through the slot in the penetrating member 3g, if desired. FIGS. 57 and 58 show the capture mechanism 4g in an outwardly directed position. A tethered cannula in the engagement feature 12g will flex the guard over the tethered cannula and then capture the tethered cannula with the hook in the engagement feature 12g.

Figure 59:
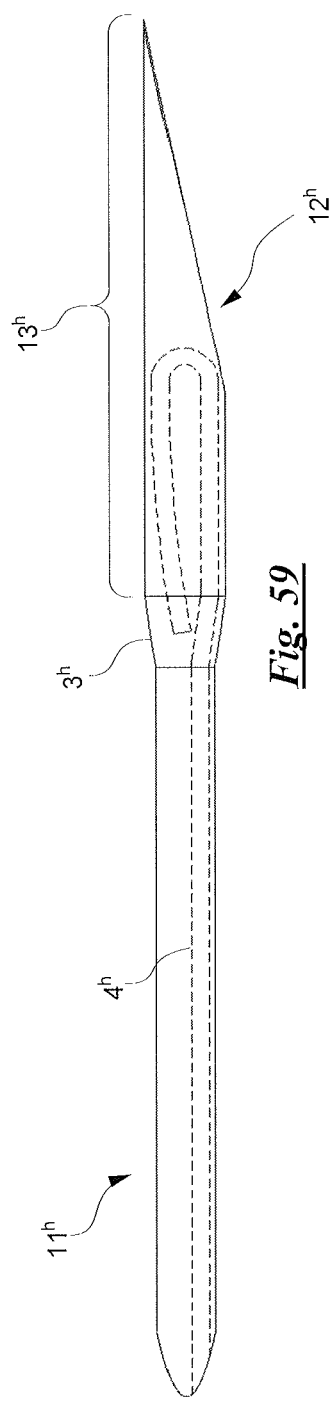
FIG. 59 is a plan view of an alternative embodiment of an engagement mechanism where the capture mechanism is designed to protrude from the distal tip of the penetrating member.

FIG. 59 shows an alternative embodiment capture mechanism 4h and penetrating member 3h, with the capture mechanism 4h retracted within the penetrating member 3h. Advancing the capture mechanism 4h, as shown in FIGS. 60 and 61, creates an engagement feature 12h between the penetrating member 3h and the capture mechanism 4h, in a position ready to receive a tethered cannula or a strand. FIGS. 62 and 63 show the capture mechanism 4h partially retracted into the penetrating member 3h, in a position where a tethered cannula or strand is preferably captured, for example, by deflecting the capture mechanism 4h away from the engagement feature 12h.

Figure 64:
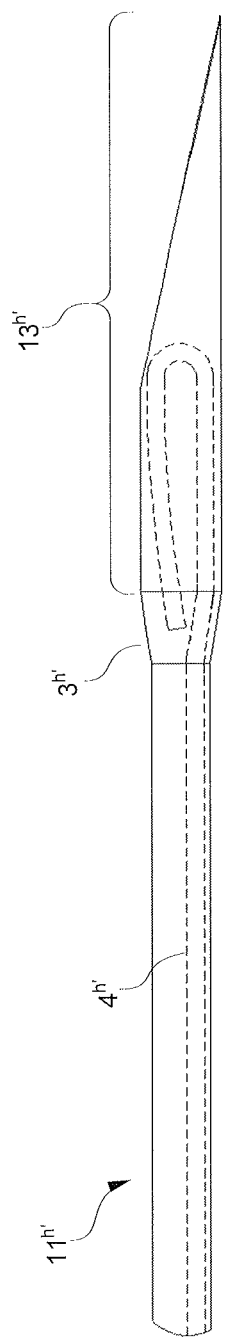
FIG. 64 is a plan view of an alternative embodiment of an engagement mechanism similar to the embodiment of FIG. 59 but where the penetrating member shows a beveled tip rotated by 180 degrees.

FIG. 64 shows an alternative embodiment capture mechanism 4h' retracted in a penetrating member 3h' having a beveled point rotated 180 degrees from the orientation shown in FIG. 60. In this embodiment, the capture mechanism 4h' is again shown as a flexible wire, although other flexible constructions can also be implemented, if desired. FIGS. 65 and 66 show the capture mechanism 4h' in an extended position, forming an engagement feature 12h' between the penetrating member 3h' and the capture mechanism 4h'. In this configuration, the engagement feature 12h' is open and ready to receive a tethered cannula or a strand. FIGS. 67 and 68 show the capture mechanism 4h' retracted into the penetrating member 3h', in a position where a tethered cannula or strand is preferably captured, for example, by deflecting the capture mechanism 4h' away from the engagement feature 12h'.

FIG. 69 shows an alternative embodiment engagement mechanism 11i which includes a penetrating member 3i having a helical coil section. Multiple engagement features 12i are developed between the helical coils. For purposes of simplicity, only the engagement features are identified on the top side of the penetrating member 3i, even though additional engagement features are available between the helical coils from the bottom side of the penetrating member 3i. The capture mechanism 4i is shown with a bullet nose in the front, and is retracted relative to the engagement features 12i, which are then open and available for transverse engagement with a tethered cannula or strand. Other configurations for the tip of the capture mechanism 4i are also possible, although the angled tip of the preferred embodiment is presently considered preferred to facilitate the capture of a larger diameter tethered cannula.

FIG. 70 shows the capture mechanism 4i inserted through the engagement features 12i of the helical coils of the penetrating member 3i. As previously indicated, a tethered cannula or a strand can be positioned between and within one of the engagement features 12i defined by the helical coils. An advancing capture mechanism 4i can come in contact with and capture a tethered cannula or strand. By using a suitably narrow cannula, the tip of the capture mechanism 4i can capture the cannula between the coils. The dimensions of the capture mechanism 4i can be selected to be sufficiently small to allow the capture mechanism to continue to advance, or to stop on the narrow cannula until the narrow cannula is withdrawn and a strand is captured between the bottom surface of the capture mechanism 4i and the helical coils. It is preferred that the dimensions of the capture mechanism 4i are sufficiently small relative to the inner dimensions of the helical coils to allow a strand to pass freely while captured. Alternatively, the helical coils could be made flexible, to expand by flexing as the capture mechanism captures the strand, although this is not presently considered to be the preferred configuration for this.

FIGS. 71, 72 and 73 show an alternative embodiment engagement mechanism 11j which is similar in function to the engagement mechanism 11c shown in FIGS. 35 and 36. The penetrating member 3j includes an engagement feature 12j. The capture mechanism 4j is shown constructed of a flexible wire but, as previously indicated, can be of some other construction. The guard 25j in the position shown in FIG. 71 prevents the capture mechanism 4j from flexing inwardly to prevent a tethered cannula or strand from entering the capture zone of the engagement feature. FIG. 72 shows the guard 25j retracted and the capture mechanism 4j in a position in which a downward force applied from a tethered cannula or a strand will cause the capture mechanism 4j to flex inwardly to open the engagement feature for receiving a narrow tethered cannula or a strand, as is shown in FIG. 73 (tethered cannula or strand not shown). To be noted is that the front end of the guard 25j can be angled, as shown, to lift a narrow cannula or a tether into the forward slot of the engagement feature.

Figure 74:
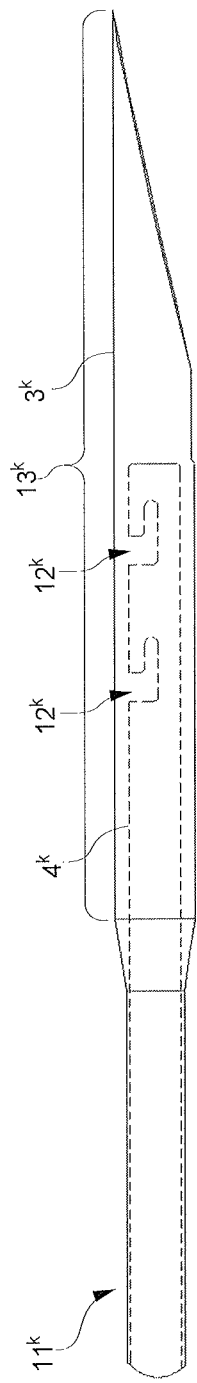
FIGS. 74, 75, 76 and 77 are progressive plan views of an alternative embodiment of an engagement mechanism showing a capture mechanism with engagement features which can protrude from the end of the penetrating member in various positions of extension and retraction for engagement and capture.
Figure 75:
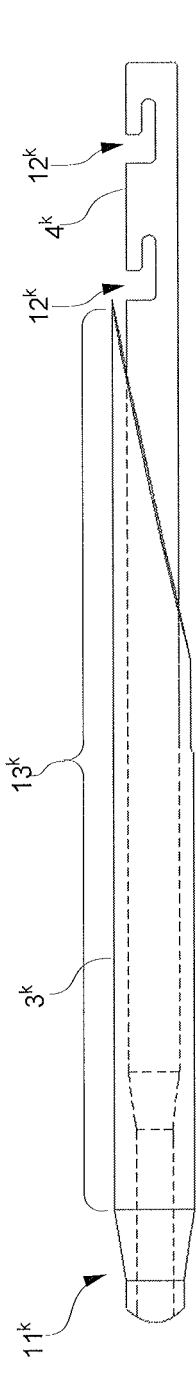
Figure 76:
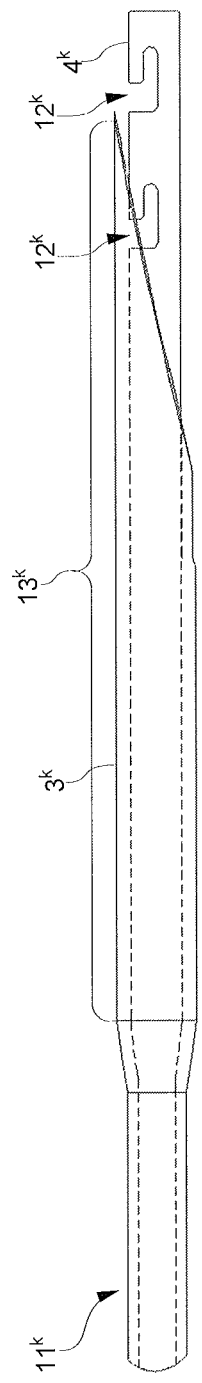
Figure 77:
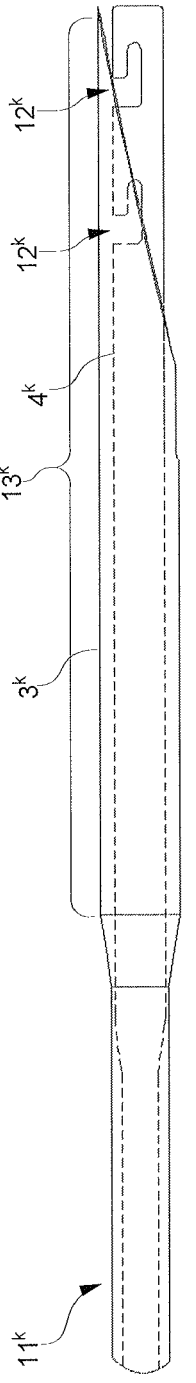
Figure 78:
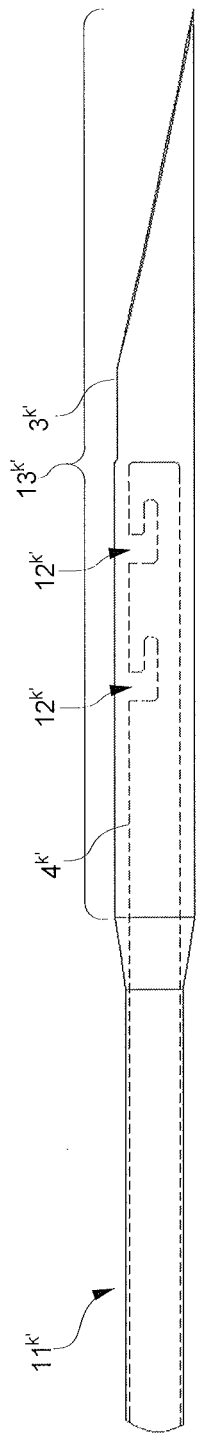
FIGS. 78, 79, 80 and 81 are progressive plan views of an alternative embodiment of an engagement mechanism showing a capture mechanism with engagement features which can protrude from the end of the penetrating member in various positions of extension and retraction for engagement and capture, with the bevel on the end of the penetrating member rotated 180 degrees from FIGS. 74, 75, 76 and 77.
Figure 79:
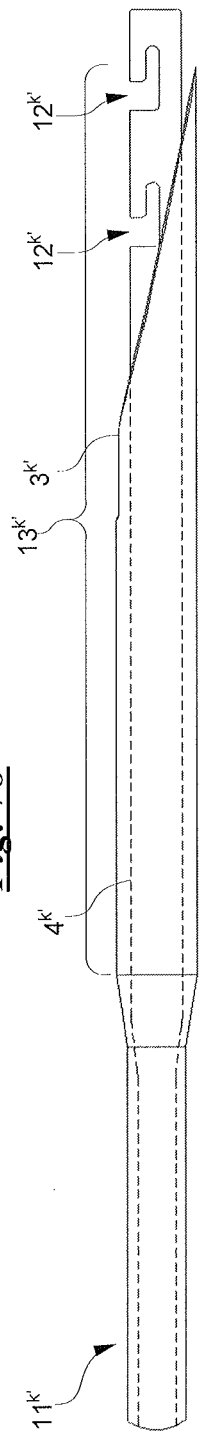
Figure 80:
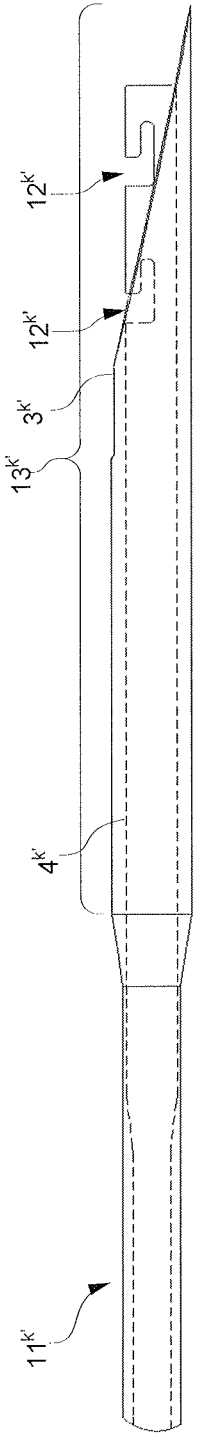

FIGS. 74, 75, 76 and 77 show an alternative embodiment engagement mechanism 11k which illustrates a capture mechanism 4k having multiple engagement features 12k. The illustrated penetrating member 3k is made from a cannula with a flattened distal tip, to again provide the advantage of allowing larger dimensions for the engagement features. FIG. 74 shows the capture mechanism retracted. FIG. 75 shows the capture mechanism extended to receive a tethered cannula or a strand. FIG. 76 shows the proximal engagement feature 12k retracted to a position where a first tethered cannula or strand would be captured, leaving the distal engagement feature 12k available to receive another tethered cannula or strand, if desired. FIG. 77 shows the capture mechanism 4k retracted to a position where a tethered cannula or strand can be captured in either or both of the engagement features 12k.

Figure 81:
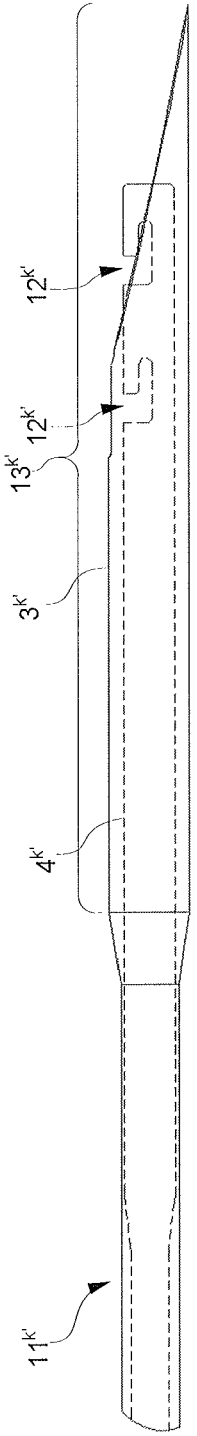

FIGS. 78, 79, 80 and 81 show an alternative embodiment engagement mechanism 11k' which is similar to the engagement mechanism 11k in FIGS. 74 to 76. The penetrating member 3k' is shown with a pointed tip oriented with the bevel rotated 180° relative to the tip shown in FIGS. 74 to 76. In this orientation, as shown in FIG. 81, the proximal engagement feature 12k' is behind the penetrating member 3k' when the capture mechanism 4k' is retracted to this position. With this arrangement, a tethered cannula could not be fully retracted to this position if located in the slot of the proximal engagement feature 12k'. However, a strand would be able to bend between the capture mechanism 4k' and the penetrating member 3k' if a sufficient gap is provided between the capture mechanism 4k' and the penetrating member 3k' for a given strand thickness and bend radius.

FIGS. 82, 83, 84 and 84 show an alternative embodiment engagement mechanism 11k" which is similar to the engagement mechanisms 11k and 11k'. In this embodiment, the penetrating member 3k" is shown with a contoured tip. The advantage of this arrangement is best illustrated in FIG. 85, which shows the capture mechanism 4k" retracted to a position where tethered cannulas or strands positioned in transverse alignment within the engagement features 12k" prior to retraction, could be captured in the engagement features. In this position, the engagement features 12k" are not fully blocked by the penetrating member 3*k*", which enables the tethered cannulas to be captured, and for the strands to be captured without necessitating bending of the strand between the walls of the capture mechanism and the penetrating member. This has the advantage of capturing a strand without exposing the strand to cutting forces that could occur if the strand is forced against a sharp bevel, either by retraction of the capture mechanism or by the insertion or withdrawal of the penetrating member with a strand present in a captured engagement feature. In FIG. 85, the engagement feature 12*k*" in the distal position is in a location where a captured strand would not encounter a cutting force from a sharp edge of the penetrating member 3*k*" during subsequent insertion or extraction of the penetrating member 3*k*" along its axis.

FIGS. 86 and 87 show an alternative embodiment engagement mechanism 11*l* which is similar to the engagement mechanism 11*c* shown in FIGS. 35 and 36, except that there is no guard and the capture mechanism 4*l* is a latch capable of flexing to provide access to the engagement feature 12*l* when an inwardly directed force from a tethered cannula or strand is applied against it, as is shown in FIG. 87 (tethered cannula or strand not shown. In this embodiment, when a narrow tethered cannula or strand slides into the forward horizontal notch of the engagement feature, the latch releases and returns to the position shown in FIG. 86, and the tethered cannula or strand is captured in the engagement feature by the latch.

FIGS. 88 and 89 show an alternative embodiment engagement mechanism 11*m* including a penetrating member 3*m* with an engagement feature 12*m* having a capture mechanism 4*m* which is inflatable. FIG. 88 shows the capture mechanism 4*m* deflated, with the engagement feature 12*m* open to receive a tethered cannula or strand. FIG. 89 shows the capture mechanism 4*m* inflated, for example, with a fluid or a gas, through an inflation tube 26*m*, which then closes of the engagement feature. As shown in FIG. 89, a tethered cannula or strand in the forward notch of the engagement feature 12*m* would be captured by the inflated capture mechanism.

FIGS. 90 and 91 show an alternative embodiment engagement mechanism 11*n* including a penetrating member 3*n* with an engagement feature 12*n*. The capture mechanism 4*n* and the guard 25*n* are attached to a control rod 27*n*. FIG. 90 shows the control rod 27*n* in a forward position, in which the guard 25*n* will close off the engagement feature 12*n* from receiving a tethered cannula or strand. FIG. 91 shows the control rod retracted, with the capture mechanism 4*n* flexing inwardly, responsive to an inwardly directed force exerted by a tethered cannula or strand on the capture mechanism 4*n* (tethered cannula or strand not shown). As the tethered cannula or strand then moves into the forward notch of the engagement feature 12*n*, the capture mechanism 4*n* will flex outwardly and capture the tethered cannula or strand within the engagement feature 12*n*.

FIGS. 92 and 93 show an alternative embodiment engagement mechanism 11*o* including a penetrating member 3*o*, which is shown as a cannula with engagement features 12*o*, and a capture mechanism 4*o* including a coil spring which resides in the penetrating member 3*o*. In FIG. 92, the coil spring is attached to a fixation location 28*o*. In this configuration, multiple engagement features 12*o* are shown between the coils in the section of the penetrating member having a relief in the penetrating member 3*o*. For the case where the spring is a tension spring, if the spring is under tension the gap between the exposed coils will widen, and the engagement features 12*o* will be available to receive a tethered cannula or strand. In FIG. 93, the capture mechanism 4*o* is shown with the coil spring no longer in tension. In this configuration, the pitch between the spring coils is selected to capture a tethered cannula or strand between the coils. If needed, an additional compressive force can be applied to the spring to further compress the coils and capture a tethered cannula or strand. The spring used with the capture mechanism 4*o* can also be a compression spring, rather than a tension spring, and in such case would initially be open to receive a tethered cannula or strand, as shown in FIG. 92, followed by the application of a force to the spring to compress it for capturing a tethered cannula or strand, as shown in FIG. 93.

FIGS. 94 and 95 show an alternative embodiment engagement mechanism 11*o*'. As with engagement mechanism 11*o*, a capture mechanism 4*o*' includes coils with a fixation location 29*o*', and the device functions in a similar manner to the engagement mechanism 11*o*', with the main difference being that the coils in capture mechanism 4*o*' are wrapped around the outside of the penetrating member 3*o*' instead of being located inside the penetrating member 3*o* described in FIGS. 92 and 93. For the engagement mechanism 11*o*', the penetrating member 3*o*' can be solid, if desired.

FIGS. 96 and 97 show an alternative embodiment engagement mechanism 11*o*" including a penetrating member 3*o*" and a capture mechanism 4*o*" which includes a coil. FIG. 96 shows plural engagement features 12*o*" which are produced between the coils protruding from the distal tip of the penetrating member 3*o*". In this state, the engagement features 12*o*" are available to receive a tethered cannula or a strand. FIG. 97 shows the capture mechanism 4*o*" partially retracted. A strand residing in an engagement feature 12*o*" will be caught between the coils and the interior of the penetrating member 3*o*" as the capture mechanism is retracted inside the penetrating member.

Figure 98:
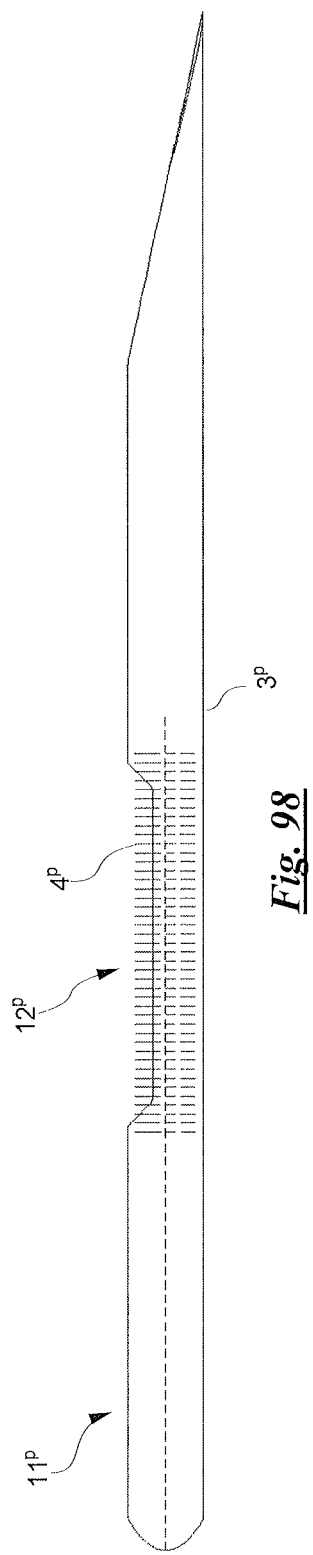
FIG. 98 is a plan view of an alternative embodiment of the engagement mechanism with a capture mechanism which includes a brush which when rotated will engage a strand by grabbing the suture and winding it around the brush.

FIG. 98 is a plan view of an engagement mechanism 11*p* having a penetrating member 3*p* with an engagement feature 12*p* and a capture mechanism 4*p* which includes a small brush in the region of the engagement feature. The brush is designed to rotate inside the penetrating member. With a strand positioned in transverse alignment in the engagement feature, against the brush, the brush is rotated to capture the strand by winding it around the brush. The strand can be initially positioned at the engagement feature with a tethered cannula, and if so, the tethered cannula must be withdrawn to expose the strand directly to the brush of the capture mechanism 4*p*.

FIGS. 99, 100, 101 and 102 are plan views of an engagement mechanism 11*q* having a penetrating member 3*q* and a capture mechanisms 4*q* including a series of telescoping pieces that can be positioned axially to create engagement features 12*q* between one or more capture mechanisms 4*q* or between a capture mechanism and the penetrating member. A tethered cannula or strand can be positioned in one of the engagement features 12*q* and then captured by the movable telescoping capture mechanism 4*q*. FIGS. 99 to 102 show an example of the progressive positioning of several telescoping capture mechanisms 4*q*. In this illustration, as one telescoping capture mechanism advances to capture a tethered cannula or strand in the engagement region 12*q* distal to the capture mechanism, another engagement region emerges proximally behind it.

FIGS. 103, 104 and 105 are plan views of an engagement mechanism 11*r* including a penetrating member 3*r* with engagement features 12*r* and a capture mechanism 4*r*. The capture mechanism 4*r* includes two hook-shaped regions, one facing forward and one facing rearward. FIG. 103 shows the capture mechanism in a forward position with an engagement feature 12r defined between the rear hook area and the rear of the relief in the penetrating member 3r. In this position, the apparatus is ready to receive a tethered cannula or strand in the rear-most open engagement feature 12r. In FIG. 104, the capture mechanism is retracted, which captures a tethered cannula or strand in the rear engagement feature 12r shown in FIG. 101 and opens up another engagement feature 12r in the front of the forward facing hook of the capture mechanism. FIG. 105 shows the capture mechanism 4r partially advanced to a central position so that both of the engagement features 12r from FIGS. 103 and 104 are closed.

FIGS. 106 and 107 are plan views of an engagement mechanism 11s including a penetrating member 3s, a capture mechanism 4s which includes a magnet, and a strand 20s which includes magnetically attractive particles, such as beads. If the attraction between the magnet and the magnetically attractive particles are strong enough, it is possible that no other engagement features are required. FIG. 107 shows the strand magnetically coupled with the magnetic capture mechanism 4s.

In order to reduce the amount of magnetic attraction required, it may be advantageous to use a penetrating member 3s with an engagement feature coupled with a magnet. For example, a magnet could be used in place of the coil shown in FIGS. 96 and 97 for the capture mechanism, and the magnetic capture mechanism 4s could extend from the distal tip of the penetrating member, contact a magnetically attractive strand in transverse alignment and then, with a magnetic coupling, pull the strand through the penetrating member when the penetrating member is hollow, or retain the strand with the magnetic coupling at the tip of the penetrating member. A magnetic capture mechanism could also capture a strand using magnetically attractive particles within an engagement feature defined by a slot or relief in a penetrating member at a location which is not at the tip.

Figure 108:
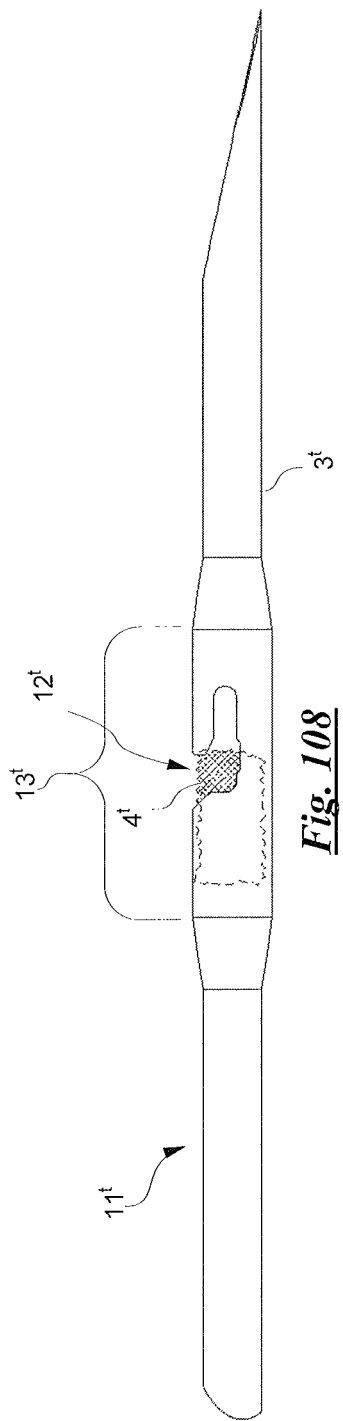
FIG. 108 is a plan view of an alternative embodiment of the engagement mechanism which includes a capture mechanism with a flexible member.

FIG. 108 is a plan view of an engagement mechanism 11t including a penetrating member 3t with an engagement feature 12t and a capture mechanism 4t having a compressible foam-like or rubber-like material. A force applied by a tethered cannula or strand at the engagement feature 12t will compress the capture mechanism and allow the tethered cannula or strand to slip into the horizontal forward notch of the engagement feature.

FIGS. 109 and 110 show an engagement mechanism 11u including a penetrating member 3u with an engagement feature 12u and a capture mechanism 4u formed of a flexible material, such as a wire, that is bent and fixed in position so that when a tethered cannula or strand is forced inwardly into the engagement feature, the capture mechanism deforms and then snaps around the tethered cannula or strand.

FIGS. 111 and 112 show an engagement mechanism 11v including a penetrating member 3v with an engagement feature 12v and a capture mechanism 4v having jaws that can be opened or closed to receive a tethered cannula or strand.

FIGS. 113 and 114 show an engagement mechanism 11w including a penetrating member 3w with an engagement feature 12w and a capture mechanism 4w having a flexible member with barbs. FIG. 113 shows the capture mechanism 4w retracted and the engagement feature 12w open to receive a tethered cannula or strand. FIG. 114 shows the capture mechanism 4w extended to capture a tethered cannula or strand.

FIGS. 115 and 116 show an engagement mechanism 11x including a penetrating member 3x with an engagement feature 12x and a capture mechanism 4x including a spring loaded ball. FIG. 115 shows the spring extended and the engagement feature 12x closed off by the ball. FIG. 116 shows the ball retracted and the engagement feature 12x open to receive a tethered cannula or strand. The spring loaded ball can either be retracted axially by the user, or passively retracted with the application of an inward force produced by a tethered cannula or strand, at the engagement feature and against the front half of the ball.

FIGS. 117 and 118 show an engagement mechanism 11y including a penetrating member 3y with an engagement feature 12y and a capture mechanism 4y which includes a sheath. In FIG. 117, the sheath 4y is extended over the engagement feature, closing it off and preventing it from receiving a tethered cannula or strand. FIG. 118 shows the sheath 4y retracted and the engagement feature 12y open to receive a tethered cannula or strand. The sheath 4y can also be partially extended to capture a tethered cannula or strand in the narrow horizontal notch of the engagement feature 12y.

FIGS. 119 and 120 show an engagement tool 1z including a fluid pathway 30z for dispensing fluid through the tool, which can be useful to administer anesthetic fluids for numbing tissue, and saline solutions for opening pathways through tissue by hydro-dissection. This can be especially useful if the tip of the penetrating member is blunt.

Figure 121:
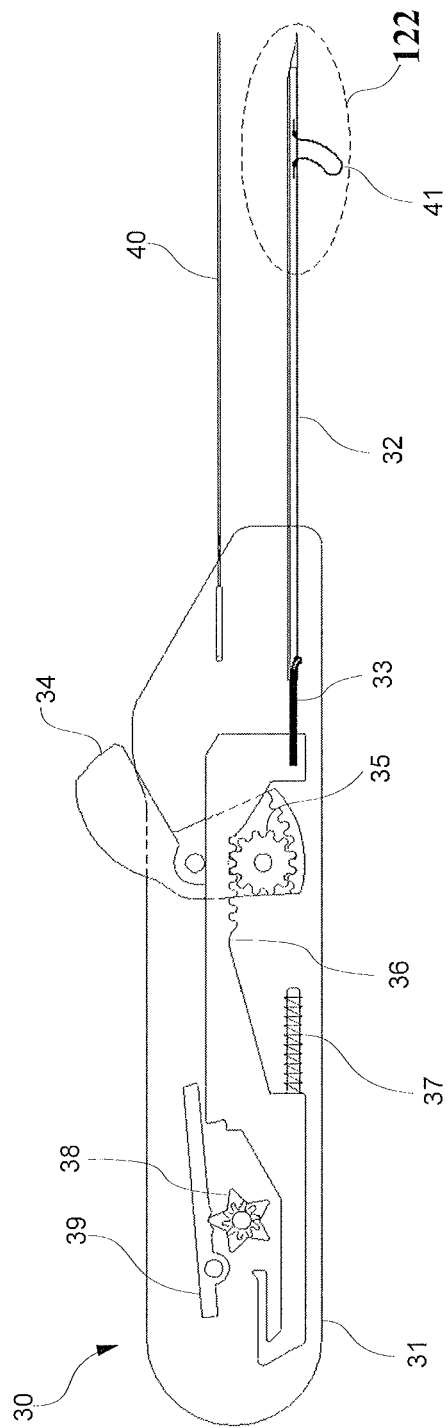
FIG. 121 is a plan view of an embodiment of a routing tool used to place tethered cannulas or strands in position for engagement with the engagement tool.

FIG. 121 shows a preferred embodiment of a routing tool 30 which can be used to position a tethered cannula or strand in transverse alignment with an engagement tool. The preferred embodiment includes a body 31 coupled with a penetrating member 32. The penetrating member 32 is shown with a pointed tip, which can optionally be provided. A blunting mechanism 33 is also preferably provided, and is coupled to a carriage 36 which causes the blunting mechanism 33 to translate along the axis of the penetrating member 32 to blunt the distal tip of the penetrating member 32, as is described, for example, in the above-referenced U.S. patent application Ser. No. 12/384,326, and International Application No. PCT/US2010/000891.

An actuator mechanism 34 is provided which, as shown in FIG. 121, is in a raised position. When the actuator mechanism 34 is depressed, it rotates around a pivot point and teeth on the actuator mechanism engage a gear 35, which engages the linear teeth of the carriage 36 and causes the carriage and the coupled blunting mechanism 33 to advance toward the distal tip of the penetrating member 32. When the carriage advances past a certain point, a flexible arm shown toward the rear of the carriage engages the small teeth of a rotating ratchet 38, rotating the large teeth of the ratchet 38 and allowing the latch 39 to flex or spring downward into a position which prevents the carriage 39 from returning, and compressing a spring mechanism 37 for keeping the carriage engaged against the front of the latch mechanism 39. This ensures that the blunting mechanism is latched into a blunt position, and that a force applied on the tip of the blunting mechanism 33 which extends past the tip of the penetrating member will be resisted by the latch 39 and will not result in the blunting mechanism retracting and exposing the sharp tip. In this state, the compressed spring 37 causes the actuator arm to partially rotate back from its fully depressed position when the actuator arm 34 is released. However the actuator arm 34 is not allowed to fully return to its top-most position because of the latch. Partial return of the carriage allows the flexible arm to travel slightly behind the ratchet mechanism 38 while the blunting mechanism is maintained slightly forward of the tip of the penetrating member 33 and slightly back from a fully forward position. Subsequent depression of the actuator 34 toward a fully forward position causes the rear arm on the carriage to again engage the small teeth of the ratchet 38 to rotate, causing the large teeth of the ratchet 38 to engage the latch 39 and raise it to a position where the carriage 35 is free to return to a rearward position from the force of the compressed spring 37, causing the actuator 34 to raise fully and the blunting mechanism 33 to retract, and exposing the pointed tip of the penetrating member 32. Also shown is an indicator 40 which is intended to remain above the tissue and provide an indication of the location of the distal tip of the penetrating member when hidden from view by tissue.

Figure 122:
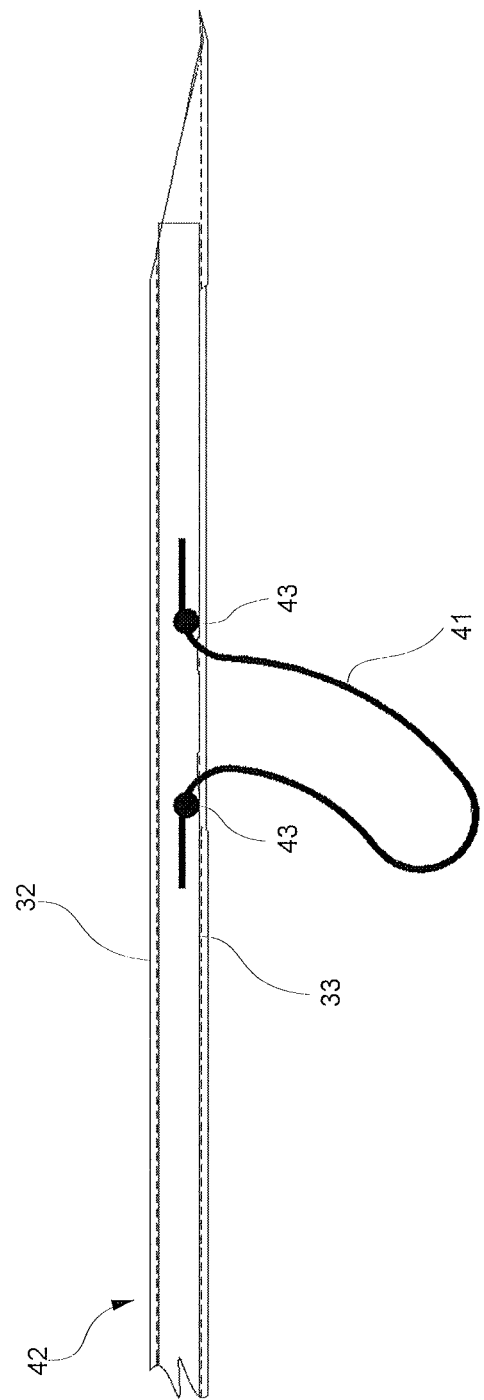
FIG. 122 is a plan view of region 122 of FIG. 121 showing the front section of the penetrating member of the routing tool.

FIG. 122 shows the region 122 shown in FIG. 121 of the front end of the penetrating member 32. In this embodiment, the front end 42 includes the distal tip 32 of the penetrating member, which is shown as a sharp tip having a bevel which is bent slightly inwardly toward the axis of the penetrating member, which is constructed from a cannula. In this embodiment, the blunting mechanism is a cannula 33 which translates inside of the penetrating member. The blunting mechanism is shown in a retracted position, with the sharp tip of the penetrating mechanism exposed. A strand 41 is coupled to the blunting mechanism and forms a loop for subsequent coupling with the strand of a tethered cannula or to a strand not attached to a cannula. The strand 41 preferably passes through two small slots in the blunting mechanism 33, and ends of the strands are retained by the blunting mechanism, preferably by the knots 43 shown, which prevent the strand 41 from being pulled through the slots. The penetrating member 33 preferably includes one or more slots which are aligned with the slots of the blunting mechanism. The slot or slots in the penetrating member 33 are sufficiently long to allow the strand 41 to translate when the blunting mechanism translates from its forward-most position to its rear-most position responsive to operations of the mechanisms associated with the routing tool 30, as previously described.

Figure 123:
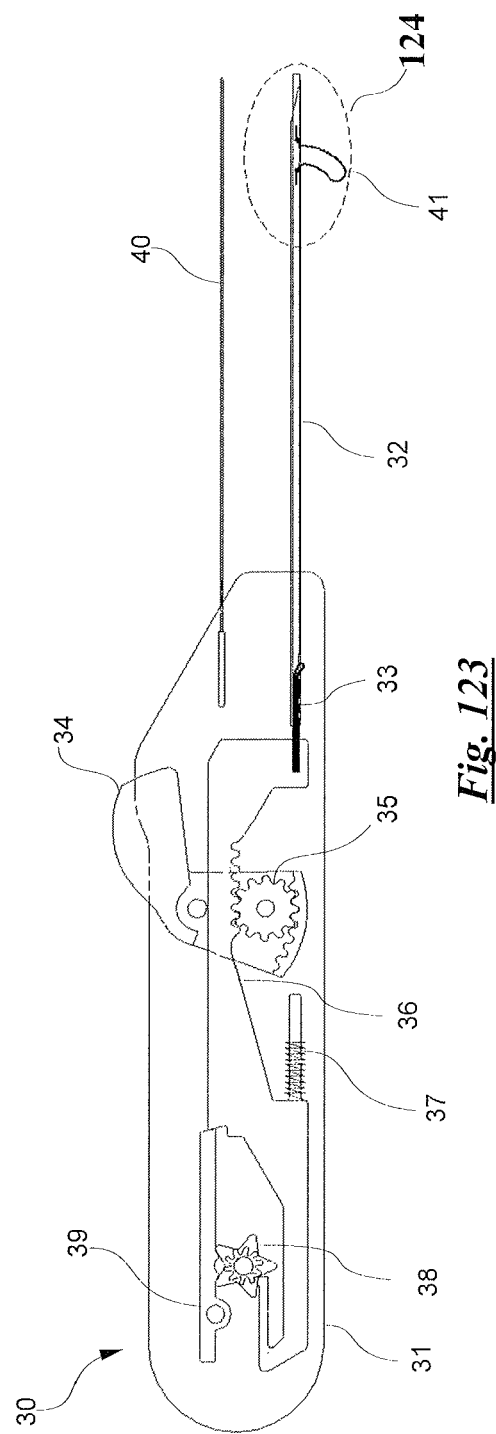
FIG. 123 is a plan view of the routing tool of FIG. 121 where the blunting mechanism of the routing tool is engaged forward and latched into position.
Figure 124:
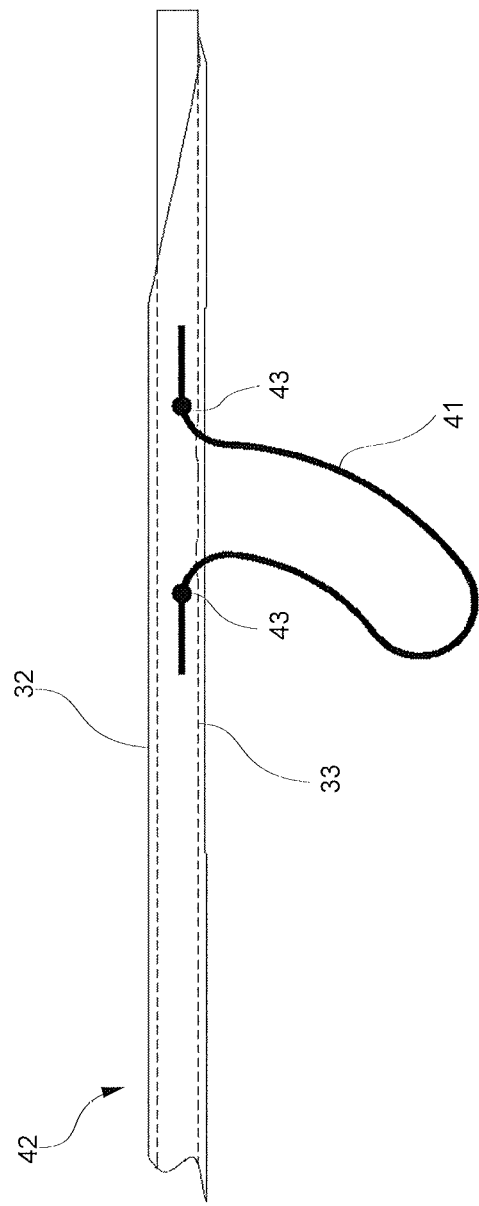
FIG. 124 is a plan view of region 124 of FIG. 123 which shows the blunting mechanism extended passed the point of the penetrating member.

FIG. 123 shows the routing tool 30 with the actuator 34 depressed and in the latched forward position, where the blunting member 33 extends forward of the distal tip of the penetrating member 32. The spring 37 is shown compressed and the latch 39 is shown engaging the carriage 36, which prevents the carriage from fully returning. The ratchet mechanism 38 is shown rotated in a position where the larger teeth of the ratchet allow the latch 39 to lower into the latching position, and the rear arm of the carriage which engages the small teeth of the ratchet 38 is shown just rear of the small teeth of the ratchet. FIG. 124 shows the region 124 of FIG. 124. In this configuration, the outer diameter of the blunting mechanism 33 extends forward of the tip of the penetrating member 32 and contacts the bent tip of the beveled point of the penetrating member so that the tip does not act as a catch point.

Figure 125:
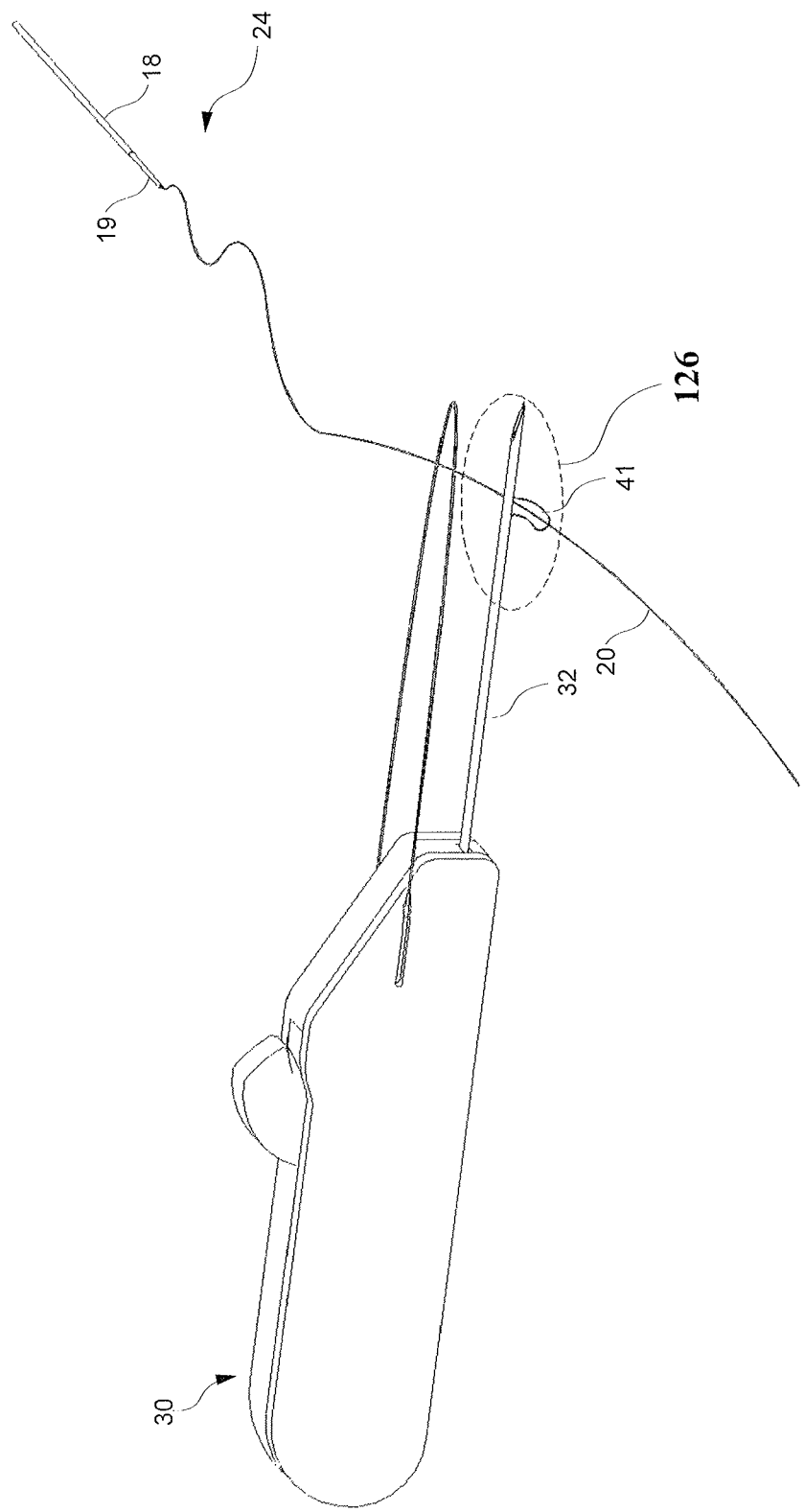
FIG. 125 is an isometric view of the routing tool coupled to a tethered cannula.
Figure 126:
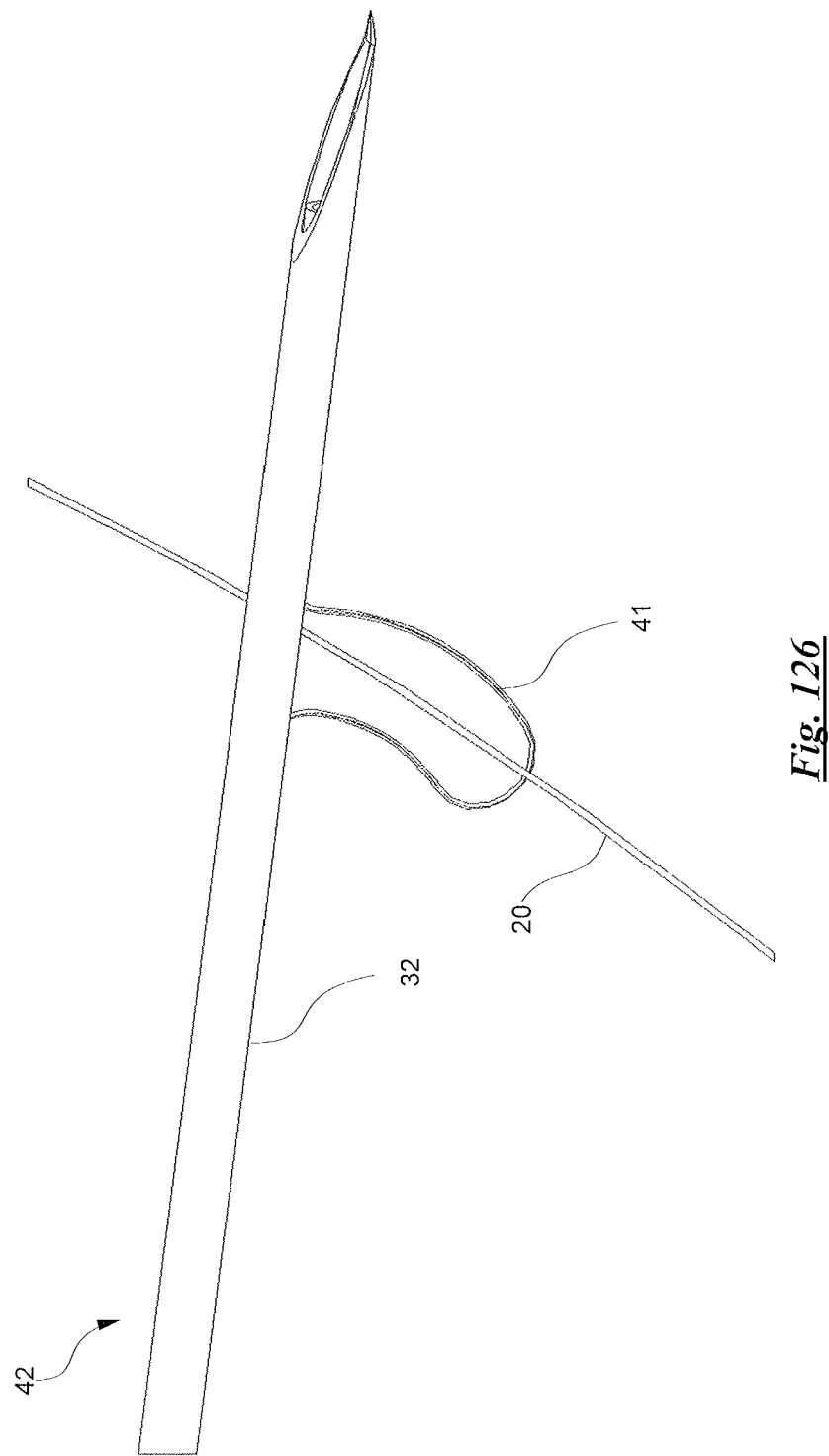
FIG. 126 is an expanded isometric view of region 126 of FIG. 125 showing the coupling of the strand of the tethered cannula to the routing tool.

FIG. 125 shows the routing tool 30 coupled with a tethered cannula 24, through the looped strand 41 of the routing tool and the strand 20 of the tethered cannula 24. By inserting the routing tool through tissue, a pathway is created. A separate strand can be coupled to the routing tool and positioned along this same pathway. In this way, coupling occurs by passing a strand through the loop 41 of the routing tool. Other techniques can also be used to couple a strand to the routing tool, if desired, such as inserting the strand through the lumen of the routing tool, or tying a strand to the routing tool directly or through a strand affixed to the routing tool, or mechanically engaging the strand to the routing tool. FIG. 126 shows the region 126 of FIG. 125, showing the strand 20 passing through the loop of the strand 41.

The routing tool can conveniently be coupled with a strand and, when used in conjunction with the engagement tool previously described, can be used to subcutaneously manipulate strands into various configurations, including desirable loops for supporting tissue or for severing an internal structure, such as a ligament. The routing tool shown is advantageously used by inserting it through tissue and then coupling it with a tethered cannula. This can be repeated several times, if desired, to position multiple tethered cannulas through tissue for subsequent engagement by the engagement tool, as previously described.

It is also possible to have the routing tool provide the initial engagement with the engagement tool by positioning the routing tool and the engagement tool in transverse alignment at the engagement feature of the engagement tool. In this configuration, subsequently coupling a strand to the routing tool can facilitate the direct coupling of the strand to the engagement tool without necessitating a separate tethered cannula. Previously, it had been indicated that a strand under tension could be advantageously used to fully engage and capture the strand in many of the described engagement mechanisms. A strand coupled with the routing tool can be held in tension to facilitate this engagement. In this arrangement, once the routing tool is coupled to the strand, the combination of the strand and the routing tool can be considered as another embodiment of a tethered cannula.

FIGS. 127, 128 and 129 show an alternative embodiment routing tool which can also be considered a tethered cannula, and which can facilitate a more direct engagement with an engagement tool. Instead of including a strand 41 to engage a subsequent strand, the routing tool includes a strand 20a, which is shown in the front end 42a of the penetrating member 32a. For embodiments where the penetrating member 32a includes a sharp point, the blunting mechanism 33a is preferably included and the strand 20a can pass through it if it is constructed from a cannula. With the blunting mechanism 33 extended, as shown in FIG. 128, the diameter of the blunting mechanism can act as a narrow cannula and can extend farther than is shown in FIG. 128. This enables the routing tool to engage the engagement tool in similar fashion to a tethered cannula, where the initial engagement can occur with an outer cannula, in this case the penetrating member 32a. Progressive engagement and capture can then occur with a narrow cannula, in this case, the extended blunting cannula 33a, followed by final engagement with the strand 20a.

In the embodiments shown, the strand 20a includes a tip 44a. This tip 44a can be a long continuation of the strand which extends along the outside of the penetrating member, or it can be an obstructive member, such as a knot, having a sufficient size to be retained by the engagement feature of the engagement tool after it is captured. As a further alternative, magnetic particles can be provided to facilitate engagement and capture by an engagement tool with a magnet in the engagement feature. While the illustrated mechanism is shown with several elements, the front end 42a of the penetrating member of the routing tool can also be implemented with a tethered cannula having a blunt cannula, with a strand 20a coupled with the tip 44a.

The primary advantage of the arrangement shown in FIGS. 127, 128 and 129 is that the routing tool does not have to exit from the tissue to couple with a separate tethered cannula. Instead, it can couple directly with the engagement tool inside the tissue, which can be an advantage when further penetration of the routing tool by the penetrating member is obstructed or undesirable.

Figure 130:
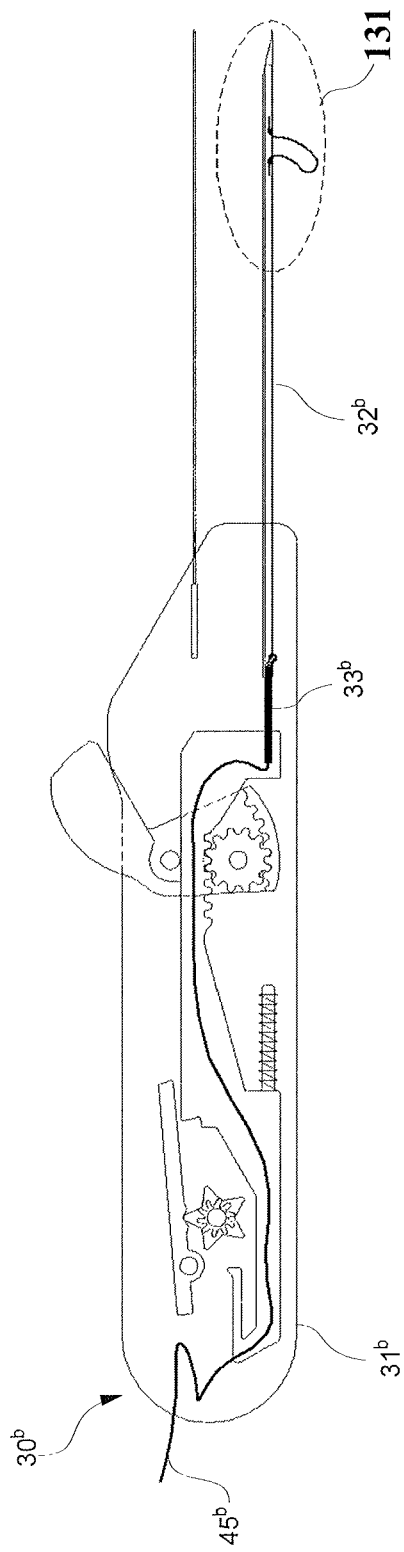
FIG. 130 is a plan view of an alternative embodiment of a routing tool which includes a fluid passageway for dispensing fluid through the penetrating member.

FIGS. 130 and 131 show an alternative embodiment routing tool 30b. In this configuration, the routing tool 30b includes a fluid pathway 45b for dispensing fluid through the tool. This can be useful for the administration of anesthetic fluids for numbing tissue and saline solutions for opening pathways through tissue, for example, through hydro-dissection, which is especially useful with penetrating members having blunt tips.

It will be understood that while the present invention has been described based on specific embodiments incorporating specified parts, the present invention further encompasses all enabled equivalents of the parts described, and that various changes in the details, materials and arrangement of parts which have been herein described and illustrated in order to explain the nature of this invention may be made by those skilled in the art within the principle and scope of the invention as expressed in the following claims.

What is claimed is:

1. An engagement tool for subcutaneously capturing a surgical suture or thread using a percutaneous procedure, the engagement tool comprising:
   a handle having a proximal end and a distal end;
   an outer cannula defining a longitudinal axis, the outer cannula extending from the distal end of the handle and having a base end and a tip;
   an engagement feature including a width portion and a height portion, the width portion defining a width along the longitudinal axis, the height portion defining a height perpendicular to the longitudinal axis, the width and height defining an opening being greater than a diameter of the suture or thread; and
   a capture mechanism movable subcutaneously between a position exposing the opening of the engagement feature, such that the suture or thread can be received by the engagement feature when the engagement feature is in transverse tangential alignment to the suture or thread, and a position closing the opening of the engagement feature, thereby capturing the suture or thread within the engagement feature, the capture mechanism being retained within the outer cannula during initial capture of the suture or thread and subsequent release of the suture or thread.

2. The engagement, tool of claim 1, wherein the capture mechanism is movable proximally or distally axially with a captured suture or thread such that the suture or thread is removable from within the outer cannula to outside of the outer cannula.

3. The engagement tool of claim 1, wherein the outer cannula contains the engagement feature.

4. The engagement tool of claim 1, wherein the outer cannula has at least one transverse cross-section including two different transverse dimensions.

5. The engagement tool of claim 1, wherein the engagement feature is formed in the outer cannula.

6. The engagement tool of claim 5, wherein the engagement feature has a generally U-shaped width portion including a first leg and a second leg, the first and second legs oriented generally parallel to the longitudinal axis, and the engagement feature has a lateral portion oriented generally perpendicular to the longitudinal axis.

7. The engagement tool of claim 1, wherein the capture mechanism is movable subcutaneously from a position wherein the engagement feature is at least partially blocked such that the suture or thread cannot be captured in the engagement feature by the capture mechanism, to a position wherein the engagement feature is exposed such that the suture or thread in the engagement feature can be captured by the capture mechanism.

8. The engagement tool of claim 1, wherein:
   the capture mechanism is movable subcutaneously from an extended position wherein the opening of the engagement feature is at least partially blocked by the capture mechanism, such that the suture or thread cannot be captured in the engagement feature, to a withdrawn position wherein the opening of the engagement feature is exposed such that the suture or thread in the engagement feature can be captured in the engagement feature between the capture mechanism and a distal end portion of the engagement feature upon subsequent movement of the capture mechanism toward the tip; or
   wherein the capture mechanism is movable subcutaneously from a withdrawn position wherein the opening of the engagement feature is at least partially blocked by the capture mechanism, such that the suture or thread cannot be captured in the engagement feature, to an extended position wherein the opening of the engagement feature is exposed, such that the suture or thread in the engagement feature can be captured between the capture mechanism and a proximal end portion of the engagement feature upon subsequent movement of the capture mechanism within the engagement feature away from the tip.

9. The engagement tool of claim 1, wherein the capture mechanism is movable subcutaneously from an extended position wherein the opening of the engagement feature is at least partially blocked by the capture mechanism, such that the suture or thread cannot be captured in the engagement feature, to a withdrawn position wherein the opening of the engagement feature is exposed, such that the suture or thread can be captured in the engagement feature between the capture mechanism and the distal end portion of the engagement feature upon subsequent movement of the capture mechanism toward the tip.

10. The engagement tool of claim 1, wherein the capture mechanism is movable subcutaneously from a withdrawn position wherein the engagement feature is at least partially blocked and the suture or thread cannot be captured in the engagement feature by the capture mechanism, to an extended position wherein the engagement feature is exposed and the suture or thread can be captured by the capture mechanism between the proximal end portion of the engagement feature and the capture mechanism when the capture mechanism is moved in the engagement feature away from the tip.

11. The engagement tool of claim 1, wherein the capture mechanism is slidably mounted within the outer cannula and is spring biased.

12. The engagement tool of claim 1, wherein the capture mechanism comprises a hook member for capturing the suture or thread.

13. The engagement tool of claim 1, wherein the capture mechanism comprises a raised member to capture the suture or thread between the capture mechanism and a proximal end portion of the engagement feature or a distal end portion of the engagement feature.

14. The engagement tool of claim 1, further comprising:
   an actuation mechanism secured to the handle and associated with the capture mechanism for moving the capture mechanism between the position where the engagement feature is exposed to the position where a suture or thread can be captured in the engagement feature.

15. The engagement tool of claim 1, wherein the capture mechanism includes a latch which flexes in response to an applied force to expose the engagement feature.

16. The engagement tool of claim 1, wherein the capture mechanism in combination with the engagement feature captures the suture or thread in a capture region that is larger than the diameter of the suture or thread.

17. The engagement tool of claim 1, further comprising:
an engagement locating member extending from the distal end of the handle and spaced from the outer cannula to be visible externally of a body of the patient when the outer cannula is inserted percutaneously into the patient and having a locating indicator, the locating indicator corresponding to a location of the engagement feature inside the tissue.

18. The system of claim 1, wherein the engagement tool has a plurality of engagement features where a suture or thread captured in a first engagement feature remains captured during a process of capturing a second suture or thread in a separate engagement feature.

19. A system for subcutaneously capturing a surgical suture or thread using a percutaneous surgical technique on a patient with a subcutaneous suture or thread, the system comprising:
a suture or thread retaining first member and a first suture or thread extending therefrom; and
an engagement tool,
the engagement tool comprising:
a handle having a proximal end and a distal end;
an outer cannula defining a longitudinal axis, the outer cannula extending from the distal end of the handle and having a base end and a tip;
an engagement feature including a width portion and a height portion, the width portion defining a width along the longitudinal axis, the height portion defining a height perpendicular to the longitudinal axis, the width and height defining an opening being greater than a diameter of the suture or thread; and
a capture mechanism movable subcutaneously between a position exposing the opening of the engagement feature, such that the suture or thread can be received by the engagement feature when the engagement feature is in transverse tangential alignment to the suture or thread, and a position closing the opening of the engagement feature, thereby capturing the suture or thread within the engagement feature, the capture mechanism being retained within the outer cannula during initial capture of the suture or thread and subsequent release of the suture or thread.

20. The system of claim 19, wherein the engagement feature includes an opening, the first member having a first cross-sectional area, the first cross-sectional area being smaller than the opening of the engagement feature such that the first cross-sectional area can fit generally transversely in the engagement feature.

21. The system of claim 19, wherein a lateral portion of the opening of the engagement feature along the longitudinal axis is at least equal to the first cross-sectional area of the first member.

22. The system of claim 19, wherein the capture mechanism can capture the first member with the engagement feature in transverse tangential alignment to the first member and then subsequently capture the suture or thread extending from the first member as the member is moved transversely within the engagement feature until the suture or thread extending from the first member is captured within the engagement feature.

23. The system of claim 19, wherein the engagement feature further comprises a region which is smaller than the first cross-sectional area of the first member but is larger than the diameter of the suture or thread so that the capture mechanism can capture but not fully close on the first member positioned in the engagement feature until the first member is moved transversely until the suture or thread extending from the first member is captured within the engagement feature so that the capture mechanism can fully close on the suture or thread extending from the first member.

24. The system of claim 19, wherein an outer surface of the outer cannula is slidably in contact with the first member within a body of the patient, alignment of the engagement feature with the first member providing tactile or electronic feedback indicating that the first member is aligned with the engagement feature.

25. The system of claim 19, wherein the engagement tool includes an engagement locating member extending from a distal end of the handle and spaced from the outer cannula to be visible externally of a body of the patient when the outer cannula is inserted percutaneously into the patient and having a locating indicator, the locating indicator corresponding to a location of the engagement feature inside the tissue.

26. The system of claim 19, wherein tactile or electronic feedback is provided when the first member is positioned at least partially in transverse tangential alignment to the engagement feature when the capture mechanism is positioned so that at least one of the suture or thread or the first cross-sectional area of the first member is captured by the capture mechanism within the engagement feature when the engagement feature is exposed.

27. The system of claim 19, wherein the suture or thread is selectively detachable from the first member.

28. The system of claim 19, wherein the engagement feature is a U-shaped slot in the outer cannula.

29. The system of claim 19, wherein the first member has a second cross-sectional area different than the first cross-sectional area.

30. The system of claim 29, wherein the second cross-sectional area is larger than the first cross-sectional area and is located proximal the first cross-sectional area which retains the suture or thread.

31. The system of claim 30, wherein only the first cross-sectional area that is smaller than the second cross-sectional area of the first member can fit in the opening of the engagement feature when the engagement feature is transversely and tangentially aligned with the first member.

32. The system of claim 29, wherein the second cross-sectional area of the first member does not fully fit into a capture region of the engagement feature, but wherein the second cross-sectional area of the first member is slidably in contact with and provides tactile or electronic feedback indicating that the first member is aligned with the engagement feature.

33. The system of claim 19, wherein the first member has a sleeve proximate to and containing therein the first member, the sleeve having an outer cross-sectional area that is larger than a first outer cross-sectional area of the first member and does not fully fit into a capture region of the engagement feature, and wherein the sleeve is slidably in contact with and provides tactile or electronic feedback indicating that the first member is aligned with the engagement feature.

34. The system of claim 19, wherein the engagement tool has a plurality of engagement features where a suture or thread captured in a first engagement feature remains captured during a process of capturing a second suture or thread in a separate engagement feature.

35. The system of claim 19, wherein the system further comprises a suture or thread retaining second member and a second suture or thread extending therefrom.

36. The system of claim 35, wherein a first suture or thread captured by the engagement tool remains captured when the second member is positioned in the engagement feature.

37. The system of claim 36, wherein the engagement tool has a plurality of engagement features where a suture or thread captured in a first engagement feature remains captured during a process of capturing a second suture or thread in a separate engagement feature.

38. The system of claim 19, wherein the first member is attached to a handle.

39. The system of claim 38, wherein the handle attached to the first member includes an engagement locating member extending from a distal end of the handle and spaced from the suture or thread retaining member to be visible externally of a body of the patient when the retaining member is inserted percutaneously into the patient and having a locating indicator, the locating indicator corresponding to the portion of the retaining member to be engaged and captured by the engagement tool.

40. The system of claim 19, wherein the capture mechanism is magnetic and the suture or thread includes an element that is magnetically attractive.

* * * * *